United States Patent [19]

Grilk

[11] Patent Number: 4,860,223
[45] Date of Patent: Aug. 22, 1989

[54] CARBON MONOXIDE HEALTH HAZARD MONITOR

[75] Inventor: Henry G. Grilk, West Milford, N.J.

[73] Assignee: Rule Industries, Inc., Gloucester, Mass.

[21] Appl. No.: 100,791

[22] Filed: Sep. 24, 1987

[51] Int. Cl.[4] .................... G06F 15/20; G06F 15/42
[52] U.S. Cl. ..................... 364/550; 340/632; 364/413.01; 364/496
[58] Field of Search .................. 73/23; 340/632, 634; 250/343; 364/496, 497, 550, 413.01, 413.02, 413.09; 128/632, 634, 710

[56] References Cited

U.S. PATENT DOCUMENTS

| | | | |
|---|---|---|---|
| 3,860,818 | 1/1975 | Stalder et al. | 340/632 |
| 4,067,004 | 1/1978 | Gulbrantson | 340/632 |
| 4,231,249 | 11/1980 | Zuckerman | 340/632 |
| 4,269,804 | 5/1981 | Kring | 73/23 |
| 4,586,143 | 4/1986 | Kaneyasu et al. | 364/497 |

Primary Examiner—Parshotam S. Lall
Assistant Examiner—Kevin Teska
Attorney, Agent, or Firm—Edwin E. Greigg

[57] ABSTRACT

An instrument for use on a marine vehicle including a sensor for determining the concentration of carbon monoxide (COC) present on the vehicle, an LED indicator for visually displaying the concentration, a microprocessor using a mathematical formula for calculating the health hazard to a person on the vehicle occasioned by the level of carbon monoxhemoglobin %COHb in the blood of that person resulting from breathing concentrations of carbon monoxide over a period of time. The instrument also determines for determining the health hazard condition in terms of long term exposure to a low COC level, moderate term exposure to a moderate COC level, and short term exposure to a high COC level, and in addition visually and audibly indicates the health hazard conditions. A method for the operating instrument, and a method of testing operativeness of the instrument are also provided.

16 Claims, 22 Drawing Sheets

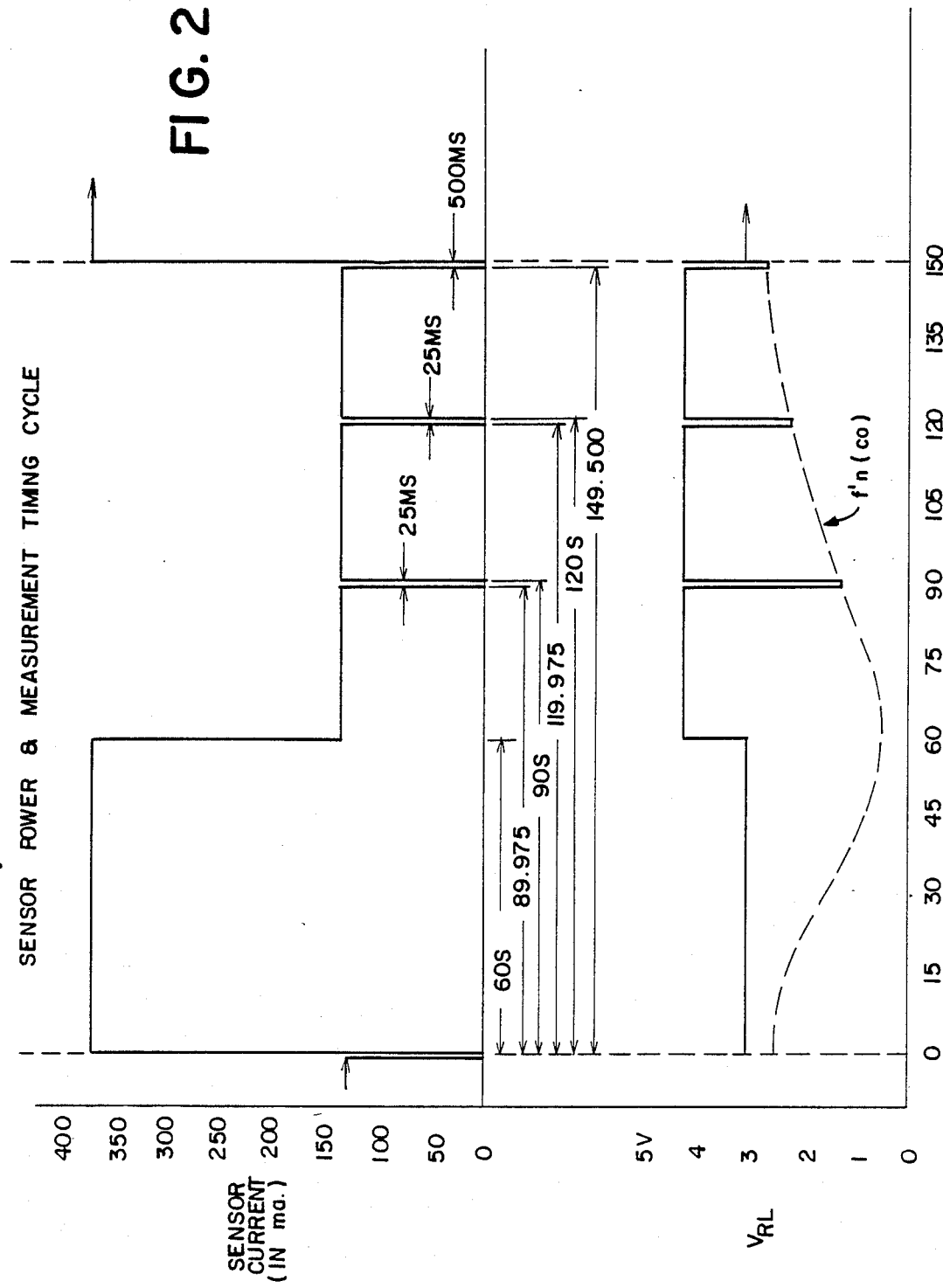

CoC VS (R/Ro)
(FROM FIGARO DATA - 203 BOOKLET, PG.9)

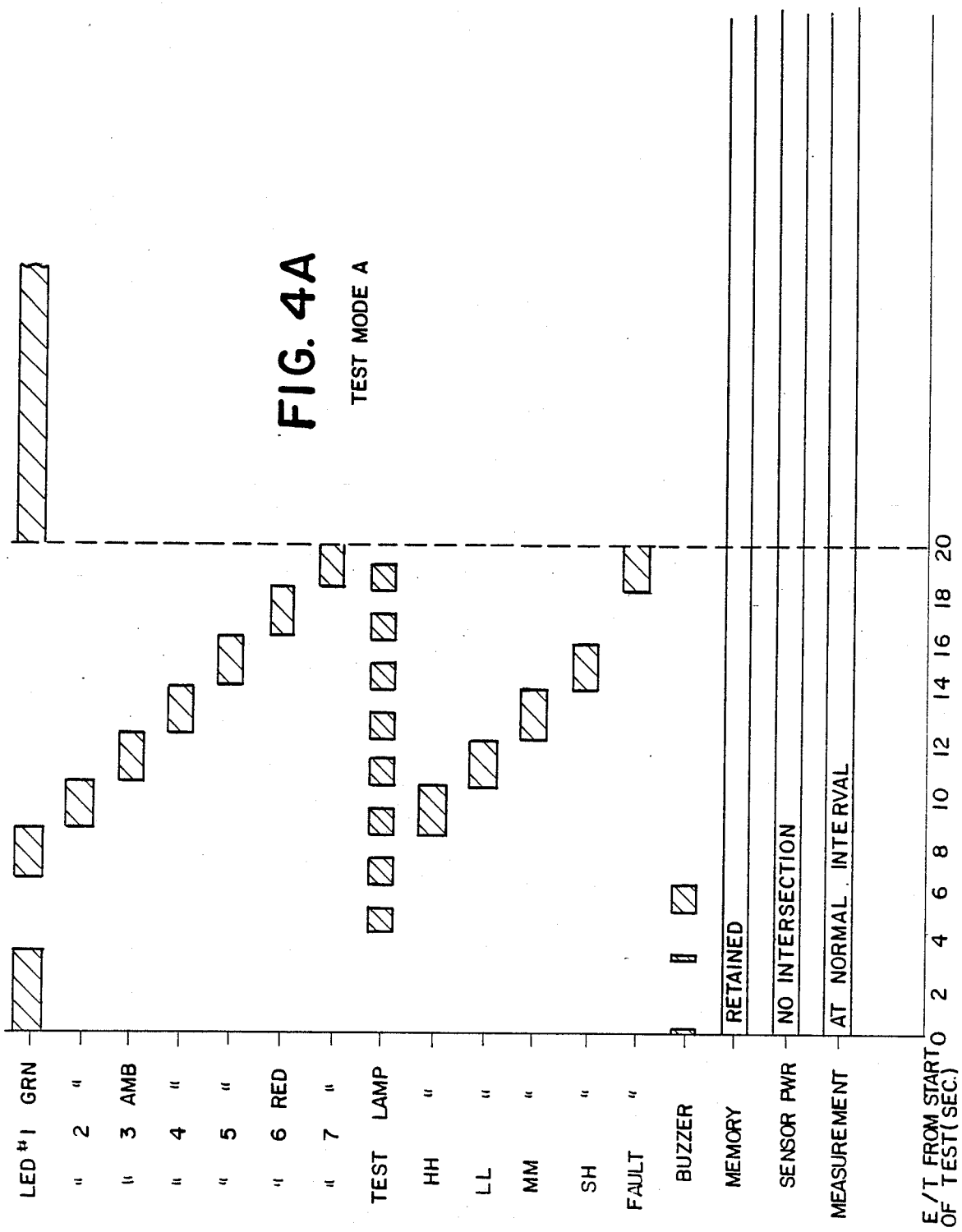

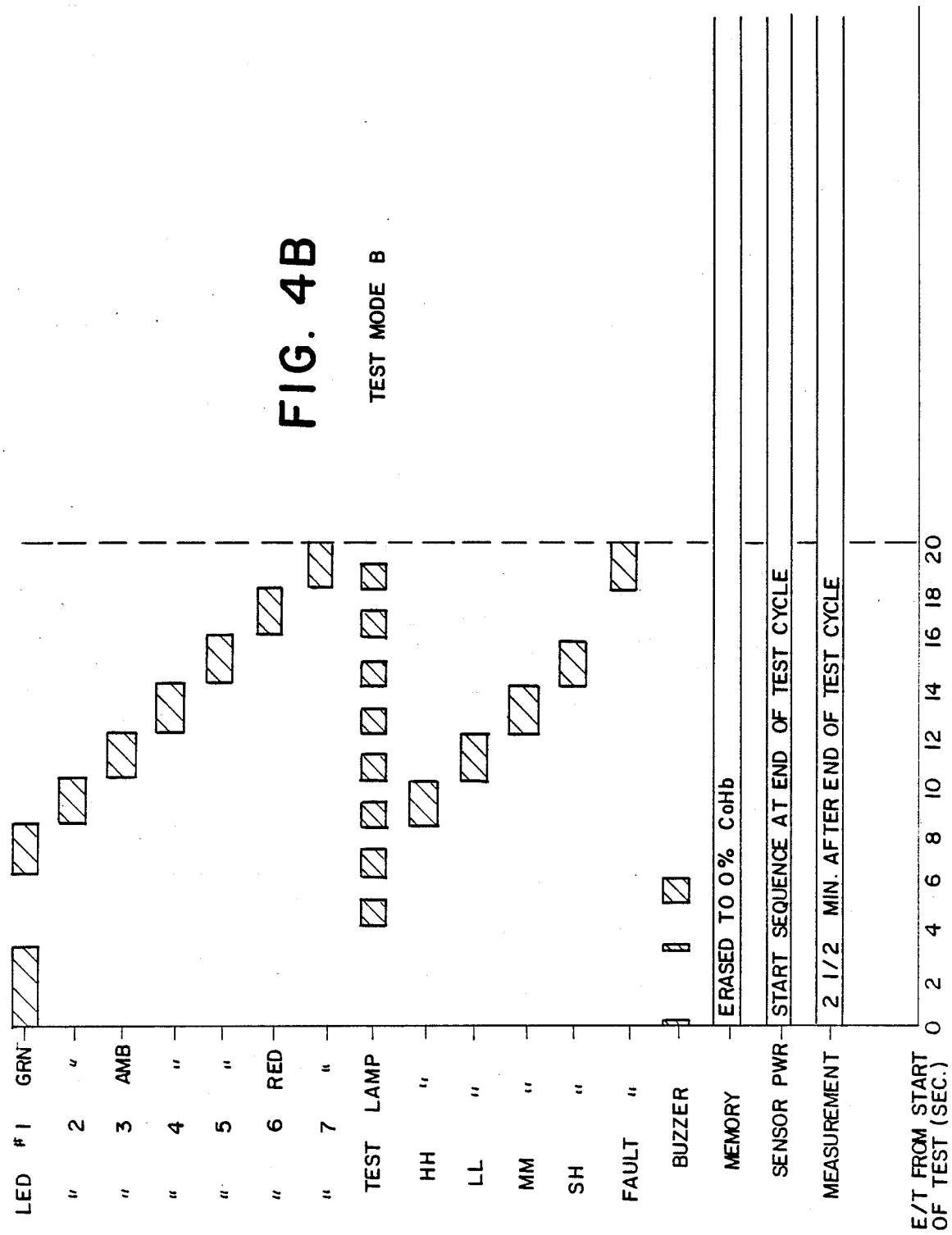

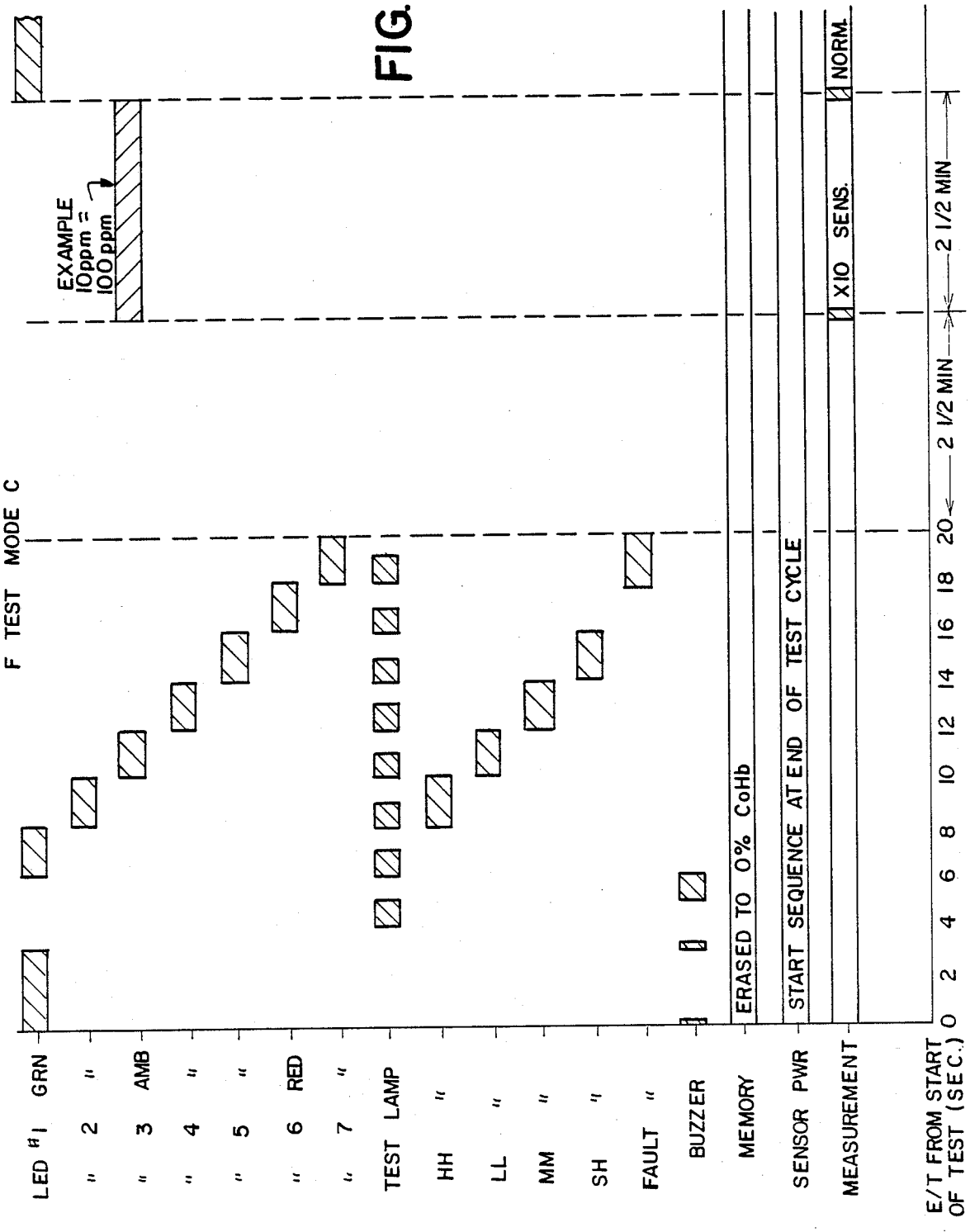

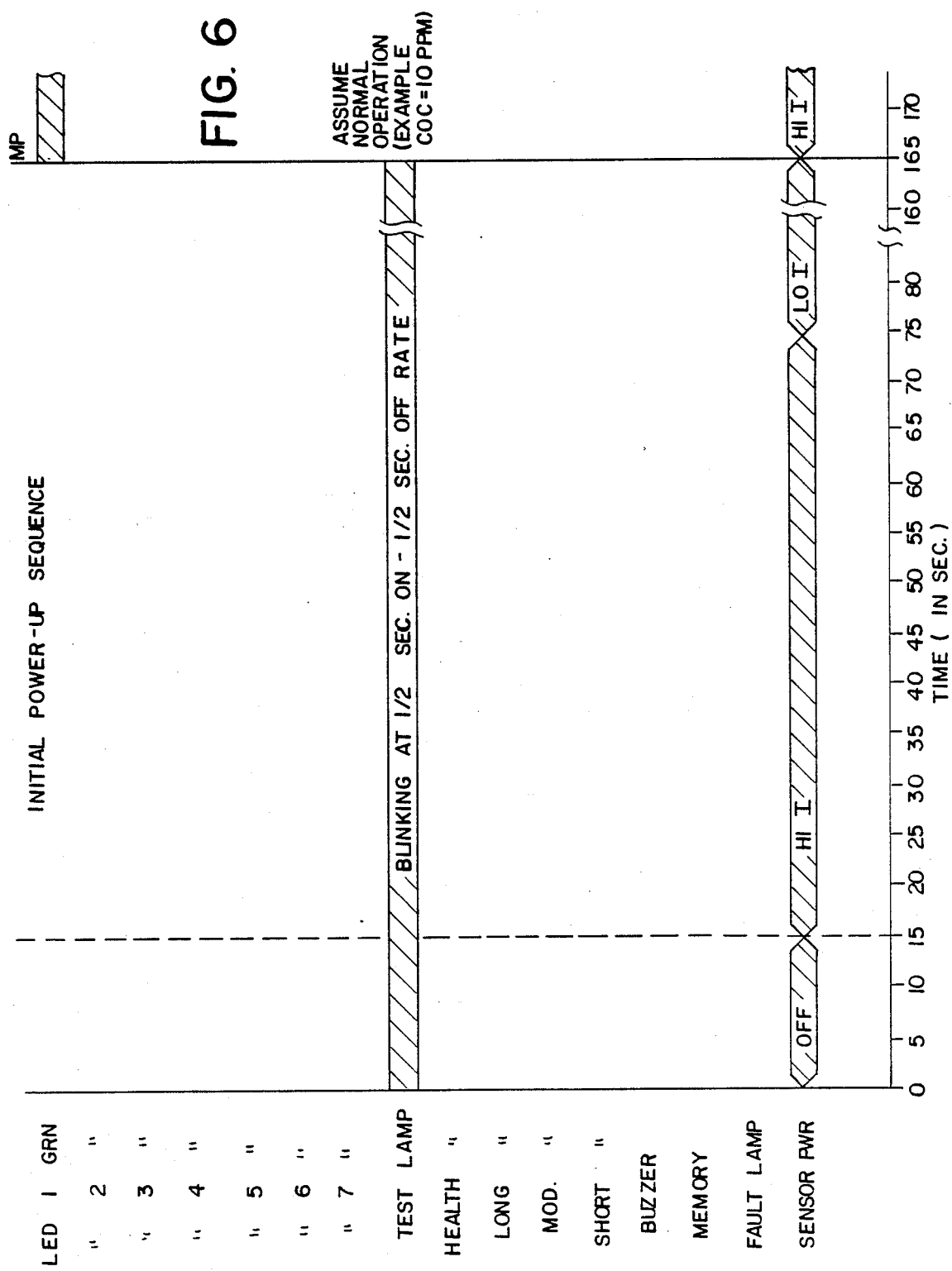

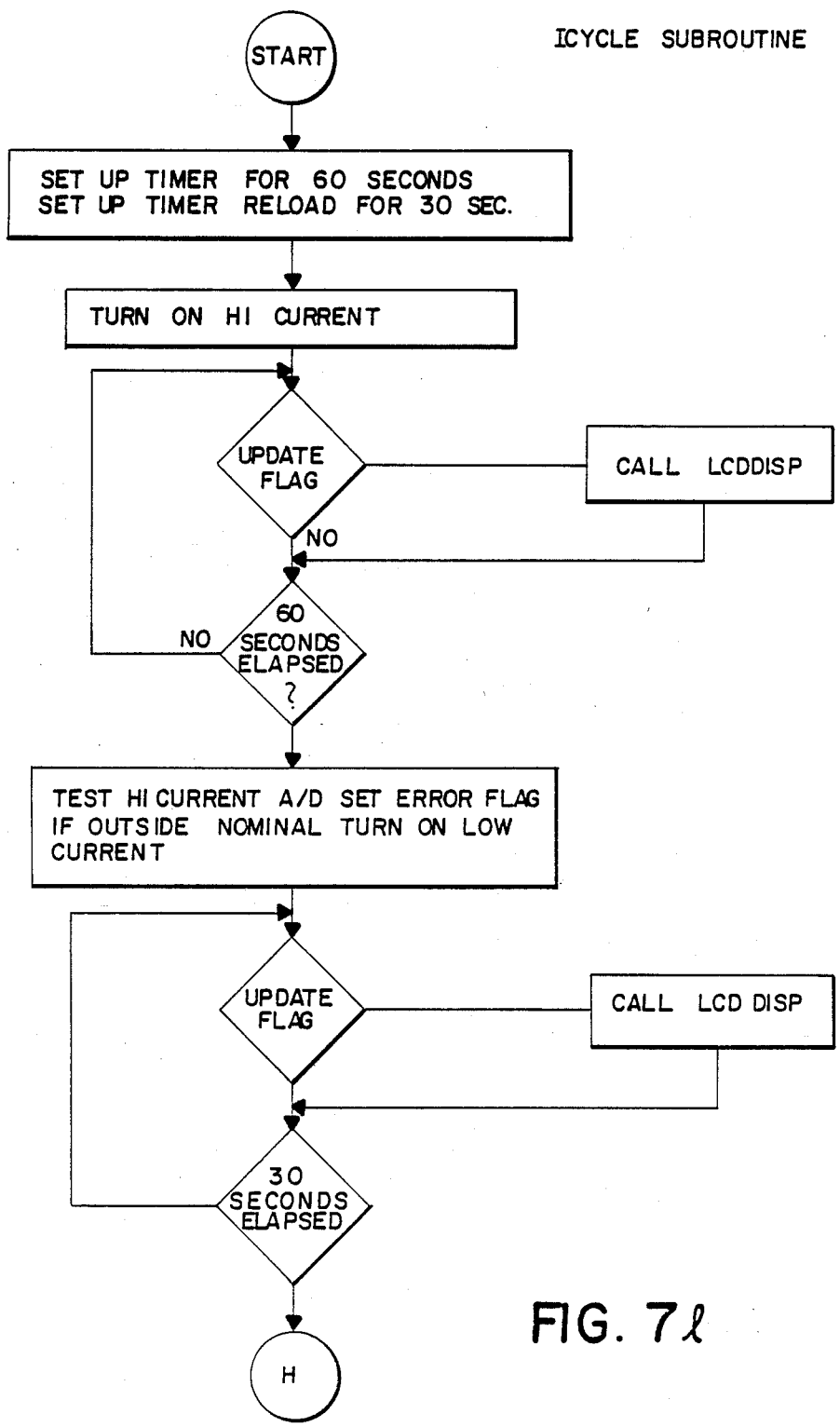
FIG. 7ℓ

CARBON MONOXIDE HEALTH HAZARD MONITOR

BACKGROUND OF THE INVENTION

The invention relates to a carbon monoxide monitor for use on marine vehicles and more particularly to an apparatus and method for monitoring the health hazard to the occupants of a marine vehicle occasioned by breathing the carbon monoxide fumes generated by the internal combustion engines of the marine vehicle.

Carbon monoxide is an odorless, colorless, and tasteless gas that is lethal if present in sufficient concentration and if at a particular concentration it is breathed over a sufficient period of time.

Carbon monoxide detectors are available for use on marine vehicles, however, these instruments function only to detect a specific selected level of carbon monoxide and to sound an alarm and/or to provide a visual indication when this level has been exceeded. It is perfectly safe to breathe a relatively low concentration of carbon monoxide e.g., 50 PPM, over an extended period of time, whereas it would be lethal to breathe a high concentration of carbon monoxide e.g., 450 PPM, over even a relatively short period of time. Thus, prior art detectors that are set at the lower level will give an alarm even though no health hazard exists. On the other hand, prior art detectors that are set to the higher level will not alarm even though carbon monoxide concentration below the alarm set point is present that may be lethal if breathed over a sufficient period of time, as for example, the amount of carbon monoxide that may be breathed by a person sleeping on a marine vehicle while internal combustion engines of the vehicle, or other sources of carbon monoxide, are operating.

It has also been determined that the lethality of carbon monoxide is not only a function of concentration and the length of time a person breathes carbon monoxide at that concentration, but also a function of such factors as the rate of diffusion of carbon monoxide into the lungs, barometric pressure, minute respiratory volume and level of exertion or work which together establish a level of carbon monoxhemoglobin (COHb), in the blood. It is the level of COHb in the blood that constitutes a health hazard rather than carbon monoxide concentration or the length of time that carbon monoxide at that concentration is breathed per se.

SUMMARY AND OBJECT OF THE INVENTION

Embodiments of the invention function to detect and alert to the presence of toxic concentrations of CO (carbon monoxide) in two ways--both in terms of the present CO level (i.e., the CO concentration, in PPM, at the most recent update, or "measuring period") and in terms of exceeding an "exposure limit" which is based on %COHb (percent carbon monoxhemoglobin) in the blood. The present CO level is visually displayed on a seven segment bar LED whch indicates the relative CO concentration at the last "measuring period" (MP). The existence of a "Health Hazard", i.e., when the exposure limit (EL) has exceeded a present %COHb level, is indicated visually by both a "Health Hazard" (HH) light and one of three "condition lights" that advises if the HH was caused by a short term exposure to a high CO concentration, long term exposure to a low CO concentration, or somewhere between those extremes. A HH condition is also accompanied by an audible alarm (buzzer) where the sound rate varies corresponding to one of the three HH conditions.

Three self-testing schemes are provided: Manual Test Mode (activated by depressing a TEST switch), Automatic Test Mode (periodic self-test during normal operation), and Production Test Mode (where the unit is commanded to self-test various circuit areas and transmit the resultant test data to a production test fixture for analysis). The Manual Test Mode is also used to activate three different test sequences: Self-test, Self-test plus memory reset, and Self-test/memory reset/"super sensitivity for one MP."

If at any time a fault is recognized by any of the self-tests, a visual FAULT light and audible alarm will be activated.

Provision is also made for an optional interface (relay) that will control external apparatus, e.g., close solenoid valves or shut off engine ignition systems when a HH condition exists.

The sensor element utilized in embodiments of this invention requires a precisely timed variable power supply which cycles the sensor current at a 60 second high current/90 second low current rate. A measurement period takes place at the end of each cycle (i.e. at the end of the 90 second low current period). The power control/MP timing is provided by a programmed microprocessor (uP).

A sensor/load resistor circuit provides a varying output voltage during the MP which is directly proportional to the CO concentration level. The output voltage of the sensor is fed to an A/D input of the uP. Three other uP A/D inputs are used for various self-test tasks. The sensor input voltage to the uP is then compared to reference data in the uP's ROM, the CO concentration level (in PPM) determined, and the appropriate LED segment activated. The CO concentration level (in PPM) is then applied to a mathematical formula to calculate %COHb and the HH and condition alarms triggered when the preselected EL is exceeded. The "condition" is determined by analyzing the rate at which COHb increases.

It is therefore the object of the present invention to provide a safe and reliable carbon monoxide monitor unit for use on a marine vehicle which not only detects and indicates the concentration of carbon monoxide present in the vehicle but also determines and displays the health hazard, resulting from the %COHb in the blood of the occupant (and the rate of increase of %OCHb) to an occupant of the vehicle, occasioned by breathing this concentration of carbon monoxide for a given period of time.

BRIEF DESCRIPTION OF THE DRAWINGS

FIG. 2 illustrates the carbon monoxide sensor power and measurement timing cycle;

FIGS. 4A-4C illustrates three manual test modes implemented by the preferred embodiment;

FIG. 6 illustrates the initial power up sequence of the preferred embodiment;

DESCRIPTION OF THE PREFERRED EMBODIMENT

The preferred embodiment of the invention comprises four main functional blocks as follows:
Sensor and Sensor Power Control
Computation
Output (Visual Display, Audible Alarm, and Relay)
Power Supply.

Each of these main functional blocks will be described below, referring to FIG. 1 and other figures of the drawings.

Figure 7A:
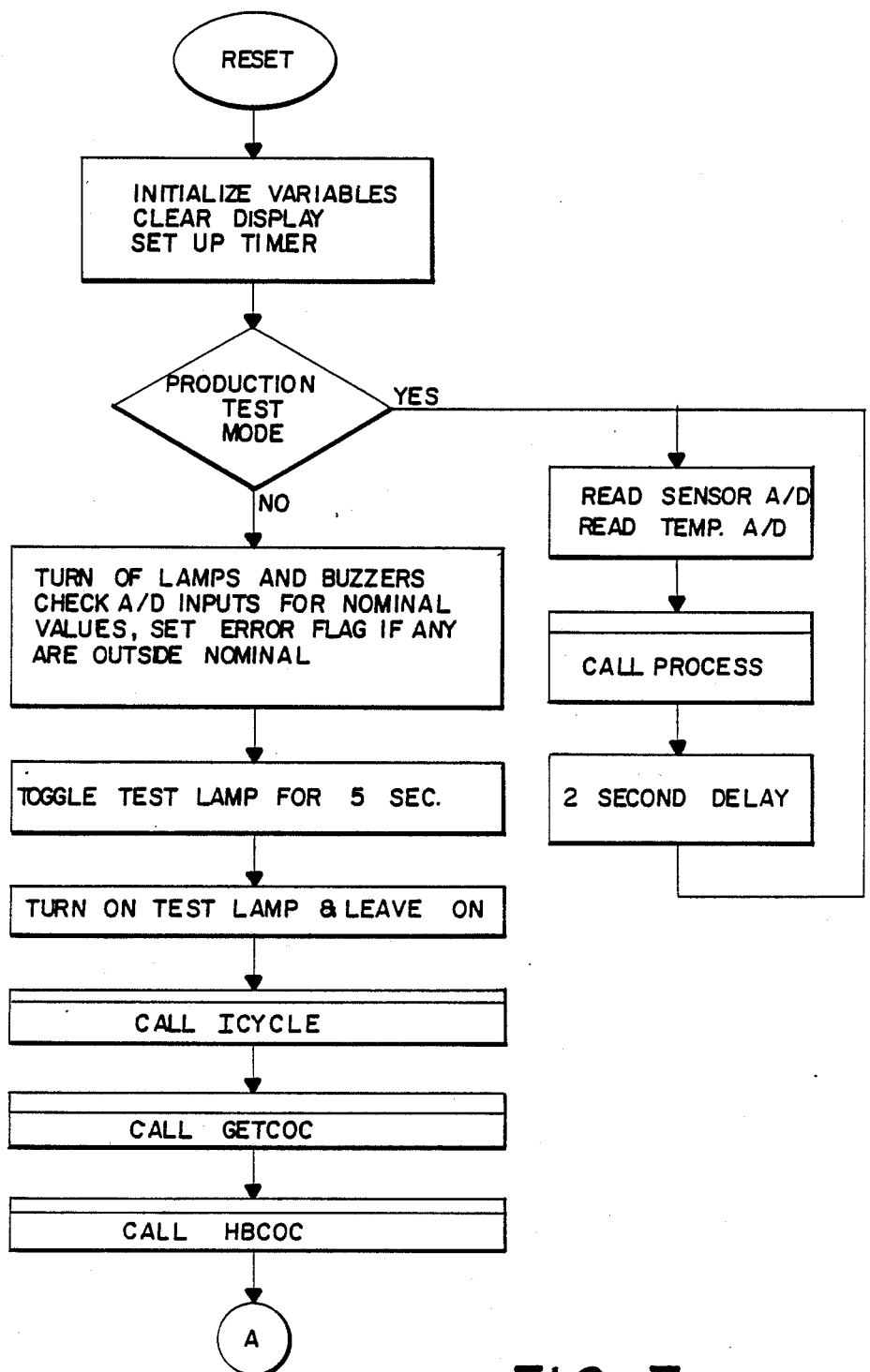
FIGS. 7A-7N are a flow diagram of the steps formed by the preferred embodiment.
Figure 7B:
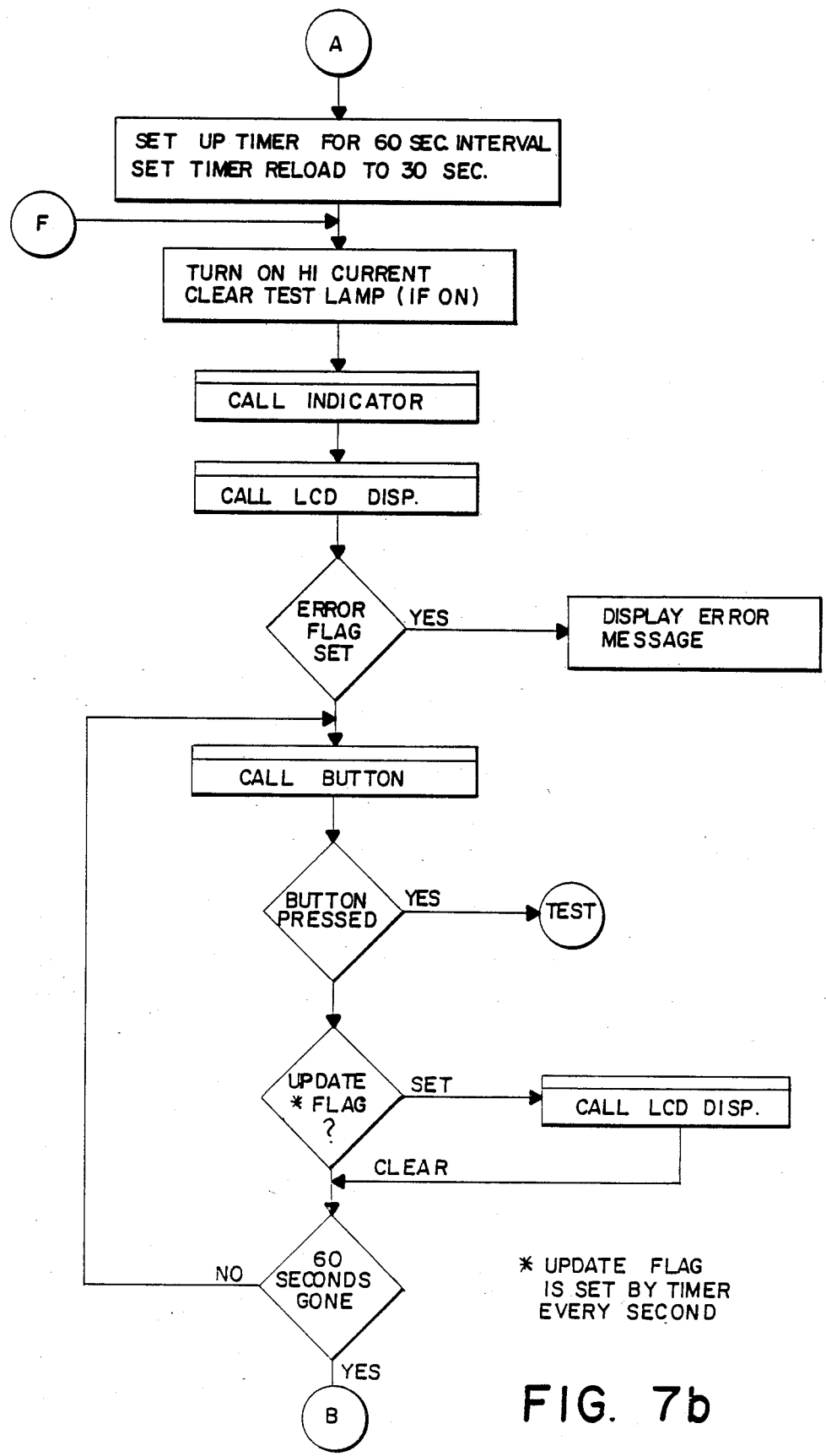
Figure 7C:
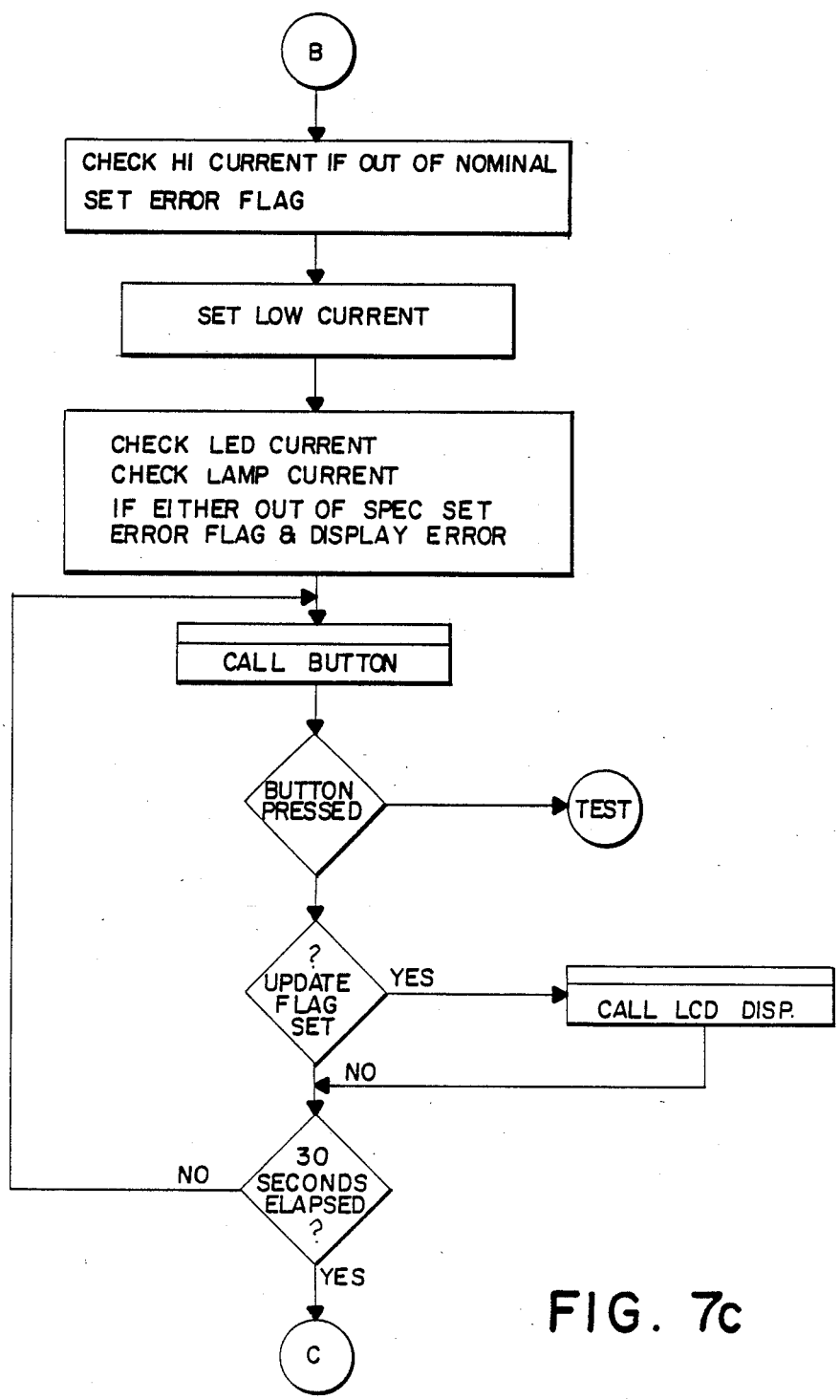
Figure 7D:
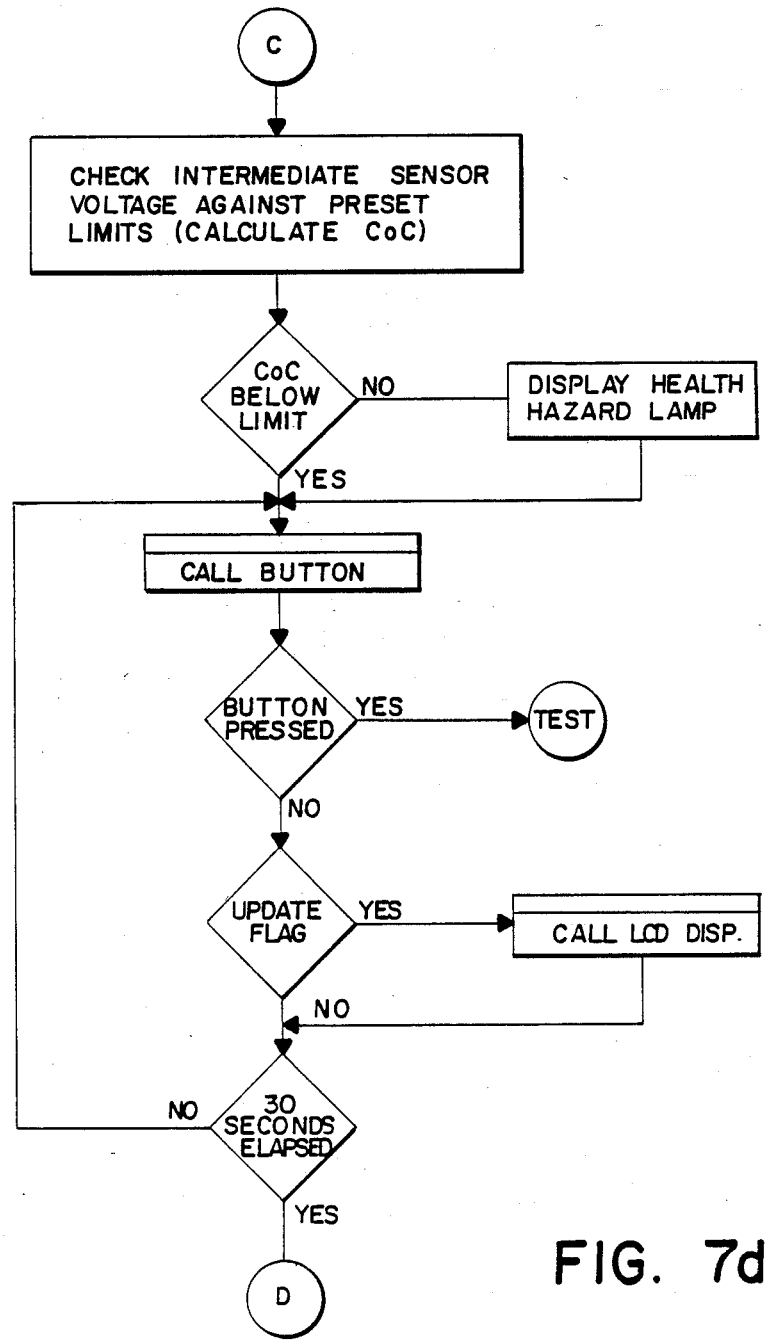
Figure 7E:
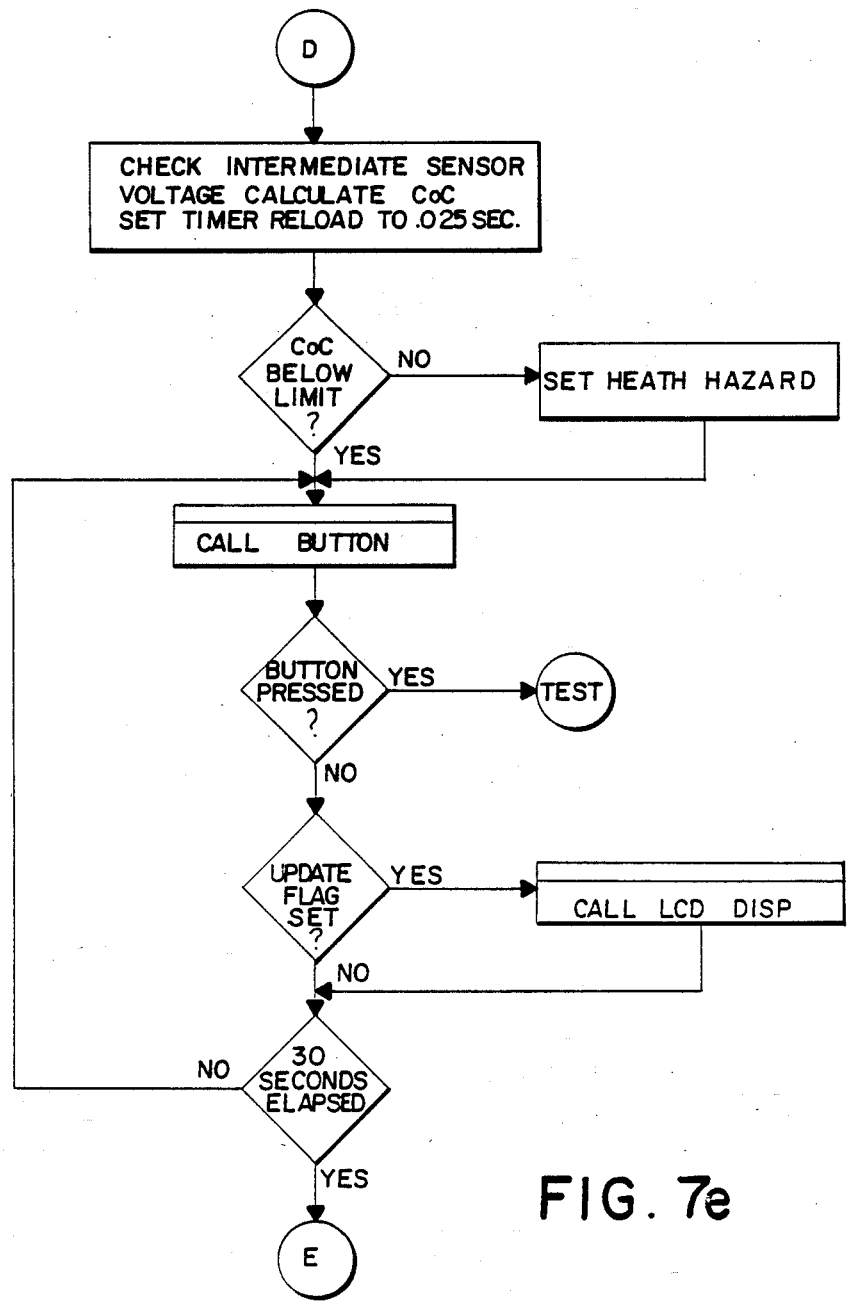
Figure 7F:
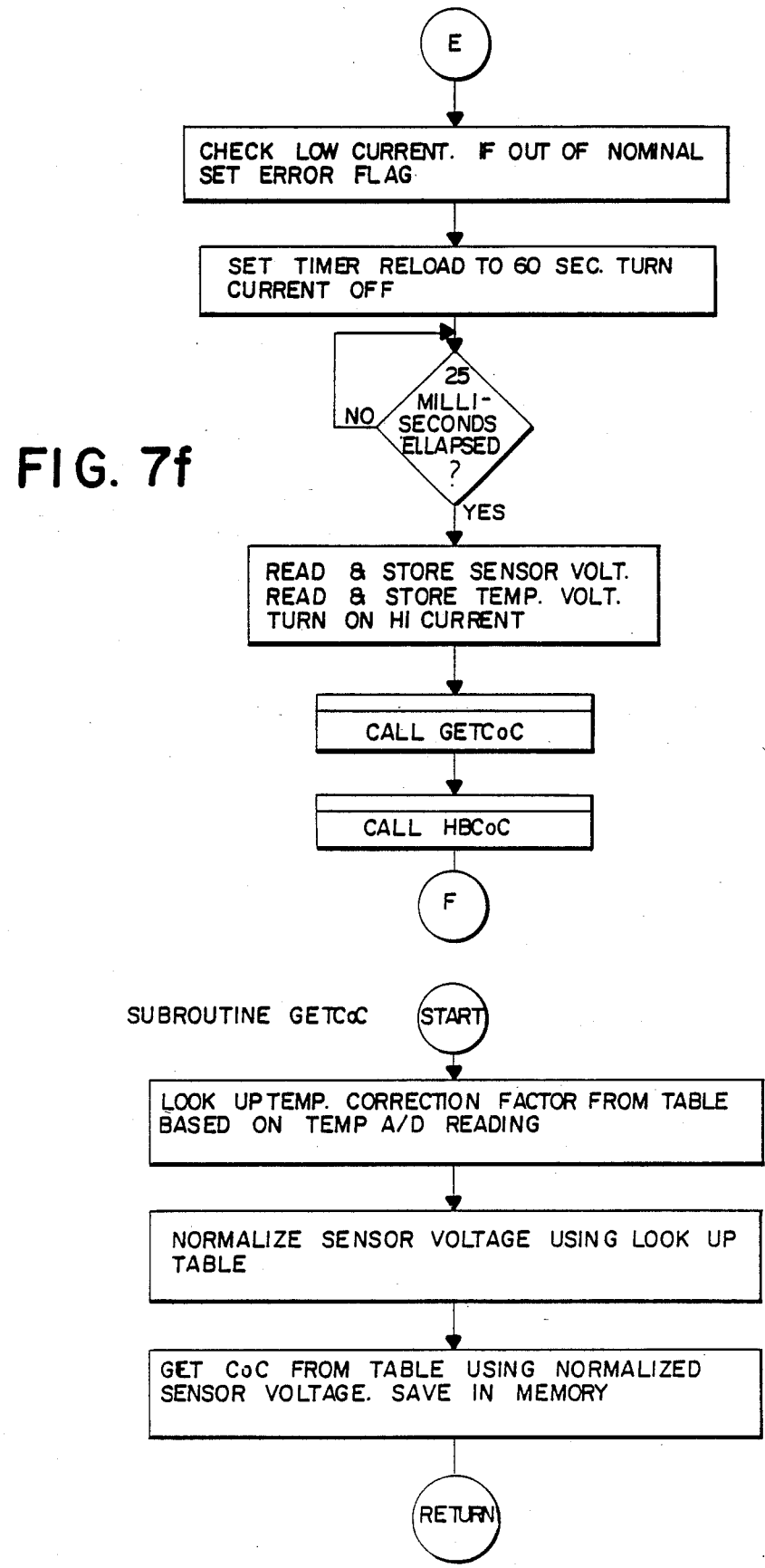
Figure 7G:
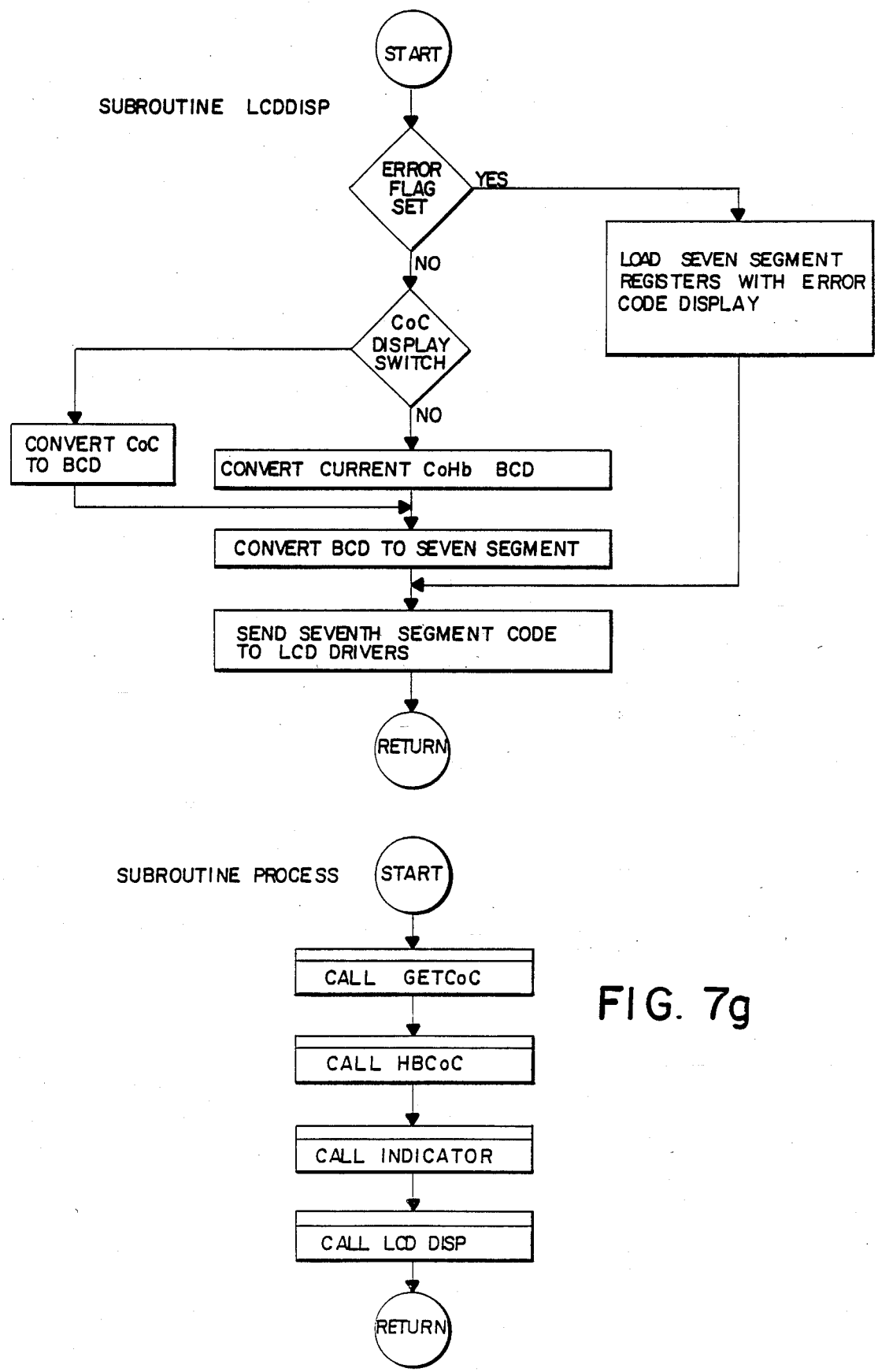
Figure 7H:
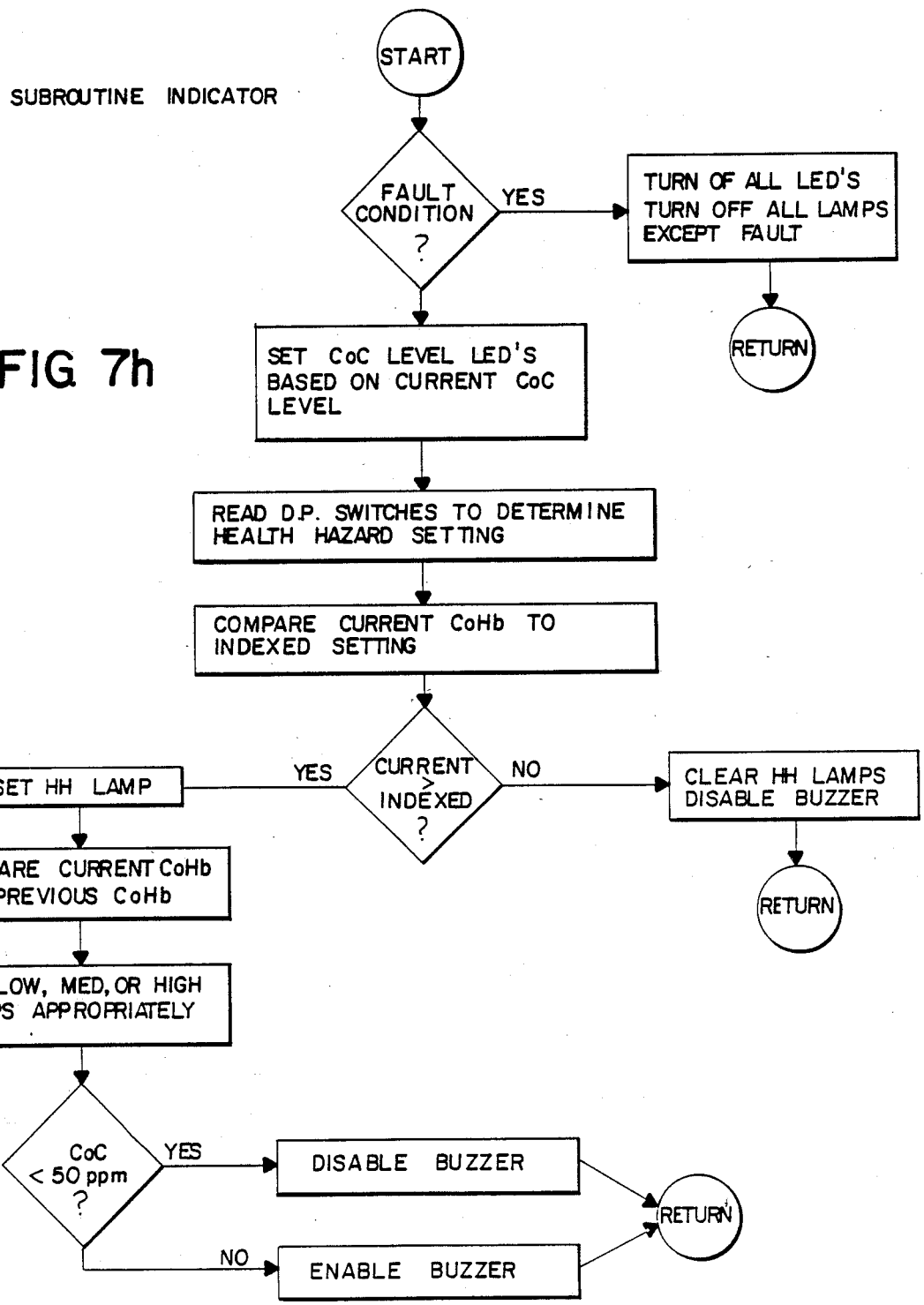
Figure 7I:
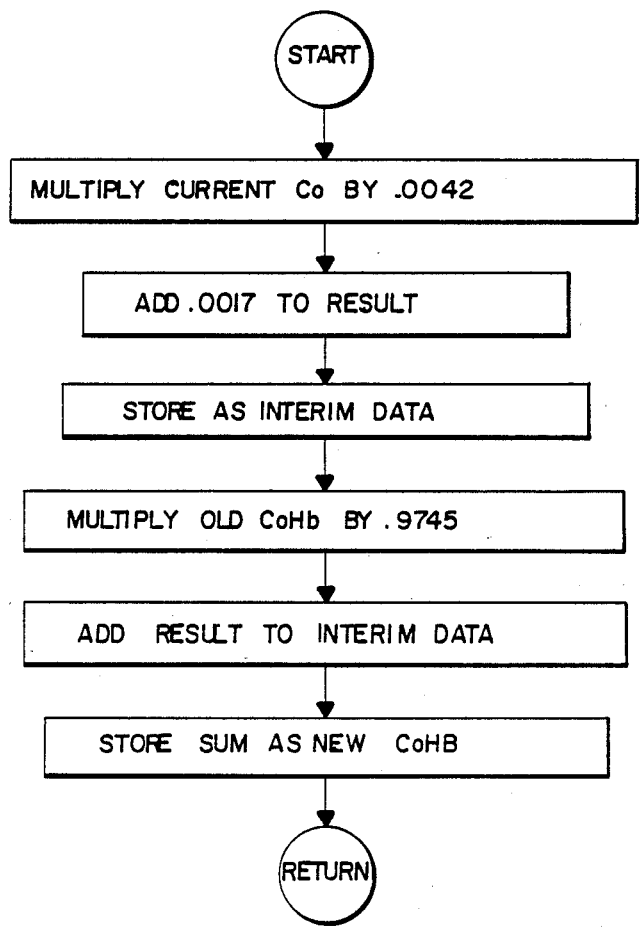
Figure 7J:
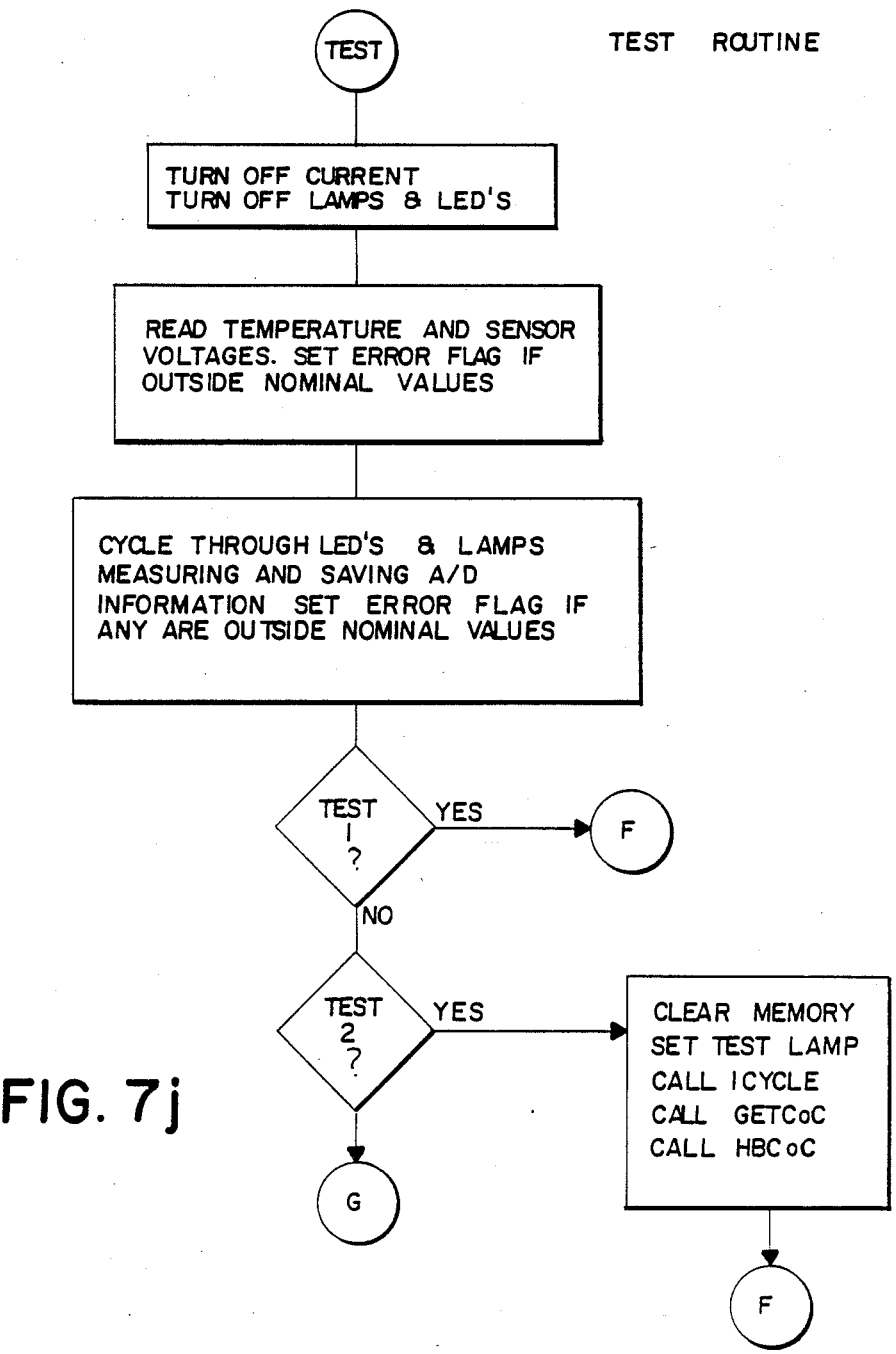
Figure 7K:
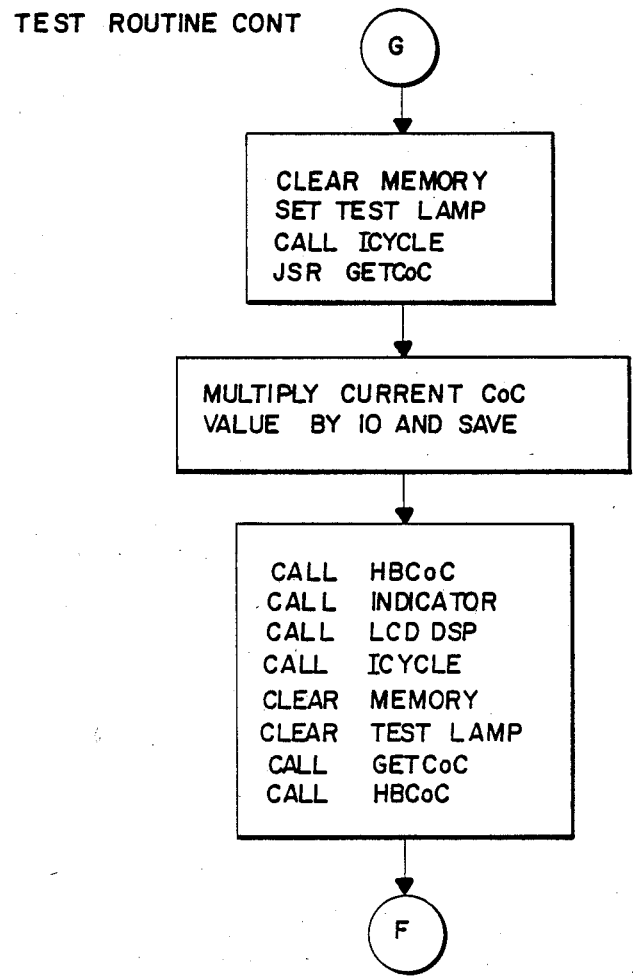
Figure 7M:
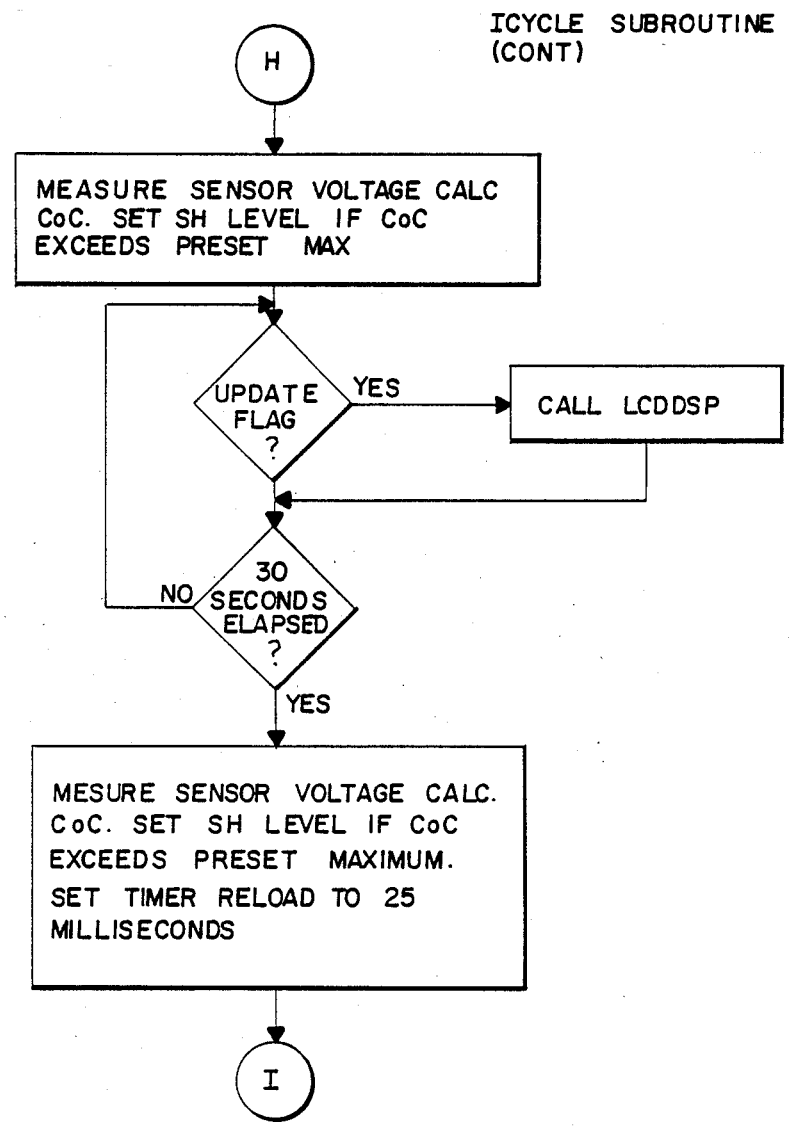
Figure 7N:
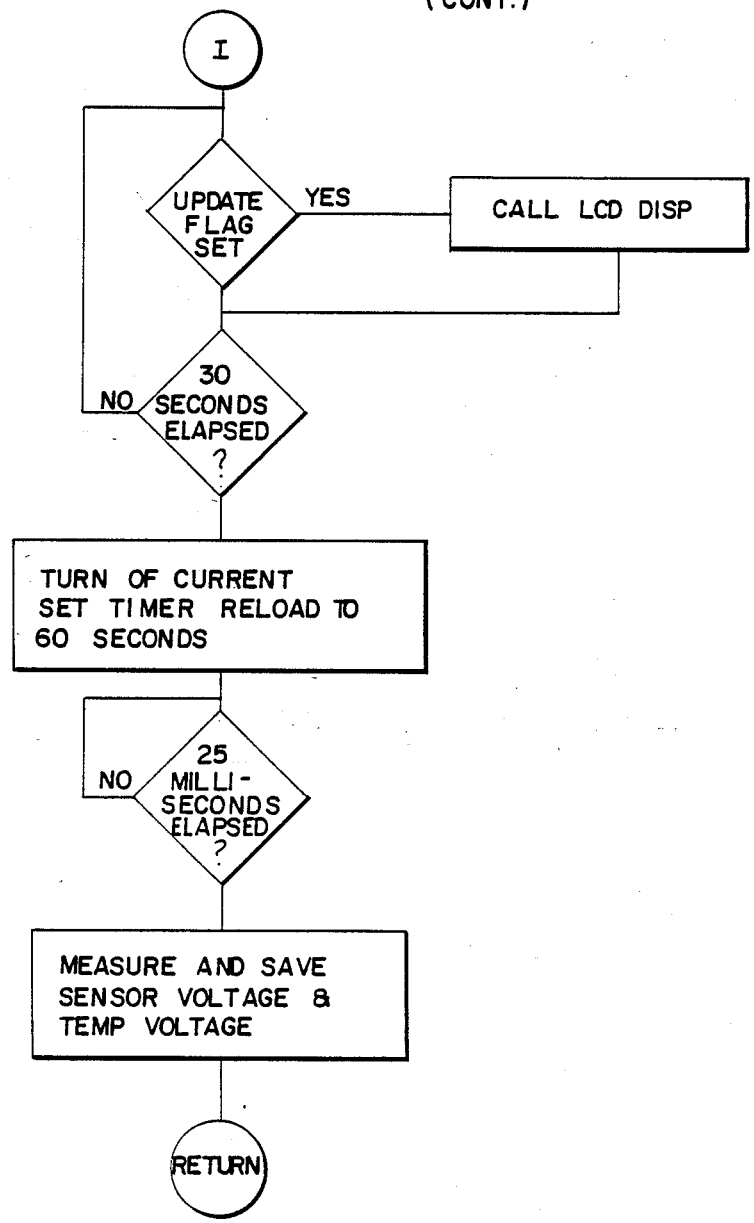

FIGS. 7A–7N constitute a flow diagram of the steps performed by the preferred embodiment of the invention. These steps will be referred to in the following description.

Figure 1:
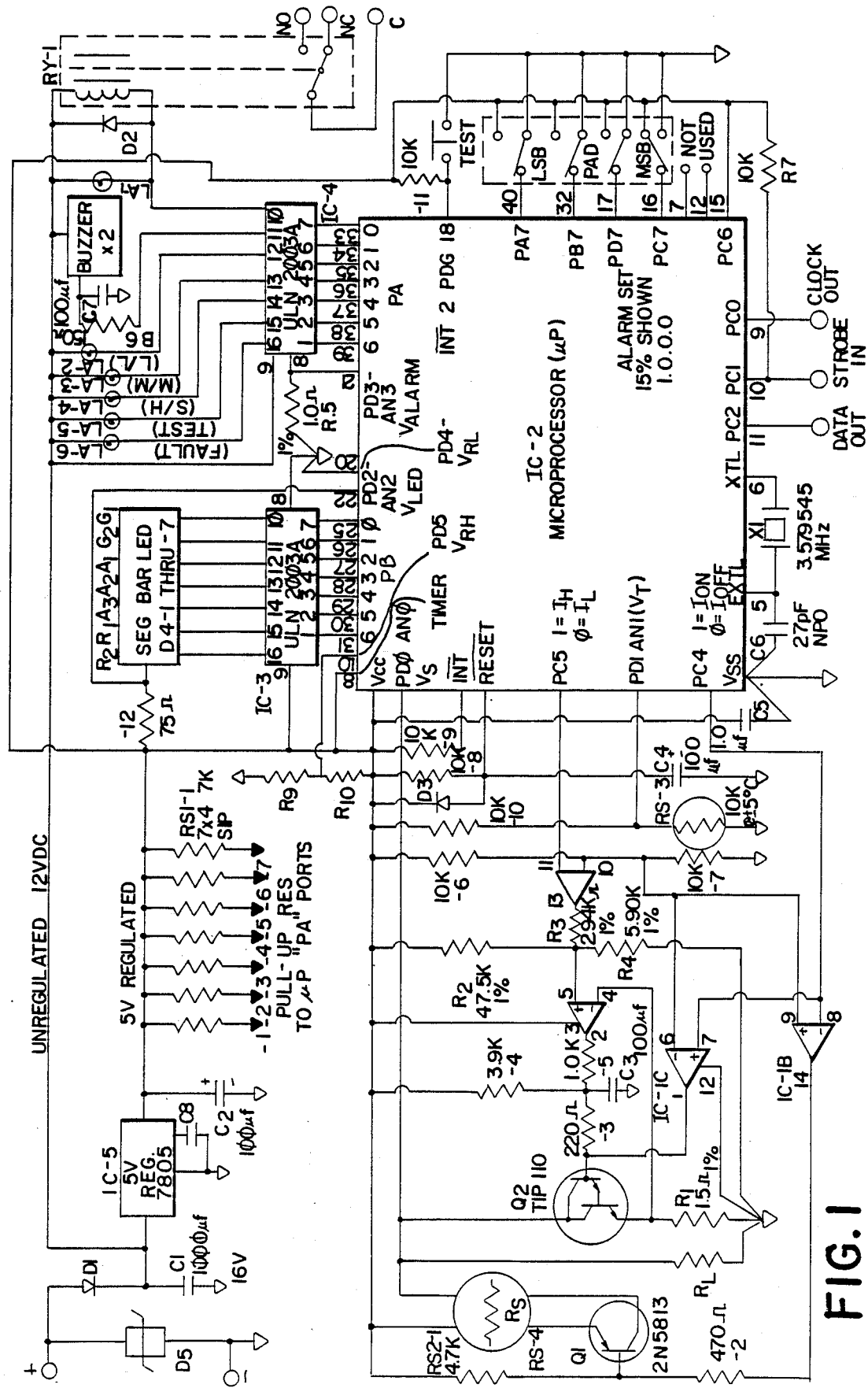
FIG. 1 is a schematic circuit diagram of a preferred embodiment of the invention.

Referring now to FIG. 1, the carbon monoxide sensor RS-4 may comprise a Figaro Model 203. When heated to various operating temperatures, the sensor responds selectively to numerous fumes (including carbon monoxide). However the temperature at which the sensor is selective to carbon monoxide is relatively low, and at that low temperature the sensor collects contaminants which impairs its performance. For these reasons, during each operation cycle (OC) of 150 seconds (2½ minutes) the sensor drive power is cycled high current, $I_H$, for 60 seconds which raises the temperature to a point high enough to purge the sensor of any contaminants which may have collected on it (see FIG. 7B), followed by low current, $I_L$, for 90 seconds which allows the temperature to cool down to the point where it is selective to carbon monoxide (see FIGS. 7C–7E). After the 90 second period has been concluded, a measuring period (MP) of 500 MS (½ second) takes place. During this time, power is removed from the heater elements of the sensor. The voltage, $V_S$, appearing across the residual resistance, $R_S$, of the sensor is then proportional to the concentration of carbon monoxide to which the sensor is exposed. In addition, during each OC, two mini measuring periods of 25 MS take place in order to guard occupants of the marine vehicle against being exposed to concentrations of carbon monoxide as would be an extreme health hazard to breathe for the 2½ minute OC, as well as for other purposes which will be later discussed. The sensor power and measurement cycle for an OC is shown in FIG. 2 where the sensor current (in ma) is shown plotted as a function of time. The voltage, $V_{RL}$, appearing across the sensor load resistance, $R_L$ (FIG. 1) is also shown in FIG. 2.

Continuing to refer to FIG. 1, after a MP, the next OC sensor power cycle is started and simultaneously the information from that just completed MP is analyzed, processed, and appropriate alarm action is initiated if necessary, as will be more fully discussed below. Periodically (as frequently as the microprocessor (uP) IC-2 operation and software will allow) the unit self-tests and certain internal voltages are checked for correct levels. At any time after the power up sequence is concluded (i.e., during a normal OC) the instrument may be manually put into one of three test modes by depression of a test switch as will be more fully discussed below. Normal OC's resume after such tests. These later functions will also be more fully discussed below.

Referring more specifically to FIG. 1, the specific operation of the sensor and sensor power control section is as follows. During the 60 second 369 ma period, microprocessor pin 14 (PC5) is at logic 1 (approximately 5 V) which causes the open collector output section of comparator section IC-1A to be off. Thus the voltage at pin 5 (+input) of comparator section IC-1D is 0.55 v, as determined by the voltage divider network consisting of R2 and R4. The current flow through R1, Q1, Q2, and the sensor elements determines the voltage across Resistor R1, which is fed to pin 4 (−input) of IC-1D. For the current to be 369 ma, the voltage across R1 must be 0.55 V. If the current is higher than 369 ma, the voltage across R1 (and thus the −input of the comparator) would be greater than 0.55 V. In that case, that output of IC-1D would turn on, which would turn Q2 off reducing the sensor current back toward 369 ma. Similarly if the current is lower than 369 ma, the voltage across R1 (- comparator input) would be less than 0.55 V. This would cause IC-1D output to turn off, allowing Q2 to conduct more current increasing it back toward 369 ma. A gentle oscillation takes place, softened by the RC network consisting of RS2-3, 2-4, and 2-5 plus C3 that maintains the current flow within less than ±1% of 369 ma.

During the 90 second 133 ma, period, microprocessor pin 14 (PC5) switches to logic 0 (approximately 0 volts) which causes the output of comparator IC-1A to turn on, placing R3 in parallel with R4, reducing the voltage at pin 5 (+input) of comparator section IC-1D from 0.55 V to 0.20 V. Following the same analysis as above, 0.20 V across R1 (−input to IC-1D) yields 133 ma sensor current.

At the end of the two sensor drive periods (60 seconds+90 seconds), microprocessor pin 13 (PC4) changes from logic 1 to logic 0 for 0.5 seconds. This, in turn, causes comparator section IC-1C output stage to turn on, shutting Q2 off. Simultaneously comparator section IC-1B output turns off thus shutting Q1 off. Therefore, during this 500 ms measuring period a voltage divider is established consisting of the residual resistance, $R_S$, between the primary and secondary elements of the sensor RS-4, (not shown) and the calibrated load resistor $R_L$. The voltage, Vs, at the junction $R_S$ and $R_L$ is proportional to the concentration of carbon monoxide present wherein the sensor is located. As CO increases, $R_S$ decreases thus raising $V_S$. Voltage $V_S$ is then sent to microprocessor analog-to-digital conversion input AN0 (pin 24, PD0). Resistors RS2-6 and 2-7 establish a reference voltage for comparator sections IC-1A, 1B, and 1C while resistors RS2-1 and −2 bias Q2.

The response of the sensor is somewhat a function of ambient temperature, in that the sensor exhibits a negative temperature coefficient. Temperature compensation is provided indirectly by measuring temperature with a voltage divider consisting of resistor RS2-10 and a negative temperature coefficient thermistor RS-3. The voltage ($V_T$) at the junction of RS2-10 and RS-3 is fed to another A/D input (pin 23, AN1-PD1) of the microprocessor.

Figure 3:
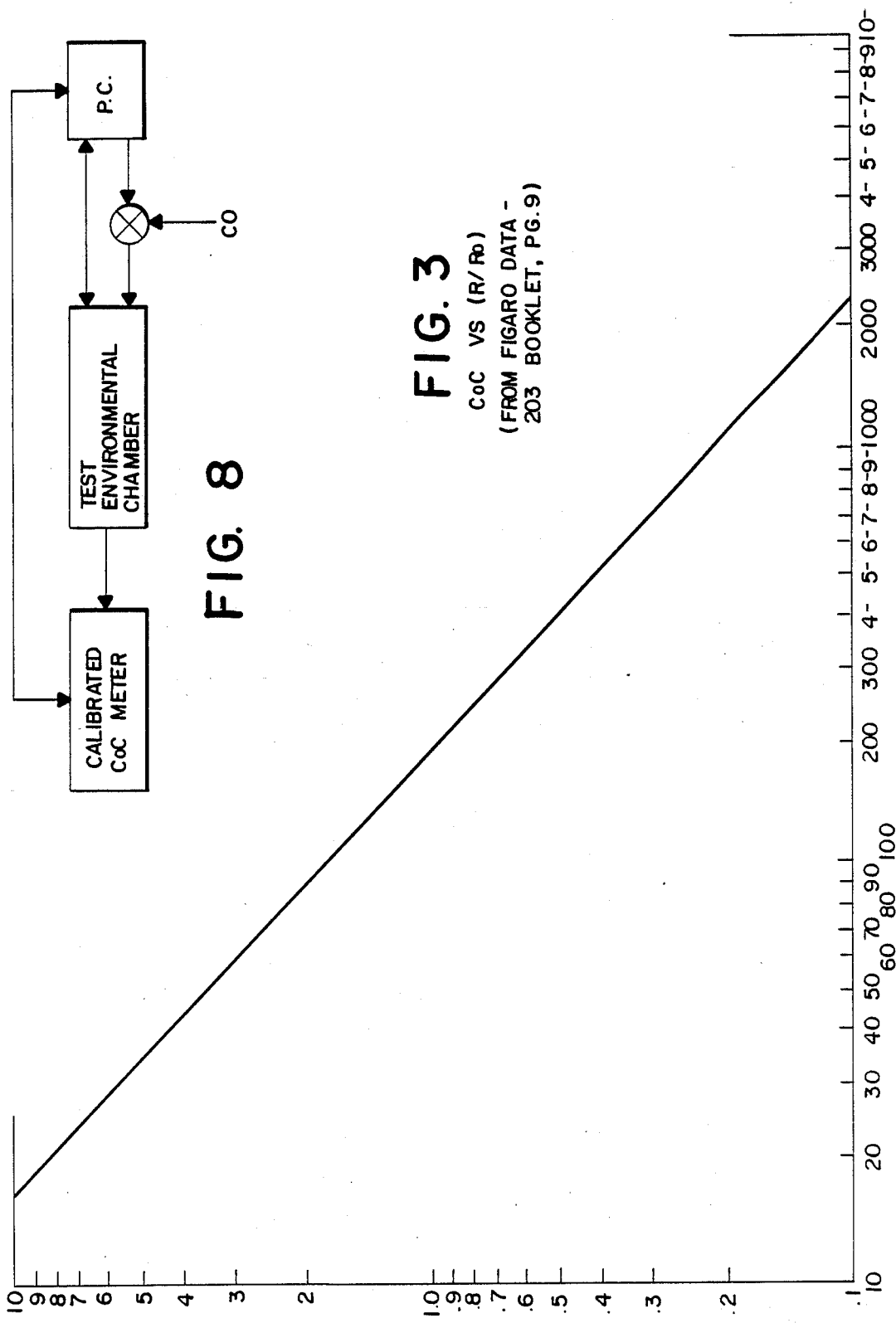
FIG. 3 is a graph showing $R/R_s$ as a function of COC.

The concentration (COC) is derived from a chart of COC vs (R/$R_S$), FIG. 3, where (R/$R_S$) is calculated by the uP as follows:

$$(R/R_S) = \frac{V_{cc}}{V_{sc}} - 1$$

where Vsc is the temperature compensated sensor voltage.

This formula is valid when $R_L=R_S$ (200 PPM) and $V_{cc}=5$ V, where:

$R_L$=sensor load resistor $R_S$=sensor resistance when the sensor is exposed to 200 PPM CO R=sensor resistance at any CO concentration.

As a function of incoming quality control inspection, all sensors received are operated in a 200 PPM CO environment and its $R_S$ determined. The sensors are then identified such that the $R_L$ will equal $R_S$ in the unit in which that particular sensor is installed. Thus, for purposes of the invention, (and uP software), the conditions for the ($R/R_S$) formula are always valid.

As noted above, the value of $V_S$ must be factored to compensate for the variation in sensor response vs. temperature. The sensor does exhibit a negative temperature coefficient (TC). Therefore, the temperature compensation factor (F) also has a negative TC. The Vsc ($V_S$— temperature conpensated) is calculated as follows:

$$Vsc=(V_S)(F)$$

where F is determined from a temperature compensation voltage (TCV) as shown in the table below:

| T | TCV | TC MULT* |
|---|---|---|
| −10 | 4.234526 | 2.5 |
| −7 | 4.123607 | 2.25 |
| −4 | 4.003051 | 2.05 |
| −1 | 3.873037 | 1.85 |
| 2 | 3.734113 | 1.65 |
| 5 | 3.587411 | 1.45 |
| 8 | 3.433486 | 1.35 |
| 11 | 3.274196 | 1.25 |
| 14 | 3.110641 | 1.15 |
| 17 | 2.944332 | 1.05 |
| 20 | 2.777086 | 1 |
| 23 | 2.610057 | .92 |
| 26 | 2.471043 | .85 |
| 29 | 2.283642 | .82 |
| 32 | 2.126602 | .79 |
| 35 | 1.975197 | .77 |
| 38 | 1.830227 | .74 |
| 41 | 1.692465 | .72 |
| 44 | 1.562156 | .71 |
| 47 | 1.439254 | .7 |
| 50 | 1.32434 | .69 |

*TC MULT is programmed into uP

TCV is generated by thermistor/resistor network RS-3, RS2-10 and is fed into the uP via another A/D input port (PDI, ANI). Thus, the complete formula for ($R/R_S$) is:

$$(R/R_S) = \frac{5}{(V_S)(F)} - 1$$

Referring to FIG. 1 of the drawings, resistor R2S-8 (in parallel with an internal pull-up resistor in the microprocessor) and capacitor C4 set up an RC time constant charging circuit to delay activating the microprocessor until initial power-up of the unit has been completed per standard practice. Diode D3 provides rapid discharge of C4 upon power-down. Crystal X1 and capacitor C6 set the operating frequency of the microprocessor and capacitor C5 is a power supply filter capacitor per standard practice.

Resistors R9 and R10 form a voltage divider that establishes the voltage reference (high) for the analog/digital conversion in the microprocessor. Resistors RS2-8, RS2-9, RS2-10, and RS1-1 through 1-7 function as pull-up resistors.

The output section consists of two types of visual displays, an audible alarm, and (optionally) a relay that can be used to control external apparatus, such as a solenoid valve or the ignition system of the internal combustion engine.

The first visual display is a seven segment bar graph type light emitting diode assembly wired with common anode and individual cathodes connected to the collectors of buffer/driver/switches (IC-3). Since there is only one LED activated at a time, a single current limiting resistor (RS2-12) from the common anode connection to +5 V is sufficient. The seven microprocessor outputs (PB0-6, Pins 25–31) drive the inputs of the B/D/S devices in IC-3 with the logic 1=LED on, 0=LED off. The voltage at the junction of RS2-12 and the common anode line is fed to the AN2 A/D input (Pin 22, PD2) for self-test analysis.

The second visual display consists of 6 incandescent lamps, one side of each connected to +12 V and the other side of each connected to the collectors of B/D/S devices in IC-4. Operation and logic is the same as noted above and is obvious.

Relay RY-1 is connected across lamp LA-1 and operates with LA-1. The relay coil may be replaced with a fixed resistor to simulate the same current drain for self-test purposes. Diode D2 is used to prevent damage to the B/D/S device due to inductive transients caused by the relay coil when power is removed.

The audible alarm (Buzzer, X2) is similarly driven by the microprocessor through a B/D/S device in IC-4. Resistor R6 and Capacitor C7 form a low pass filter to prevent feedback of the buzzer's oscillations into the B/D/S device or microprocessor.

The emitters of all B/D/S devices in IC-4 are common (Pin 8 of IC-4) and grounded through R5. The voltage at the junction of R5 and IC-4 Pin 8 is fed to the AN3 A/D input (Pin 21, PD 3) for self-test analysis.

The audible tones are produced by piezoceramic transducer/oscillator circuit ("Buzzer") that is activated by a transistor driver (switch) which in turn is driven from uP I/O port PA1 with the following logic:

| PA1 State | PA1 Voltage | Buzzer |
|---|---|---|
| Digital 0 | 0 | Off |
| Digital 1 | +5V | On |

There are four (4) different sound pulsing rates as follows:

| Sound | Use | Pulsating Rate |
|---|---|---|
| S1 | HHC = L/L | 1 second on, 9 seconds off |
| S2 | HHC = M/M | 1 second on, 4 seconds off |
| S3 | HHC = S/H | On continuously |
| S4 | Fault | 1 second on, 1 second off |
| — | Test | As noted below |

Finally the power supply simply consists of a half wave rectifier/reverse polarity protection diode, (D1), filtering (C1, and C2), and 5V regulator (IC-5). Provision is made for the addition of a surge protector (D5) and a high performance regulator with internal microprocessor reset signal generation controlled by capacitor C8.

During the MP, the voltage (Vs) from the sensor load resistor network (which is proportional to the CO concentration) is fed into an A/D input to the (PDO, ANO), factored for temperature compensation, analyzed, and the resultant data used to cause an LED to light per the following:

| LED No. | uP Port* | Color | COC (in PPM) |
|---|---|---|---|
| 1 | PB0 | Green, G1 | 0–49 |
| 2 | PB1 | Green, G2 | 50–99 |
| 3 | PB2 | Amber, A1 | 100–199 |
| 4 | PB3 | Amber, A2 | 200–399 |
| 5 | PB4 | Amber, A3 | 400–799 |
| 6 | PB5 | Red, R1 | 800–1599 |
| 7 | PB6 | Red, R2 | 1600+ |

*Logic: 0 = LED off, 1 = LED on

For reference, COC vs ($R/R_s$) vs Vsc at the key points for LED operation is as follows:

| LED No. | COC | (R/Ro) | Vsc |
|---|---|---|---|
| 1 | 0–49 | 3.64 or greater | 1.06 or less |
| 2 | 50–99 | 1.92–3.63 | 1.08–1.70 |
| 3 | 100–199 | 1.01–1.91 | 1.72–2.48 |
| 4 | 200–399 | .53–1.00 | 2.50–3.28 |
| 5 | 400–799 | .28–.52 | 3.30–3.92 |
| 6 | 800–1599 | .15–.27 | 3.94–4.38 |
| 7 | 1600+ | .14 or less | 4.40 or greater |

A health hazard (HH) exists when a preset exposure limit (EL), in terms of %COHb, has been exceeded. The %COHb is determined by applying the COC to the following formula:

$$\%COHb_{2.5} = \%COHb_\phi(0.9745) + 0.0017 + 0.0042 \cdot (COC)$$

where:
"$\%COHb_{2.5}$" is the present %COHb level, or the %COHb over the last 2.5 minute period,
"$\%COHb_\phi$" is the initial %COHb level, i.e. the %COHb level at the beginning of the last 2.5 minute period,
"COC" is the measured CO concentration in PPM.
A more general statement of the equation would be:

$$\%COHb_p = \%COHb_o(K1) + k2 + COC(k3).$$

The calculated $\%COHb_{2.5}$ from the last 2.5 minute measuring period becomes the $\%COHb_\phi$ for the next 2.5 minute measuring period.

The initial power-up %COHb (i.e., the $\%COHb_\phi$ for the first $\%COHb_{2.5}$ calculation after power-up) is 0%. The RESET function (FIG. 4b and 4c) clears the $\%COHb_\phi$ in memory to 0%.

The EL (i.e. the preset $\%COHb_{2.5}$ point) at which a HH alarm is to take place is selectable via the PA7, PB7, PC7, and PD7 uP I/O ports as follows:

| Digital Levels at | | | | EL Set Point |
|---|---|---|---|---|
| PC7 | PD7 | PB7 | PA7 | (in % $COHb_{2.5}$) |
| 0 | 0 | 0 | 0 | 7% |
| 0 | 0 | 0 | 1 | 8 |
| 0 | 0 | 1 | 0 | 9 |
| 0 | 0 | 1 | 1 | 10 |
| 0 | 1 | 0 | 0 | 11 |
| 0 | 0 | 0 | 0 | 7% |
| 0 | 0 | 0 | 1 | 8 |
| 0 | 0 | 1 | 0 | 9 |
| 0 | 0 | 1 | 1 | 10 |
| 0 | 1 | 0 | 0 | 11 |
| 0 | 1 | 0 | 1 | 12 |
| 0 | 1 | 1 | 0 | 13 |
| 0 | 1 | 1 | 1 | 14% |
| 1 | 0 | 0 | 0 | 15 |
| 1 | 0 | 0 | 1 | 16 |
| 1 | 0 | 1 | 0 | 17 |
| 1 | 0 | 1 | 1 | 18 |
| 1 | 1 | 0 | 0 | 19 |
| 1 | 1 | 0 | 1 | 20 |
| 1 | 1 | 1 | 0 | 21 |
| 1 | 1 | 1 | 1 | 22 | where
DIGITAL 0—Ground potential
DIGITAL 1—+5VDC.

There are three HH conditions (HHC) or causes for a HH alarm as follows:
L/L or long term exposure to a lower COC level,
M/M or moderate term exposure to a moderate COC level, and
S/H or short term exposure to a high COC level.

The HHC is determined by comparing the $\%COHb_{2.5}$ to the $\%COHb_\phi$ and calculating the rate of rise in %COHb in terms of %COHb per OC, as follows:

$$\%COHb_{2.5} - \%COHb_\phi = \%COHb/OC$$

where

| HHC | % COHb/OC |
|---|---|
| L/L | .01–.19 |
| M/M | .20–.99 |
| S/H | 1.00+ |

The HHC (visual and audible) and uP port status are as follows:

| HHC | HH | Lamps L/L | M/M | S/H | Buzzer |
|---|---|---|---|---|---|
| Safe | OFF | OFF | OFF | OFF | OFF |
| L/L | ON | ON | OFF | OFF | S1 |
| M/M | ON | OFF | ON | OFF | S2 |
| S/H | ON | OFF | OFF | ON | S3 |
| P port | PA0 | PA2 | PA3 | PA4 | PA1 |

Since the drivers are of the inverting type, for an "OFF" condition the uP port is a DIGITAL 0 and an "ON" condition occurs when the uP port is at DIGITAL 1.

| uP port digital levels vs HHC: | | | | | |
|---|---|---|---|---|---|
| HHC | PA0 | PA1 | PA2 | PA3 | PA4 |
| Safe | 0 | 0 | 0 | 0 | 0 |
| L/L | 1 | S1 | 1 | 0 | 0 |
| M/M | 1 | S2 | 0 | 1 | 0 |
| S/H | 1 | S3 | 0 | 0 | 1 |

The HH lamp and appropriate HHC lamp stay ON as long as the $\%COHb_{2.5}$ level is above a selected EL alarm set point. However, the audible alarm (S1, S2, or S3) sounds only when the present COC is 100 PPM plus. When the present COC drops below 100 PPM, so that either LED G1 or G2 is ON, the audible alarm stops sounding. If at any point where the present COC level again goes above 100 PPM, and the %COHb$_{2.5}$ level is still above the selected EL alarm set point, the appropriate audible alarm resumes sounding.

As shown in FIGS. 4A, 4B, 4C, there are three manual test functions that are activated by depression(s) of the TEST SWITCH (FIG. 1) as follows:

| Test | Press Test Switch | To Activate |
|------|-------------------|-------------|
| A | "1 time" | "standard self-test" |
| B | "2 times" | "self-test plus reset" |
| C | "4 times" | "self-test, reset, and super sensitivity for one MP" |

In all cases, the test switch depressions noted above are to be made within a 2.5 second period.

Test mode "A" cycles the unit's audible and visual alarm indicators and sensor power control operation as shown in FIG. 4A.

Test mode "B" is similar to "A" plus the COHb$_o$ memory is reset to 0%, as shown in FIG. 4B.

Test mode "C" is similar to "B" plus the action of increasing the sensitivity of the by a factor of 10 for the next MP ONLY, then resetting the %COHb$_o$ RAM to 0 and returning to normal. As an example, during this one "super sensitive" MP, 20 PPM actual COC would be measured as 200 PPM. This feature allows checking of the sensor's response to CO without the need for using highly toxic high levels of CO. Cigarette smoke contains 50 PPM CO. Therefore, cigarette smoke could be used to check the sensor and will cause the LED "present COC indicators" to respond. Refer to FIG. 4C for details of test moade "C".

In addition, during each of the three test modes the uP measures the LED currents (uP port PD2, AN2) for each LED and the lamp/buzzer currents (uP port PD3, AN3), the thermistor voltage, and the sensor's voltages.

Correct voltages at all uP A/D input ports vs operating conditions are detailed in the table below:

| FAULT DETECTION VOLTAGES VS CONDITION AT A/D PORTS |
|---|
| PD0/AN0 - PIN #24 - Vs (Sensor Voltage) |
| Sensor High Current |
| NOM = 2.976 V |
| MAX = 3.408 V |
| MIN = 2.607 V |
| A/D OK = 1.33–175 |
| A/D FAULT = 0–132, 176+ |
| Sensor Low Current |
| NOM = 4.168 V |
| MAX = 4.462 V |
| MIN = 3.896 V |
| A/D OK = 199–229 |
| A/D FAULT = 0–198, 230+ |
| Measurement Period |
| MAX = 4.893 |
| MIN = 0.068 |
| A/D OK = 3–249 |
| A/D FAULT = 0–2, 250+ |
| PD1/AN1 - PIN #23 - V$_T$ (Temperature) |
| High Temp Nom = 1.324 V |
| Lo Temp Nom = 4.235 V |
| Tol. Range = 1.220–4.365 |
| A/D OK = 62–224 |
| A/D FAULT = 0–61, 225+ |
| PN2/AN2 - PIN #22 - VLED (LED's) |
| ALL LED'S OFF = 4.94–5 V |
| A/D OK = 252+ |

| FAULT DETECTION VOLTAGES VS CONDITION AT A/D PORTS |   |   |   |
|---|---|---|---|
| A/D FAULT = 0–251 |   |   |   |
| ANY ONE LED ON = 2.04–4.00 V |   |   |   |
| A/D OK = 104–205 |   |   |   |
| A/D FAULT = 0–103, 206+ |   |   |   |
| PN3/AN3 - PIN #21 - VALARM |   |   |   |
| CONDX | ΔV | A/D OK | A/D FAULT |
| ALL ALARMS OFF | 0–.029 V | 0–1 | 2+ |
| BUZZER ONLY | .010–.088 V | 1–4 | 0, 5+ |
| ONE LAMP | .049–.166 V | 3–8 | 0–2, 9+ |
| HH + RY/R | .108–.303 V | 6–15 | 0–5, 16 |
| 2 LAMPS | .166–.440 V | 9–22 | 0–8, 23+ |
| 2 LA + RY + BUZZ | .186–.518 V | 10–26 | 0–9, 27+ |

If at any time (during any test sequence or during normal operation) an incorrect voltage is detected at any uP A/D input port, the "FAULT" lamp lights and the audible alarm (S4) sounds as detailed above.

During any test sequence (i.e., initial power-up or during any of the three manual tests) additional depressions of the test switch are ignored.

Periodically during normal operation, the uP checks all A/D input ports and determines if the voltages present are for the current operating condition. During every OC, the automatic self-test checks for the following:

High Level Sensor Current;
Low Level Sensor Current;
LED Current;
Lamp(s)/Buzzer/Relay Current; and
Temperature compensation network voltage (for abnormal voltage or ambient temperature outside the rated operating temperature range of 0° C. to +to°C.).

In the event that an abnormal current or voltage is detected, the "FAULT" lamp (LA-6, FIG. 1) lights and the audible alarm (S4) sounds as detailed above.

Figure 5:
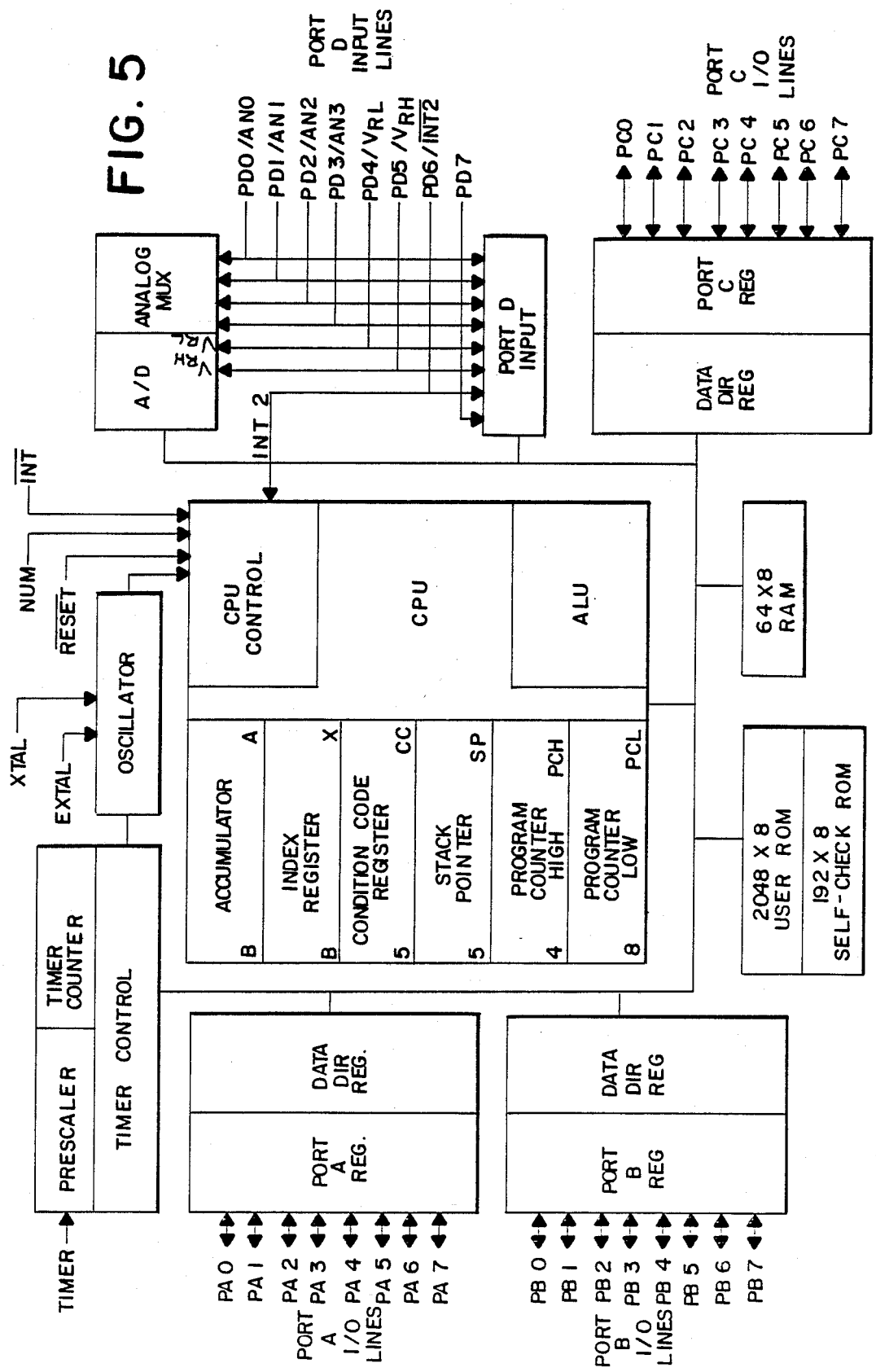
FIG. 5 shows, in block diagram form, the microprocessor portion of the preferred embodiment along with associated components.

At the time that power is initially applied to the unit (and at all subsequent "power-ups"), the %COHb$_o$ and %COHb$_{2.5}$ memory locations and all other data RAM locations (FIG. 5) are reset to 0. Then the unit cycles through the initial power-up sequence detailed in FIG. 6 and self-test.

During the sensor power control timing cycle (FIG. 2), there are two short duration periods, Mini Update Period (MUP), where power is momentarily removed from the sensor in addition to the normal MP. These periods occur at 90 seconds and 120 seconds after the start of the OC. During these MUP's (MUP—Mini Update Period), the unit measures CO and alarms (HH+SH+S3) if COC is in excess of the ceiling value specified below. It should be noted that absolute sensitivity may be somewhat below normal during the MUP, therefore, requiring slightly higher COC than the ceiling value to alarm.

At any time that the unit records a COC of 1600 PPM or higher (i.e., at any MP or MUP), the alarm is immediately sounded, HH+SH+S3, regardless of whether the %COHb$_{2.5}$ has dropped below the EL set point. Thus, 1600 PPM is the ceiling value.

Referring now again to FIG. 5,, micro- processor, IC-2, may be Motorola part 6805 R3, or the like, programmed and utilized as herein disclosed.

FIG. 7A–7N, is a flow diagram of the steps performed by the preferred embodiment of the invention described above.

An illustrative program which may be utilized to program the microprocessor and associated compliments is appended hereto as Appendix A.

A table showing the PIN connections of the microprocessor, IC-2, is given below:

MICROPROCESSOR PIN CONNECTIONS
PINOUT:

| PIN # | FUNCTION | DETAIL |
|---|---|---|
| 1 | Vss | Ground (−) |
| 2 | RESET | |
| 3 | INT | Normal Hi(Dig Readout/0=PPM,1=%COh |
| 4 | Vcc | +5.00 VDC |
| 5 | EXTAL | |
| 6 | XTAL | |
| 7 | N/C | No connection |
| 8 | TIMER | +5.00 VDC |
| 9 | PC 0 | * Clock Out |
| 10 | PC 1 | Strobe In     Production Test |
| 11 | PC 2 | * Data Out |
| 12 | PC 3 | Not Used |
| 13 | PC 4 | Sensor I (0=Off, 1=On) |
| 14 | PC 5 | Sensor I (0=Low, 1=High) |
| 15 | PC 6 | For testing(update/0=Fast,1=Nom) |
| 16 | PC 7 | % COHb Set - MSB |
| 17 | PD 7 | % COHb Set |
| 18 | PD 6/INT2 | Test Switch |
| 19 | PD 5/VRH | A/D Voltage Ref. High |
| 20 | PD 4/VRL | A/D Voltage Ref. Low |
| 21 | PD3/AN3 | A/D Input - Alarm Voltage Test |
| 22 | PD2/AN2 | A/D Input - LED Voltage Test |
| 23 | PC1/AN1 | A/D Input - $V_T$(Temp.Comp.Volt.) |
| 24 | PD0/AN0 | A/D Input - $V_S$(Sensor Voltage) |
| 25 | PB0 | LED #1 (GRN) Drive |
| 26 | PB1 | LED #2 (GRN) Drive |
| 27 | PB2 | LED #3 (AMB) Drive |
| 28 | PB3 | LED #4 (AMB) Drive |
| 29 | PB4 | LED #5 (AMB) Drive |
| 30 | PB5 | LED #6 (RED) Drive |
| 31 | PB6 | LED #7 (RED) Drive |
| 32 | PB7 | % COHb SET |
| 33 | PA0 | Health Hazard Lamp (& Relay) |
| 34 | PA1 | Buzzer |
| 35 | PA2 | "Low-Low" Lamp |
| 36 | PA3 | "Mid-Mid" Lamp |
| 37 | PA4 | "Short-High" Lamp |
| 38 | PA5 | Test Lamp |
| 39 | PA6 | Fault Lamp |
| 40 | PA7 | % COHb Set (LSB) |

*Also Digital Display Output

Referring now again to FIG. 1, the alarm set, e.g., 15% is accomplished by connecting micro-processor, IC-2 ports, PA 7, PB 7, PC 7, and PD 7, through a pad to +5 V or to ground. Port, PC 7, has coupled thereto the most significant bit (MSB) while port PA 7 has coupled thereto the least significant bit (LSB).

Figure 8:
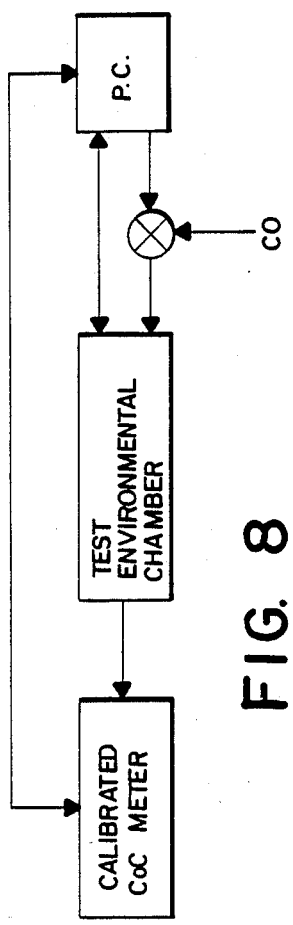
FIG. 8 is a block diagram of a production test fixture according to the invention.

Referring now to FIG. 8, during production testing, the unit under test will be prompted by the production test fixture (IBM P.C. XT or the like) to check certain internal voltages and transmit the resultant data back to the test fixture/P.C. for analysis. The production test sequence will generally be as follows:

a. Insert units to be tested into test fixture in test environmental chamber.
b. Close chamber and activate test sequence by appropriate key entry on the P.C.
c. The test sequence begins with a purging cycle where the chamber's atmosphere is replaced with "clean" air.
d. All units under test are powered-up and allowed to operate for 10-15 minutes in the "clean" air to stabilize.
e. After a stabilized condition is reached, the %COHb$_o$ memory of each unit is reset to 0 and then each unit is prompted to step through various operating conditions and measure and record certain voltages for later transmission back to the P.C. as follows:

| Step | Action (Condition) | Measure Voltage At |
|---|---|---|
| 1 | Sensor current HI | PD0-AN0 |
| 2 | Sensor current LO | " |
| 3 | LED No. G1 only | PD2-AN2 |
| 4 | LED No. G2 only | " |
| 5 | LED No. A1 only | " |
| 6 | LED No. A2 only | " |
| 7 | LED No. A3 only | " |
| 8 | LED No. R1 only | " |
| 9 | LED No. R2 only | " |
| 10 | Fault lamp only | PD3-AN3 |
| 11 | Test lamp only | " |
| 12 | HH lamp only* | " |
| 13 | L/L lamp only | PD3-AN3 |
| 14 | M/M lamp only | " |
| 15 | S/H lamp only | " |
| 16 | Buzzer only | " |
| 17 | TCV | PD2-AN2 |
| 18 | Vs (in clean air) sensor I =0 | PD0-AN0 |

*or HH lamp plus relay f. The uP is prompted to transmit the data recorded in Step "e" to the P.C. and stored in the P.C.'s memory for later analysis.
g. At this point the Test Fixture P.C. causes a valve to open which allows Carbon Monoxide to be injected into the chamber. The COC level is monitored by a calibrated COC meter, the output of which is fed to the P.C. When the COC level reaches 50 PPM, the valve closes. The COC meter continues to monitor the COC level in the chamber and causes the P.C. to open the valve as necessary to maintain a level of 50 PPM.
h. After the chamber and the units under test have stabilized in the 50 PPM COC environment, each unit is again prompted to step through the various operating conditions noted in Step "e", and transmit this data to the P.C. as noted in Step "F".
i. Steps g and h are repeated at 200 PPM and 800 PPM COC.
j. At the conclusion of the operational test, the P.C. causes the chamber to purge and replace its 800 PPM CO atmosphere with "clean" atmosphere (COC less than 15 PPM). When the chamber atmosphere is clean, a "test cycle completed" indicator will alert the operator to open the chamber and remove the units under test.
k. After the test sequence is completed, the P.C. system prints out the test data for each unit, to indicate pass or fail condition, and, if a failure, the cause of the failure.

For purposes of digital readout of COC in PPM, micro-processor port PCO (Pin No. 9) serves as a clock out for production test and port PC2 (Pin No. 11) similarly serves as Data Out (and port PC1, Pin No. 10, a strobe input). During periods when the uP is not being prompted (via strobe input) to down load data to the test fixture, the Data and Clock output lines are to drive a P/N IC-D0024 33 segment LCD display driver and display COC in PPM up to four digits to 10 PPM resolution. For Digital Display of COC (in PPM), the uP interrupt (INT) line (FIGS. 1, 5), Pin No. 3, is held at logic 0. The PPM display is updated at each MP.

The drive ports, etc., readout %COHb$_{2.5}$ in percent to 0.01% resolution with leading zero blanking above 1%. For %COHb$_{2.5}$, the INT line is held at logic 1.

Switching the display back and forth between COC (PPM) and %COHb$_{2.5}$ occurs at the time the INT line is switched from logic 0 to 1 or 1 to 0.

As noted above, if at any time during any test sequence (i.e., Manual, Automatic, or Production), or during normal operation, an incorrect internal voltage/current is detected at any uP A/D input port, the "FAULT" lamp lights and the audible alarm sounds (S4) as detailed above, and all other indicators (LED, lamps, buzzer, etc.) are inhibited, until such time that the fault is corrected.

During the production test, the nature of the fault is printed out at the conclusion of the test indicating when the fault occurred, at what A/D input port the fault was observed, the incorrect voltage measured, and what it should have been at that point.

Upon acknowledging that a fault has occurred, an error code corresponding to the cause of the fault is displayed per the following:

| Error Code | Condition |
| --- | --- |
| 0 | High Sensor Current |
| 1 | Low Sensor Voltage |
| 2 | High Sensor Voltage |
| 3 | High Temperature |
| 4 | Low Temperature |
| 5 | BCD Conversion Overflow |
| 6 | Bad Test Switch (shorted) |
| 7 | Low A/D 2* |
| 8 | High A/D 3* |
| 9 | Lo Temperature* |
| 10 | Hi Temperature* |
| 11 | Bad Led |
| 12 | Low Lamp Voltage |
| 13 | High Lamp Voltage |
| 14 | Miscellaneous |

*During test mode only - PC6 at logic 0

The foregoing relates to the preferred embodiments of the invention, it being understood that other variants and embodiments thereof are possible within the spirit and scope of the invention, the latter being defined by the appended claims.

APPENDIX A

```
         PL 57
         TITLE AQUAMETER MODEL 450 CO SCENTRY      7/10/86
         STTL Microware Systems
         RECSIZE 32
         OPTIONS H ; Current hardware is 68705r3 MCU ; ****************************
; ****************************
; ***                      ***
; ***    M O D E L   4 5 0     ***
; ***    ---------   -----     ***
; ***                      ***
; ***   MICROWARE SYSTEMS  ***
; ***       AQUAMETER      ***
; ***   COPYRIGHT (C) 1986 ***
; ***   ALL RIGHTS RESERVED ***
; ***                      ***
; ****************************
; ****************************

PAGE
; SYSTEM EQUATES

PORTA    EQU    000H    ; port a data register
         PORTB    EQU    001H    ; port b data register
         PORTC    EQU    002H    ; port c data register
         PORTD    EQU    003H    ; port d data register
         PADDR    EQU    004H    ; port a data direction register
         PBDDR    EQU    005H    ; port b data direction register
         PCDDR    EQU    006H    ; port c data direction register
         TDR      EQU    008H    ; timer data register
         TCR      EQU    009H    ; timer control register
         MSCREG   EQU    00AH    ; Miscellaneous Register
         ADCON    EQU    00EH    ; A/D control register
         ADREG    EQU    00FH    ; A/D result register
         WORK1    EQU    60H     ; WORKING STORAGE
         WORK2    EQU    5FH     ; WORKING STORAGE
```

```
WORK3     EQU    3EH         ; WORKING STORAGE
WORK4     EQU    3FH         ; WORKING STORAGE
MATH.0    EQU    4AH         ; MULTIPLY & DIVIDE REGS
MATH.1    EQU    4BH         ; MULTIPLY & DIVIDE REGS
MATH.2    EQU    4CH         ; MULTIPLY & DIVIDE REGS
MATH.3    EQU    4DH         ; MULTIPLY & DIVIDE REGS
MATH.4    EQU    4EH         ; MULTIPLY & DIVIDE REGS
MATH.5    EQU    4FH         ; MULTIPLY & DIVIDE REGS
MATH.6    EQU    WORK2       ; EXTENDED MULTIPLY REG
FLAG0     EQU    5DH         ; FLAG REGISTER 0
FLAG1     EQU    5CH         ; FLAG REGISTER 1
TIME.0    EQU    50H         ; TIME LS COUNT
TIME.1    EQU    51H         ; TIME MS COUNT
DSPBNC    EQU    5BH         ; DISPLAY SWITCH DEBOUNCE TIMER
TIMER     EQU    35H         ; Debounce timer location
SECNT.0   EQU    36H         ; Seconds counter
SECNT.1   EQU    37H         ; Ditto.
NXTIM.0   EQU    33H         ; Next .01 second down counter value <ls>
NXTIM.1   EQU    34H         ; Next .01 second down counter value <ms>
TMP.0     EQU    52H         ; TEMP DATA
TMP.1     EQU    53H         ; TEMP DATA
TMP.2     EQU    54H         ; TEMP DATA
COC1.0    EQU    31H         ; CURRENT COC
COC1.1    EQU    32H
VSENS     EQU    30H         ; SENSOR VOLTAGE A/D/ INPUT
TEMP      EQU    3DH         ; TEMPERATURE VOLTAGE A/D/ INPUT
COHB0.0   EQU    40H         ; OLD %CO IN Hb
COHB0.1   EQU    41H         ; MIDDLE BYTE
COHB0.2   EQU    42H         ; MS
COHB1.0   EQU    3AH         ; NEW %CO IN Hb
COHB1.1   EQU    3BH         ; MIDDLE BYTE
COHB1.2   EQU    3CH         ; MS
CONST.0   EQU    43H         ; CONST STORAGE
CONST.1   EQU    44H         ; CONST STORAGE
CTMP.0    EQU    45H         ; INTERIM RESULTS
CTMP.1    EQU    46H         ; INTERIM RESULTS
CTMP.2    EQU    47H         ; INTERIM RESULTS
SHLMP     EQU    11H         ; SH HH LAMP VALUE
MMLMP     EQU    09H         ; MM HH LAMP VALUE
LLLMP     EQU    05H         ; LL HH LAMP VALUE
NOLMP     EQU    00H         ; NO HH LAMP VALUE
LMPMSK    EQU    0E2H        ; LAMP DRIVER MASK
LBUZZ     EQU    05EH        ; BUZZER ON TIMER
LOFF.0    EQU    038H        ; BUZZER OFF TIMER (LS)
LOFF.1    EQU    039H        ; BUZZER OFF TIMER (MS)
BTIMER    EQU    05AH        ; BUTTON 2.5 SECOND TIMER
TBUTT     EQU    059H        ; # OF BUTTON PRESSES DURING 2.5 SECONDS
SENSCHK   EQU    58H         ; COC SENSOR MONITOR STORAGE
MAXLED    EQU    205         ; MAX A/D INPUT WITH 1 LED ON
MINLED    EQU    102         ; MIN A/D INPUT WITH 1 LED ON
STATE     EQU    57H         ; TEST STATE VARIABLE
SAVE.0    EQU    56H         ; TEST DATA STORAGE
SAVE.1    EQU    48H         ; TEST DATA STORAGE
SAVE.2    EQU    49H         ; TEST DATA STORAGE
COCHB     EQU    55H         ; 1 BYTE % BLOOD LEVEL
CF.0      EQU    2EH         ; low temperature correction factor
CF.1      EQU    2FH         ; high byte temperature correction factor
COCIDX    EQU    2DH         ; latest PPM carbon monoxide index value
DISBUF    EQU    2BH         ; 2B-2C is display buffer
BCD0      EQU    25H         ; LS bcd storage
BCD1      EQU    26H
BCD2      EQU    27H         ; MS bcd storage
SAVACC    EQU    24H         ; Error display Accumulator save register
SAVX      EQU    23H         ; Error display x reg save register
ERRCOD    EQU    22H         ; Last noted error code
TIMDL1    EQU    DISBUF
TIMDL2    EQU    DISBUF+1

; Model 450 FLAG BIT ASSIGNMENTS
;---------------------------------
```

```
;       FLAG 0
;       7       :   6        :   5      :   4      :   3      :   2      :   1       :   0      :
;---------------------------------------------------------------------------------------------
;       TEST    :   OLD      :   FAULT  :   BUZZER :   HH1    :   HH0    :   HEALTH  :   timer  :
;       MODE    :   INT      :   EXISTS :   ENABLE :   00=L/L :   01=M/M :   HAZARD  :   elapsed:
;               :   STATE    :          :          :   10=S/H :   11=X   :   EXISTS  :          :
;---------------------------------------------------------------------------------------------
;               PAGE
;       FLAG 1
;       7       :   6        :   5      :   4      :   3      :   2      :   1       :   0      :
;---------------------------------------------------------------------------------------------
;       Lead    :   Error    :   UPDATE :          :  BUZZER  :  CURRENT :  TEST MODE STATE :
;       Zero    :   Display  :   DISPLAY:          :   REQ    :  BUZZER  :  00 = T0   01 = T1 :
;       Blank   :   Request  :          :          :          :   STATE  :  10 = T2   11 = T3 :
;---------------------------------------------------------------------------------------------
;       PORTA (LAMPS)
;       7       :   6        :   5      :   4      :   3      :   2      :   1       :   0      :
;---------------------------------------------------------------------------------------------
;       DIP     :   LONG     :   MED    :   SHORT  :   TEST   :   FAULT  :   BUZZER  :   HEALTH :
;       SWITCH  :   EXPOSR   :   EXPOSR :   EXPOSR :          :          :           :   HAZARD :
;       7       :            :          :          :          :          :           :          :
;---------------------------------------------------------------------------------------------

PAGE
                ORG 0F38H            ; Mask Options Register Address
                DB 00H               ; Select Crystal Oscillator ORG 0FF8H
                DW TIMINT            ; TIMER INTERRUPT VECTOR
                DW EXTINT            ; EXTERNAL INTERRUPT VECTOR
                DW SWINT             ; SOFTWARE INTERRUPT VECTOR
                DW RESET             ; INITIAL RESET VECTOR ORG 0080H
; Health hazard check values
LLVAL:          DB 000H, 007H, 0D0H   ; %COHB/OC = .20
MMVAL:          DB 000H, 027H, 010H   ; %COHB/OC = 1.00

HICHKI:         DB 128,187
LOCHKI:         DB 190,245

;               PORT DATA AND DIRECTION INITIAL VALUES
INITVAL:
                DB 000H              ; PORTA DATA
                DB 000H              ; PORTB DATA
                DB 000H              ; PORTC DATA
                DB 000H              ; PORTD DATA
                DB 07FH              ; ADDR DATA
                DB 07FH              ; BDDR DATA
                DB 035H              ; CDDR DATA

;---------------------------------------
;               SEVEN SEGMENT LOOK-UP TABLE
SEGTBL:
                DB 077H, 041H, 03BH, 06BH     ; DIGIT 4
                DB 04DH, 06EH, 07EH, 043H
                DB 07FH, 04FH

DB 06FH, 003H, 076H, 057H     ; DIGIT 3
                DB 01BH, 05DH, 07DH, 007H
                DB 07FH, 01FH

DB 07BH, 00AH, 05DH, 04FH     ; DIGIT 2
                DB 02EH, 067H, 077H, 04AH
                DB 07FH, 06EH

DB 07DH, 030H, 06EH, 07AH     ; DIGIT 1
                DB 033H, 05BH, 05FH, 070H
                DB 07FH, 073H
```

```
;------------------------
EXTINT: RTI                 ; NO EXTERNAL INTERRUPT
SWINT:  RTI                 ; Or Software Interrupt either.

;------------------------
MEMCLR: LDA #0
        LDX #60H
MEMINIT:
        STA ,X              ; clear ram for initial use.
        DECX
        CPX #0FH
        BNE MEMINIT
        RTS ;------------------------
RESET:  SEI                 ; Disable external interrupts
        LDA #40H
        STA TCR             ; Disable timer interrupts
        LDX #0
INITIO: LDA INITVAL,X
        STA ,X
        INCX
        CPX #8              ; done loading initial values?
        BNE INITIO
        BSET 6,MSCREG       ; MASK OUT INT2 INTERRUPTS
        BSR MEMCLR          ; CLEAN UP MEMORY
;---------------------------------------------
MAIN:   SEI
        LDA #<6000
        STA SECNT.0
        STA NXTIM.0
        LDA #>6000
        STA SECNT.1
        STA NXTIM.1

LDA #07H            ; SET UP TIMER
        STA TCR
        LDA #70
        STA TDR

CLRA
        JSR FILDSP
        JSR DISPLAY
        JSR DSPHB

BRCLR 6,PORTC,CHKMOD    ; TEST MODE
        CLI                     ; ENABLE INTERRUPTS
        JMP PWRUP

CHKMOD: LDA #<200
        STA SECNT.0
        STA NXTIM.0
        LDA #>200
        STA SECNT.1
        STA NXTIM.1
        CLI

CHECK:  JSR READ0
        STA VSENS
        JSR READ1
        STA TEMP
        JSR PROCES

PAUSE:  BRCLR 0,FLAG0,PAUSE
        BCLR 0,FLAG0
        JMP CHECK

TESTJ1: JMP TEST
;---------------------------------------------

OC0:    LDA #<3000          ; SET UP TIMER FOR 90 SECONDS OF LOW CURRENT
```

```
           STA NXTIM.0
           LDA #>3000              ; <ACTUALLY 3 CYCLES OF 30 SECONDS>
           STA NXTIM.1
           BCLR 0,FLAG0
           BSET 5,PORTC            ; TURN ON HIGH CURRENT
           BSET 4,PORTC

BCLR 5,PORTA            ; CLEAR TEST LAMP
           JSR INDCTR              ; PROCESS PREVIOUSLY AQUIRED DATA
           JSR LCDDSP
           BRCLR 6,FLAG1,OCO1
           JSR ERRDSP

OCO1:      JSR BUTTON
           BCS TESTJ1
           JSR DMPCHK
           BRCLR 5,FLAG1,DSP1A
           JSR LCDDSP
DSP1A:     BRCLR 0,FLAG0,OCO1      ; HIGH CURRENT FOR 60 SECONDS
           LDX #HICHKI
           JSR CHKI

BCLR 5,PORTC
           BCLR 0,FLAG0            ; THEN LOW FOR 90

JSR LMPCHK
           JSR LEDCHK
           BRCLR 6,FLAG1,LOWC1
           JSR ERRDSP

LOWC1:     JSR BUTTON
           BCS TESTJ
           JSR DMPCHK
           BRCLR 5,FLAG1,DSP1B
           JSR LCDDSP
DSP1B:     BRCLR 0,FLAG0,LOWC1     ; FIRST 30 SECOND PERIOD
           BCLR 0,FLAG0

JSR TSTVS               ; TEST SENSOR VOLTAGE
LOWC2:     JSR BUTTON
           BCS TESTJ
           JSR DMPCHK
           BRCLR 5,FLAG1,DSP1C
           JSR LCDDSP
DSP1C:     BRCLR 0,FLAG0,LOWC2     ; SECOND 30 SECOND PERIOD
           BCLR 0,FLAG0
           JSR TSTVS               ; TEST SENSOR VOLTAGE

LDA #25
           STA NXTIM.0
           CLR NXTIM.1
OC1:       JSR BUTTON
           BCS TESTJ
           JSR DMPCHK
           BRCLR 5,FLAG1,DSP1D
           JSR LCDDSP
DSP1D:     BRCLR 0,FLAG0,OC1       ; 3RD AND FINAL 30 SECOND PERIOD
           LDX #LOCHKI
           JSR CHKI
                                   ; WAIT 25 MILLISECONDS
           BCLR 4,PORTC            ; WITH CURRENT OFF
           BCLR 0,FLAG0
           LDA #<6000
           STA NXTIM.0
           LDA #>6000
           STA NXTIM.1             ; SET UP TIMER FOR 60 SECONDS
OC1A:      BRCLR 0,FLAG0,OC1A      ; THEN SAMPLE
           JSR READ0
           STA VSENS
           JSR READ1
           STA TEMP
```

```
                BCLR 0,FLAG0
                BSET 5,PORTC            ; TURN ON HIGH CURRENT
                BSET 4,PORTC
                JSR GETCOC          ; GET CURRENT COC
                JSR HBCOC           ; COMPUTE BLOOD LEVEL
                JMP OCO

TESTJ:          JMP TEST
                PAGE
;----- PROCESS DATA HERE -------
ERRDJ:          JMP ERRDSP          ; jmp fixup PROCES:         JSR GETCOC          ; GET CURRENT COC
                JSR HBCOC           ; COMPUTE BLOOD LEVEL AND SET OUTPUTS
                JSR INDCTR
LCDDSP:         BRSET 6,FLAG1,ERRDJ
                BIL DSPCOC
DSPHB:          BRSET 6,FLAG1,ERRDJ
                LDA COHB1.0         ; Display current blood % CoC
                STA MATH.0
                LDA COHB1.1
                STA MATH.1
                LDA COHB1.2
                STA MATH.2
                LDA #100
                STA CONST.0
                CLR CONST.1
                CLR MATH.3
                LDX #CONST.0
                JSR DIVIDE          ; Set up value to xx.xx JSR BINBCD
                BCLR 7,FLAG1
                CLR WORK2
                LDA BCD1
                JSR LEFT
                ORA #80H
                STA DISBUF
                LDA BCD1
                BSET 7,FLAG1
                JSR RIGHT
                ORA #80H
                STA DISBUF+1
                LDA BCD0
                JSR LEFT
                BRA DSPC1
;               STA DISBUF+2
;               LDA BCD0
;               BRA DSPCOM
;               JSR RIGHT
;               STA DISBUF+3
;               CLR DISBUF+4
;               JSR DISPLAY
;               RTS DSPCOC:         BRSET 6,FLAG1,ERRDSP
                LDA COC1.0          ; Display current Co level (ambient)
                STA MATH.0
                LDA COC1.1
                STA MATH.1

JSR BINBCD
                BCLR 7,FLAG1
                CLR WORK2
                LDA BCD1
                JSR LEFT
                STA DISBUF
                LDA BCD1
                JSR RIGHT
                STA DISBUF+1
                LDA BCD0
```

```
        JSR LEFT
        ORA #80H
DSPC1:  STA DISBUF+2
        LDA BCDO
DSPCOM: BSET 7,FLAG1
        JSR RIGHT
        STA DISBUF+3
        CLR DISBUF+4
        JSR DISPLAY
        RTS

;----------------------------------------------------------------
ERRDSP: BCLR 6,FLAG1      ; ACKNOWLEDGE ERROR CODE
        LDA #3EH
        STA DISBUF
        LDA #30H
        STA DISBUF+1
        LDA #20
        STA WORK2
        LDA ERRCOD
        BCLR 7,FLAG1
        JSR LEFT
        STA DISBUF+2
        LDA ERRCOD
        BRA DSPCOM
;       BSET 7,FLAG1
;       JSR RIGHT
;       STA DISBUF+3
;       CLR DISBUF+4
;       JSR DISPLAY
;       RTS

;----------------------------------------------------------------
TSTVS:  BCLR 4,PORTC      ; TURN OFF CURRENT FOR 20 MILLISECONDS
        LDA #2
        STA TIMER
TSTVS1: LDA TIMER
        BNE TSTVS1
        LDA VSENS
        STA SAVE.0
        JSR READO
        BSET 4,PORTC      ; TURN CURRENT BACK ON
        STA VSENS
        JSR READ1
        STA TEMP
        JSR GETCOC
        LDA #239
        CMP COCIDX
        BHS VSOK
        LDA #25
        JSR CHKHB
        BCS OKHB1
        LDA #3
        STA COHB1.2
        LDA #0D0H
        STA COHB1.1
        LDA #090H
        STA COHB1.0
OKHB1:  BSET 3,FLAG1
        BSET 1,FLAG0
        JSR SHLEV
        LDA #40H          ; SET LED R2
        STA PORTB
        RTS

VSOK:   LDA SAVE.0        ; RESTORE OLD VSENS
        STA VSENS
        JSR GETCOC
        RTS

;----------------------------------------------------------------
```

```
;------------------------------------
HITEMP: INCX
; { SHOULD ALSO SET FAULT LAMP HERE }
        LDA #03H
        BRA BADTMP
LOTEMP: DECX
; { SHOULD ALSO SET FAULT LAMP HERE }
        LDA #04H
BADTMP: JSR SETFLT
        BRA OKTEMP

GETCOC: LDA TEMP        ; get temperature a/d value
        CLRX
CHKTAD: CMP TADTBL,X
        BLS TSTTAD
        INCX
        BRA CHKTAD
TSTTAD: CPX #0
        BEQ HITEMP
        CPX #22
        BHS LOTEMP
OKTEMP: DECX
        LSLX
        LDA TCTBL,X
        STA CF.1
        LDA TCTBL+1,X
        STA CF.0
GETRS:  LDA VSENS       ; normalize RS value
        LSLA            ; first do table lookup
        BCC LOWRS
        TAX
        LDA RSTBL+256,X
        STA MATH.1
        LDA RSTBL+257,X
        STA MATH.0
        BRA FIXRS
LOWRS:  TAX
        LDA RSTBL,X
        STA MATH.1
        LDA RSTBL+1,X
        STA MATH.0
FIXRS:
        LDA CF.0
        STA CONST.0
        LDA CF.1
        STA CONST.1
        LDX #CONST.0
        JSR MUL16       ; multiply 20 degree RS value by temp CF
        LDA #<10000
        STA CONST.0
        LDA #>10000
        STA CONST.1
        LDX #CONST.0
        JSR DIVIDE      ; scale result back to normal LDA #0
        STA WORK1                ; get index corresponding to normalized RS LDA MATH.2
        BNE GOTIDX               ; LARGE NUMBERS ARE FIRST IN RS TABLE 7/9/86
GETIDX: LDX WORK1
        LSLX
        BCS GIDXHI
        LDA MATH.1
        CMP RSTBL,X
        BLO NXTIDX
        BHI GOTIDX
        LDA MATH.0
        CMP RSTBL+1,X
        BHS GOTIDX
NXTIDX: INC WORK1
```

```
        BNE GETIDX
HIIDX:  LDA #0FFH
        STA WORK1
        BRA GOTIDX

GIDXHI: LDA MATH.1
        CMP RSTBL+256,X
        BLO NXTIDX
        BHI GOTIDX
        LDA MATH.0
        CMP RSTBL+257,X
        BLO NXTIDX

GOTIDX: LDA WORK1
        LDX WORK1
        STX COCIDX
        LSLX
        BCC LOWCOC
        LDA COCTBL+256,X
        STA COC1.1
        LDA COCTBL+257,X
        STA COC1.0
        BRA GOTCOC
LOWCOC: LDA COCTBL,X
        STA COC1.1
        LDA COCTBL+1,X
        STA COC1.0
GOTCOC: RTS

;----------------------------------------
HBCOC:
; Compute percentage CO in blood
        LDA COC1.0
        STA MATH.0      ; load current CO sensor into math regs
        LDA COC1.1
        STA MATH.1
        LDA #42
        STA WORK2
        JSR MULWK22     ; and multiply by .0042
        LDA MATH.0
        ADD #17         ; add .0017 to result
        STA CTMP.0      ; and save interim results
        LDA MATH.1
        ADC #0
        STA CTMP.1
        LDA MATH.2      ; 6/18/86 used to be math.3 -->bug
        ADC #0
        STA CTMP.2
;-- multiply old COHb by .9745 --
        LDA #<9745
        STA CONST.0
        LDA #>9745
        STA CONST.1
        LDA COHB1.0
        STA MATH.0
        STA COHB0.0

LDA COHB1.1
        STA MATH.1
        STA COHB0.1

LDA COHB1.2
        STA MATH.2
        STA COHB0.2

LDX #CONST.0
        JSR MUL23       ; perform multiplication

LDA #<10000
        STA CONST.0
        LDA #>10000
```

```
            STA  CONST.1
            LDX  #CONST.0
            JSR  DIV52          ; scale multiplication results back down LDA  MATH.0         ; save new COHb
            ADD  CTMP.0
            STA  COHB1.0
            LDA  MATH.1
            ADC  CTMP.1
            STA  COHB1.1
            LDA  MATH.2
            ADC  CTMP.2
            STA  COHB1.2
            RTS ;-----------------------------
INDCTR:     BRCLR 5,FLAG0,OKIND  ; NO INDICATORS DURING A FAULT
KILIND:     LDA  #0
            STA  PORTB
            LDA  PORTA
            AND  #0E2H           ; CLEAR LAMPS BUT NOT BUZZER
            STA  PORTA
            RTS                  ; AND BUG OUT ; determine led status
OKIND:      LDA  COCIDX
            STA  WORK1
LEDST:      LDX  #0
LEDST1:     LDA  #6
            STA  WORK3
            JSR  CHKLES
            LDA  WORK3
            TAX
            LDA  LEDTBL,X
            STA  PORTB ; compute hh status
            CLC                  ; READ DIPSWITCH SETTING
            CLRA
            BRCLR 7,PORTC,MAP1   ; Check ms bit
            SEC
MAP1:       ROLA
            BRCLR 7,PORTD,MAP2   ; 2nd ms bit
            SEC
MAP2:       ROLA
            BRCLR 7,PORTB,MAP3   ; 3rd ms bit
            SEC
MAP3:       ROLA
            BRCLR 7,PORTA,MAP4   ; And ls bit of switches
            SEC
MAP4:       ROLA
            ADD  A,#7
            JSR  CHKHB
            BCC  HHOFF
HHON:       BSET 3,FLAG1         ; ENABLE BUZZER (HEALTH HAZARD EXISTS)
            BRSET 1,FLAG0,LAMPS  ; SEE IF HEALTH HAZARD ALREADY EXISTS
            BCLR 2,FLAG0         ; NO PREVIOUS H/H. CLEAR H/H STATE
            BCLR 3,FLAG0
            BSET 1,FLAG0         ; Set Health Hazard flag
            BRA  LAMPS
HHOFF:      BCLR 3,FLAG1         ; DISABLE BUZZER
            BCLR 1,FLAG0         ; AND CLEAR H/H FLAG
            BRA  NOLMPJ
; Determine lamp status
LAMPS:      LDA  COHB1.0
            SUB  COHB0.0
            STA  CTMP.0
            LDA  COHB1.1
            SBC  COHB0.1
            STA  CTMP.1
            LDA  COHB1.2
```

```
                SBC COHBO.2
                STA CTMP.2
                BCS LLEV           ; IF CURRENT - LAST HB LEVEL IS (-) THEN LOW LEVEL
                LDX #LLVAL
                JSR CHKHH
                BCS LLEV
                LDX #MMVAL
                JSR CHKHH
                BCS MMLEV
SHLEV:          BSET 3,FLAG0
                BCLR 2,FLAG0
                LDA #SHLMP
                BRA SETLMP
MMLEV:          BRSET 3,FLAG0,SHLEV
;               BCLR 3,FLAG0
                BSET 2,FLAG0
                LDA #MMLMP
                BRA SETLMP
LLEV:           BRSET 3,FLAG0,SHLEV
                BRSET 2,FLAG0,MMLEV
;               BCLR 3,FLAG0
;               BCLR 2,FLAG0
                LDA #LLLMP
SETLMP:         BRSET 1,FLAG0,DOLMP
NOLMPJ:         LDA #NOLMP
DOLMP:          STA WORK1
                LDA PORTA
                AND #LMPMSK
                ORA WORK1
                STA PORTA          ; SET LAMP STATUS (BUZZER IS AUTOMATIC)

; Determine if current coc is above 100 ppm
                BRCLR 3,FLAG1,NOBUZZ
                LDA COC1.1
                CMP #>50           ;100
                BHI ENBUZZ
                BLO NOBUZZ
                LDA COC1.0
                CMP #<50           ;100
                BLO NOBUZZ
ENBUZZ:         BSET 4,FLAG0       ; ENABLE BUZZER OUTPUT
                RTS                ; AND RETURN
NOBUZZ:         BCLR 4,FLAG0       ; DISABLE BUZZER OUTPUT
                RTS                ; AND RETURN PAGE
;----------------------------------------------
; Analog to Digital Conversion Routines
;----------------------------------------------
READ0:          LDA #0             ; READ AD0
                BRA READAD
READ1:          LDA #1             ; READ AD1
                BRA READAD
READ2:          LDA #2             ; READ AD2
                BRA READAD
READ3:          LDA #3             ; READ AD3

READAD:         AND #03H           ; Read A/D channel selected by ACC
                STA ADCON          ; Write selection to A/D control register,
WAITAD:         BRCLR 7,ADCON,WAITAD   ; And await completion.
                LDA ADREG          ; retreive results
                RTS                ; and return.

;----------------------------------------------
CHKHB:          STA WORK2
                LDA #10H
                STA MATH.0
                LDA #27H
                STA MATH.1
                JSR MULWK22        ; multiply 1 percent by set point
                LDA MATH.2
```

```
         CMP  COHB1.2        ; COMPARE INDEXED VALUE AGAINST CURRENT BLOOD LEVEL
         BHI  HHO1FF         ; AND IF INDEXED VALUE IS GREATER, NO HEALTH HAZARD
         BLO  HH1ON
         LDA  MATH.1
         CMP  COHB1.1
         BHI  HHO1FF
         BLO  HH1ON
         LDA  MATH.0
         CMP  COHB1.0
         BHI  HHO1FF
HH1ON:   SEC
         RTS
HHO1FF:  CLC
         RTS

;----------------------------------------
CHKLES:  LDA  CMPTBL,X
         CMP  WORK1
         BLO  LOOK1
GLOOK:   RTS
LOOK1:   INCX
         DEC  WORK3
         BNE  CHKLES
         RTS

CHKHH:   LDA  CTMP.2
         CMP  ,X
         BLO  CHKH1
         BHI  CHKH2
         LDA  CTMP.1
         CMP  1,X
         BLO  CHKH1
         BHI  CHKH2
         LDA  CTMP.0
         CMP  2,X
         BLO  CHKH1
CHKH2:   CLC
         RTS
CHKH1:   SEC
         RTS
CMPTBL:  DB   49
         DB   82
         DB   125
         DB   167
         DB   201
         DB   224
         DB   255

LEDTBL:  DB   40H, 20H, 10H, 08H, 04H, 02H, 01H

;ELTBL:  DB   001H, 011H, 070H    ;  7 %
;        DB   001H, 038H, 080H    ;  8 %
;        DB   001H, 05FH, 090H    ;  9 %
;        DB   001H, 086H, 0A0H    ; 10 %
;        DB   001H, 0ADH, 0B0H    ; 11 %
;        DB   001H, 0D4H, 0C0H    ; 12 %
;        DB   001H, 0FBH, 0D0H    ; 13 %
;        DB   002H, 022H, 0E0H    ; 14 %
;        DB   002H, 049H, 0F0H    ; 15 %
;        DB   002H, 071H, 000H    ; 16 %
;        DB   002H, 098H, 010H    ; 17 %
;        DB   002H, 0BFH, 020H    ; 18 %
;        DB   002H, 0E6H, 030H    ; 19 %
;        DB   003H, 00DH, 040H    ; 20 %
;        DB   003H, 034H, 050H    ; 21 %
;        DB   003H, 05BH, 060H    ; 22 %
;
;HB25:   DB   003H, 0D0H, 090H    ; %COHB = 25.00
         PAGE
;----------------------------------------
```

```
BINBCD:  LDX #16          ; number of binary bits to be converted
         LDA #0
         STA BCD0
         STA BCD1         ; PRESET BCD REGISTERS TO ZERO
         STA BCD2
BINB1:   CLC
         ROL MATH.0
         ROL MATH.1       ; rotate binary ms digit into carry
         LDA BCD0         ; add bcd digits to themselves ( bcd x 2)
         ADC BCD0         ; with carry from binary digits
         JSR DAA          ; decimal adjust result
         STA BCD0         ; and store.
         LDA BCD1         ; repeat for ms bcd digit
         ADC BCD1
         JSR DAA
         STA BCD1
         BCC BINB2
         LDA #99H         ; on overflow set bcd to 9999
         STA BCD0
         STA BCD1
         RTS
;        LDA #05H         ; error 5 no longer exists
;        JSR SETFLT
BINB2:   DECX
         BNE BINB1        ; REPEAT UNTIL ALL 24 BITS ARE DONE
         RTS ;-------------------------------------------------
; DAA - DECIMAL ADJUST ACCUMULATOR
;-------------------------------------------------
; AT ENTRY
; A  --  RESULT OF PREVIOUS ADD OR ADC
; CC --  RESULT OF PREVIOUS ADD OR ADC
; AT EXIT
; A  --  CORRECTED BCD NUMBERS
; CC --  CARRY BIT READY FOR MULTIPLE BYTE PRECISION ARITHMETIC DAA:     BCS DAAHAI       ; IF CARRY THEN ADJUST HIGH DIGIT
         CMP #99H         ; DOUBLE OVERFLOW? (>99?)
         BLS DAALOW       ; NO, CHECK LOW DIGIT
DAAHAI:  NEGA             ; AVOID CLOBBERING H-BIT BY
         SUB #60H         ; A + $60 = -(-A - $60)
         NEGA
; THIS LAST ADJUSTMENT MEANS RETURN WITH CARRY SET
         BSR DAALOW
         SEC
         RTS
; CHECK LOW DIGIT FOR OVERFLOW
DAALOW:  BHCC DAANOO      ; NO OVERFLOW DETECTED
         ADD #6           ; ADJUST FOR KNOWN OVERFLOW
         RTS
DAANOO:  ADD #6           ; LOW DIGIT A-F?
         BHCS DAARTS      ; BRANCH ADJUSTED IF CORRECT ASSUMPTION
         SUB #6
DAARTS:  RTS              ; TAH DAH!

;--------------------------------------------------------------------
DMPCHK:  BRSET 1,PORTC,NDMP
         BCLR 4,PORTC             ; KILL i DURING DATA DUMP
         JSR CLRDLY
         BRCLR 1,PORTC,RJ
         JSR MEMCLR
RJ:      JSR DUMP
NDMP:    RTS

;--------------------------------------------------------------------
BUTTON:  CLR TBUTT        ; CLEAR BUTTON PRESS RECORDER
         BRCLR 6,PORTD,BDWN
NOBUTT:  CLR BTIMER
         CLC
         RTS
```

```
BDWN:    LDA #250
         STA BTIMER
         BCLR 1,PORTA     ; KILL ANY BUZZ IN PROGRESS
BDWNA:   LDA #2
         STA TIMER        ; USE A 20 MILLISECOND SWITCH DEBOUNCE
BDWN1:   BRSET 6,PORTD,BDWN4
         LDA TIMER
         BNE BDWN1
         BSET 1,PORTA     ; BEEP TO ACKNOWLEDGE
         LDA #5
         STA TIMER
BDWN2:   LDA TIMER
         BNE BDWN2
         BCLR 1,PORTA
BDWN3:   LDA BTIMER
         BEQ TIMOUT
         BRCLR 6,PORTD,BDWN3   ; AWAIT SWITCH RELEASE
         LDA #2
         STA TIMER
BDWN3A:  BRCLR 6,PORTD,BDWN3   ; ENSURE SWITCH RELEASED FOR 20 MILLISECONDS
         LDA TIMER
         BNE BDWN3A
         INC TBUTT
BDWN4:   LDA BTIMER
         BEQ TIMOUT
         BRSET 6,PORTD,BDWN4
         BRA BDWNA
TIMOUT:  BCLR 5,PORTC
         BCLR 4,PORTC
         LDA TBUTT
         BEQ BFAULT
         BSET 7,FLAG0
         CMP #4
         BLO FIXB1
         LDA #4
         BRA FIXB2
FIXB1:   CMP #2
         BLO FIXB2
         LDA #2
         BRA FIXB2
FIXB2:   STA TBUTT
         STA WORK1
         LDA #250
         STA BTIMER
TBUZZ:   LDA #5
         STA TIMER
         BSET 1,PORTA
TBUZZ1:  LDA TIMER
         BNE TBUZZ1
         BCLR 1,PORTA
         LDA #5
         STA TIMER
TBUZZ2:  LDA TIMER
         BNE TBUZZ2
         DEC WORK1
         BNE TBUZZ
BOUT:    BRCLR 5,FLAG0,BOUT1
         JSR ERRDSP       ; REDISPLAY ERROR MESSAGE
BOUT1:   CLR LOFF.1
         LDA #1
         STA LOFF.0
         CLR BTIMER
         SEC
         RTS
BFAULT:
         LDA #06H
         JSR SETFLT
         BRA BOUT
         PAGE
; MUL16 IS A 2 BYTE BY 2 BYTE MULTIPLY
; MUL23 IS A 2 BY THREE BYTE MULTIPLY
```

```
; ON ENTRY, MULTIPLIER IS IN MATH.0-MATH.1 (MATH.0-MATH.2 FOR MUL23), X POINTS
; TO MULTIPLICAND
; ON EXIT, 5 BYTE RESULT IS IN MATH.0-MATH.4, LS TO MS

MUL16:    CLR MATH.2
MUL23:    CLR MATH.3
MUL24:    LDA #33
          STA WORK1
          CLR MATH.4
          CLR MATH.5
          CLC
          BRA ROT1
NXT:      BCC ROTAT
          LDA MATH.4
          ADD ,X
          STA MATH.4
          LDA MATH.5
          ADC 1,X
          STA MATH.5

ROTAT:    ROR MATH.5
          ROR MATH.4
ROT1:     ROR MATH.3
          ROR MATH.2
          ROR MATH.1
          ROR MATH.0
          DEC WORK1
          BNE NXT
          RTS

;--------------------------------
; MULWK2 MULTIPLIES MATH.0-MATH.3 BY WORK2 ( A 4 BY 1 BYTE MULTIPLY )
MULWK21:
          CLR MATH.1      ; 1 X 1
MULWK22:
          CLR MATH.2      ; 2 X 1
MULWK23:
          CLR MATH.3      ; 1 X 1
MULWK2:   LDA #33
          STA WORK1
          CLR MATH.4
          CLC
          BRA MLWK2C
MLWK2A:   BCC MLWK2B
          LDA WORK2
          ADD MATH.4
          STA MATH.4
MLWK2B:   ROR MATH.4
MLWK2C:   ROR MATH.3
          ROR MATH.2
          ROR MATH.1
          ROR MATH.0
          DEC WORK1
          BNE MLWK2A
          RTS

;--------------------------------
; DIVIDE IS A 4 BYTE BY 2 BYTE DIVIDE ROUTINE
; DIV52 IS A 5 BY 2 BYTE DIVIDE
; ON ENTRY, MATH.0-MATH.4 CONTAINS DIVIDEND, X POINTS TO 2 BYTE DIVISOR
; ON EXIT, QUOTIENT IS IN MATH.0-MATH.4, REMAINDER IN MATH.4-MATH.5

DIVIDE:   CLR MATH.4
DIV52:    LDA #41
          STA WORK1
          CLR MATH.5
          CLR MATH.6
DIVA:     DEC WORK1
          BNE DIVB
          RTS
```

```
DIVB:   LSL MATH.0
        ROL MATH.1
        ROL MATH.2
        ROL MATH.3
        ROL MATH.4
        ROL MATH.5
        ROL MATH.6
        BCS DIVC
        LDA MATH.5
        SUB ,X
        LDA MATH.6
        SBC 1,X
        BCS DIVA
DIVC:   LDA MATH.5
        SUB ,X
        STA MATH.5
        LDA MATH.6
        SBC 1,X
        STA MATH.6
        INC MATH.0
        BRA DIVA
;--------------------------------
        PAGE
;--------------------------------
TIMINT: LDA #70
        STA TDR
        BCLR 7,TCR

;-------- ADDED TO MAKE DISPLAY UPDATES MORE RESPONSIVE -----------
        BIL CHKLO              ; check status of display switch
        BRSET 6,FLAG0,NOCHNG   ; if old = current, no change
        DEC DSPBNC             ; check debounce timer
        BNE SWTEXT             ; if not zero, wait and see
        BSET 6,FLAG0           ; New display
        BSET 5,FLAG1
        BRA NOCHNG
CHKLO:  BRCLR 6,FLAG0,NOCHNG   ; Do same thing for low input
        DEC DSPBNC
        BNE SWTEXT
        BCLR 6,FLAG0
        BSET 5,FLAG1
NOCHNG: LDA #4
        STA DSPBNC
SWTEXT:

;------------------------------------------------------------------
        LDA TIMER
        BEQ TIME
        DEC TIMER
TIME:   LDA TIME.0
        BEQ TIMEA
        DEC TIME.0
TIMEA:
BUZZZ:  BRCLR 2,FLAG1,BUZZ3    ; Buzzer is currently off
BUZZ1:  LDA LBUZZ
        BEQ BUZZ2              ; BUZZ TIMER ELAPSED?
        DEC LBUZZ
        BSET 2,FLAG1
        BRA UPDATE BUZZ2:  BRCLR 5,FLAG0,HHBUZZ
;++++++++ TEST ONLY +++++++++
        BRCLR 3,PORTC,HHBUZZ   ; DISABLE FAULT BUZZER BY SWITCH
;++++++++ TEST ONLY +++++++++
        LDX #0                 ; FAULT BUZZER
        BRA BUZZ2A
HHBUZZ: BRCLR 4,FLAG0,KILBUZ
        BRCLR 1,FLAG0,KILBUZ
        BRCLR 2,FLAG0,SHCHK
        LDX #3                 ; MM BUZZER
        BRA BUZZ2A
```

```
SHCHK:    BRSET 3,FLAG0,SHBUZZ
          LDX #6                        ; LL BUZZER
          BRA BUZZ2A
SHBUZZ:   LDX #9                        ; SH BUZZER
          BRA BUZZ2A
KILBUZ:   LDX #12                       ; NO BUZZER
BUZZ2A:   LDA BUZTBL,X
          STA LBUZZ
          LDA BUZTBL+1,X
          STA LOFF.1
          LDA BUZTBL+2,X
          STA LOFF.0
BUZZ3:    LDA LOFF.0
          SUB #1
          STA LOFF.0
          LDA LOFF.1
          SBC #0
          STA LOFF.1
          BCS BUZZ1
          BCLR 2,FLAG1

UPDATE:   BRSET 7,FLAG0,UPDAT2          ; NO BUZZER IN TEST MODE
          LDA BTIMER
          BEQ UPDAT
          DEC BTIMER
          BRA UPDAT2
UPDAT:    BRSET 2,FLAG1,UPDAT1
          BCLR 1,PORTA
          BRA UPDAT2
UPDAT1:   BSET 1,PORTA
UPDAT2:   LDA SECNT.0                   ; CHECK UPDATE TIMER
          SUB #1
          STA SECNT.0
          LDA SECNT.1
          SBC #0
          STA SECNT.1
          BCS NEWTIM
          RTI
NEWTIM:
          BSET 0,FLAG0                  ; UPDATE DISPLAY
          LDA NXTIM.0
          STA SECNT.0
          LDA NXTIM.1
          STA SECNT.1
BAIL:     RTI                           ; AND RETURN FORM INTERRUPT

;--------------------------
BUZTBL:   DB 064H, 000H, 064H           ; FAULT BUZZER VALUES
          DB 064H, 001H, 090H           ; MM BUZZER VALUES
          DB 064H, 003H, 084H           ; LL BUZZER VALUES
          DB 064H, 000H, 000H           ; SH BUZZER VALUES
          DB 000H, 000H, 064H           ; NO BUZZER VALUES
;--------------------------
          PAGE
TTOG:     LDA #50                       ; TOGGLE TEST LAMP
          STA TIMER
          BRCLR 5,PORTA,TTOG1
          BCLR 5,PORTA
          RTS
TTOG1:    BSET 5,PORTA
          RTS

;--------------------------
TFAULT:   BSR SETFLT
          JMP TWAT

;--------------------------
SETFLT:   BSET 6,PORTA                  ; SET FAULT LAMP
          BSET 5,FLAG0                  ; AND FAULT FLAG
          STA ERRCOD
          BSET 6,FLAG1                  ; SET FAULT DISPLAY INDICATOR
```

```
            BSET 5,FLAG1      ; REQUEST DISPLAY UPDATE
            JSR KILIND        ; KILL INDICATORS
            RTS

;------------------------
PWRUP:  SEI     ; KILL TIMER
            BSET 7,FLAG0
            BCLR 5,FLAG0      ; KILL FAULT BIT
            BCLR 4,PORTC      ; KILL SENSOR CURRENT
            LDA #0
            STA PORTA         ; AND LAMPS
            STA PORTB         ; AND BUZZERS
            LDA #<500
            STA SECNT.0
            LDA #>500
            STA SECNT.1
            LDA #<6000
            STA NXTIM.0
            LDA #>6000
            STA NXTIM.1
            CLI

JSR READ2
            CMP #0FEH
            LDA #07H
            BLO TFAULT
            JSR READ3
            CMP #1
            LDA #08H
            BHI TFAULT
            JSR READ1
            CMP #60
            LDA #09H
            BLO TFAULT
            CMP #225
            LDA #10H
            BHI TFAULT
TWAT:   LDA TIMER
            BNE TWAT1
            JSR TTOG
TWAT1:  BRCLR 0,FLAG0,TWAT
            BCLR 0,FLAG0

PWROUT: BCLR 7,FLAG0
            BSET 5,PORTA      ; SET TEST LAMP
            JSR ICYCLE
            BCLR 5,PORTA      ; CLEAR TEST LAMP
            JSR GETCOC
            JSR HBCOC
            JMP OCO

;------------------------
            PAGE
;------------------------
EOS:
EOS1:   BRCLR 0,FLAG0,EOS
            BCLR 0,FLAG0
            RTS

;------------------------
LEDCHK: JSR READ2
            CMP #MAXLED
            BHI BLED
            CMP #MINLED
            BLO BLED
GLED:   RTS
BLED:   LDA PORTB
            AND #7FH
            BEQ GLED
            LDA #11H
```

```
        JMP SETFLT          ; BAD LED

;------------------------
LMPCHK:  LDA #7
         STA WORK1
         CLRX
         CLR WORK3
         CLR WORK4
         LDA PORTA
LMPC1:   RORA
         BCC LMPC2
         STA WORK2          ; SAVE ACC
         LDA ILMP,X
         ADD WORK3          ; ADD IN APPROPRIATE MIN CURRENT
         STA WORK3
         LDA ILMP+1,X
         ADD WORK4          ; ADD IN APPROPRIATE MAX CURRENT
         STA WORK4
         LDA WORK2          ; RESTORE ACC
LMPC2:   INCX
         INCX
         DEC WORK1
         BNE LMPC1
         JSR READ3          ; READ IN ACTUAL LAMP CURRENT
         CMP WORK3          ; COMPARE AGAINST MIN
         BLO BLMP1          ; IF LOW, NO GOOD
         CMP WORK4          ; COMPARE AGAINST MAX
         BHI BLMP2          ; IF HIGH, NO GOOD
         RTS

BLMP1:   LDA #12H
         JMP SETFLT
BLMP2:   LDA #13H
         JMP SETFLT

;lamp i    min max  lamp
ILMP:    DB  6, 16  ; health hazard
         DB  1,  4  ; buzzer
         DB  3,  8  ; fault
         DB  3,  8  ; test
         DB  3,  8  ; short exposure
         DB  3,  8  ; medium exposure
         DB  3,  8  ; long exposure

;------------------------
TFON:    JSR SETFLT
         JMP TWAIT

;------------------------
TEST:    SEI                ; KILL TIMER
         BSET 7,FLAG0
         BCLR 5,FLAG0       ; KILL FAULT BIT
         BCLR 4,PORTC       ; KILL SENSOR CURRENT
         LDA #0
         STA PORTA          ; AND LAMPS
         STA PORTB          ; AND BUZZERS
         LDA #<100
         STA SECNT.0
         STA NXTIM.0
         LDA #>100
         STA SECNT.1
         STA NXTIM.1
         CLI

JSR READ2
         CMP #0FEH
         LDA #07H
         BLO TFON
         JSR READ3
         CMP #1
```

```
                LDA  #08H
                BHI  TFON
                JSR  READ1
                STA  20H            ; SAVE TCV
                CMP  #60
                LDA  #09H
                BLO  TFON
                CMP  #225
                LDA  #10H
                BHI  TFON
TWAIT:          CLR  STATE
                JSR  EOS
STAT:           LDX  STATE
                LDA  STATBL,X
                STA  PORTA
                LDA  STATBL+1,X
                STA  PORTB
                JSR  EOS
                JSR  LEDCHK
                JSR  LMPCHK
                JSR  PROCHK         ; SAVE A/D DATA FOR PROD. TESTING
                INC  STATE
                INC  STATE
                LDA  STATE
                CMP  #32
                BLO  STAT

CLR  PORTA
                CLR  PORTB
                BRCLR 5,FLAG0,OKDISP
                BSET 6,PORTA        ; SET ERROR LAMP
OKDISP:         LDA  #<6000
                STA  NXTIM.0
                LDA  #>6000
                STA  NXTIM.1
                JSR  EOS

LDA  TBUTT
                CMP  #1
                BHI  TEST2
TSTOVR:         BCLR 7,FLAG0        ; CLEAR TEST FLAG
                CLR  TBUTT
                JMP  OC0
TEST2:          CMP  #3
                BHI  TEST4
                JSR  CLEAR          ; CLEAR MEMORY
                CLR  TBUTT
                JMP  PWROUT
;               BRA  TSTOVR

TEST4:          BSET 5,PORTA        ; SET TEST MODE FLAGS
                BCLR 7,FLAG0
                JSR  CLEAR
                JSR  ICYCLE
                BCLR 0,FLAG0
                BSET 5,PORTC        ; TURN ON HIGH CURRENT
                BSET 4,PORTC

JSR  GETCOC

LDA  COC1.0
                STA  MATH.0
                LDA  COC1.1
                STA  MATH.1
                LDA  #10
                STA  WORK2
                JSR  MULWK22        ; MULTIPLY COC BY 10

LDA  MATH.0
                STA  COC1.0
                LDA  MATH.1
                STA  COC1.1
```

```
;++++++++++++++++++++++++
        LDA MATH.2
        BNE IDXOVR              ; get index corresponding to new CoC value LDA #0
        STA WORK1
FNDIDX: LDX WORK1
        LSLX
        BCS FIDXHI
        LDA MATH.1
        CMP COCTBL,X
        BHI IDXNXT
        BLO GIDX10
        LDA MATH.0
        CMP COCTBL+1,X
        BLS GIDX10
IDXNXT: INC WORK1
        BNE FNDIDX
IDXOVR: LDA #0FFH
        STA WORK1
        LDA #0FFH
        STA COC1.0
        STA COC1.1
        BRA GIDX10

FIDXHI: LDA MATH.1
        CMP COCTBL+256,X
        BHI IDXNXT
        BLO GIDX10
        LDA MATH.0
        CMP COCTBL+257,X
        BHI IDXNXT

GIDX10: LDA WORK1
        STA COCIDX
;++++++++++++++++++++++++
        JSR HBCOC               ; AND PROCESS ACCORDINGLY
        JSR INDCTR
        JSR LCDDSP
        JSR ICYCLE
        JSR CLEAR
        BCLR 7,FLAG0
        BCLR 5,PORTA            ; CLEAR TEST LAMP
        JSR GETCOC
        JSR HBCOC
        JMP TSTOVR

;------------------------
ICYCLE:
TAC0:   LDA #<3000              ; SET UP TIMER FOR 90 SECONDS OF LOW CURRENT
        STA NXTIM.0
        LDA #>3000              ; <ACTUALLY 3 CYCLES OF 30 SECONDS>
        STA NXTIM.1
        BCLR 0,FLAG0
        BSET 5,PORTC            ; TURN ON HIGH CURRENT
        BSET 4,PORTC
TAC01:  JSR DMPCHK
        BRCLR 5,FLAG1,DSP1E
        JSR LCDDSP
DSP1E:
TWAIT2: BRCLR 0,FLAG0,TAC01     ; HIGH CURRENT FOR 60 SECONDS
        JSR READ0
        STA 10H                 ; SAVE HI i FOR PROD TEST
        LDX #HICHKI
        JSR CHKI
        BCLR 5,PORTC
        BCLR 0,FLAG0            ; THEN LOW FOR 90
        JSR LOW21

JSR READ0
```

```
                STA 11H                 ; SAVE LOW i FOR PROD TEST
                LDX #LOCHKI
                JSR CHKI

JSR TSTVS               ; TEST SENSOR VOLTAGE

JSR LOW21
;LOW23:
;               JSR DMPCHK
;               BRCLR 5,FLAG1,DSP1G
;               JSR LCDDSP
;DSP1G:
;LOW24:         BRCLR 0,FLAG0,LOW23     ; SECOND 30 SECOND PERIOD
;               BCLR 0,FLAG0

JSR TSTVS               ; TEST SENSOR VOLTAGE
LOW25:          LDA #25
                STA NXTIM.0
                CLR NXTIM.1
                JSR LOW21
;TAC1:
;               JSR DMPCHK
;               BRCLR 5,FLAG1,DSP1H
;               JSR LCDDSP
DSP1H:
;TWAIT3:        BRCLR 0,FLAG0,TAC1      ; 3RD AND FINAL 30 SECOND PERIOD.
                                        ; WAIT 25 MILLISECONDS
                BCLR 4,PORTC            ; WITH CURRENT OFF
                BCLR 0,FLAG0
                LDA #<6000
                STA NXTIM.0
                LDA #>6000
                STA NXTIM.1             ; SET UP TIMER FOR 60 SECONDS
TAC1A:          BRCLR 0,FLAG0,TAC1A     ; THEN SAMPLE
                BCLR 0,FLAG0
; READ A/D VALUES
                JSR READ0
                STA VSENS
                STA 21H                 ; SAVE Vs
                JSR READ1
                STA TEMP

RTS
;----------------------
LOW21:
                JSR DMPCHK
                BRCLR 5,FLAG1,DSP1F
                JSR LCDDSP
DSP1F:
LOW22:          BRCLR 0,FLAG0,LOW21     ; FIRST 30 SECOND PERIOD
                BCLR 0,FLAG0
                RTS

;--------------------------
CLEAR:          CLR COCHB
                CLR COHB0.0
                CLR COHB0.1
                CLR COHB0.2
                CLR COHB1.0
                CLR COHB1.1
                CLR COHB1.2

SEI
                LDA FLAG0
                AND #0E1H
                STA FLAG0

LDA #64H
                CLR LBUZZ
                CLR LOFF.1
                STA LOFF.0
                CLI
```

```
        CLR COC1.0
        CLR COC1.1
        CLR COCIDX

;       CLR CF.0
;       CLR CF.1

RTS

;-------------------
;          PORTA   PORTB
STATBL:
        DB 20H,    00H
        DB 02H,    00H
        DB 20H,    01H
        DB 00H,    01H
        DB 21H,    02H
        DB 01H,    02H
        DB 24H,    04H
        DB 04H,    04H
        DB 28H,    08H
        DB 08H,    08H
        DB 30H,    10H
        DB 10H,    10H
        DB 20H,    20H
        DB 00H,    20H
        DB 60H,    40H
        DB 40H,    40H
        DB 00H,    00H
        PAGE
;-------------------
PROCHK: LDX STATE                ; PRODUCTION TEST MODE STATUS CHK
        LSRX
        LDA TLATBL,X
        TAX
        JSR READ3
        STA 0,X
CHKLEDS:
        LDX STATE
        LSRX
        LDA LDATBL,X
        TAX
        JSR READ2
        STA 0,X
PROVR:  RTS

;-------------------
;TLTBL: DB 0,1,0,0,0,1,0,1
;       DB 0,1,0,1,1,0,0,1
;       DB 0
;LDTBL: DB 0,0,0,1,0,1,0,1
;       DB 0,1,0,1,1,0,0,1
;       DB 0

TLATBL: DB 28H, 19H, 28H, 28H, 28H, 1AH, 28H, 1BH
        DB 28H, 1CH, 28H, 1DH, 1EH, 28H, 28H, 1FH
        DB 28H

LDATBL: DB 28H, 28H, 28H, 12H, 28H, 13H, 28H, 14H
        DB 28H, 15H, 28H, 16H, 17H, 28H, 28H, 18H
        DB 28H
        PAGE
;-------------------
DISPLAY:
        BSR DISCLR          ; clear display
        LDA #80H
        LDX #1
        BSR DIS1            ; SEND START BIT
        LDX #0              ; prepare index to send 5 digits
DISCHR: LDA DISBUF,X
        BSR DISPLY
```

```
        INCX
        CPX #5
        BNE DISCHR
        RTS

;-----------------------
; DISPLY OUTPUTS THE ACCUMULATOR CONTENTS TO THE DISPLAY DRIVER

DISPLY: STX WORK1       ; save index
        LDX #8
DIS1:   BCLR 2,PORTC    ; clear data line
        ASLA
        BCC DIS2
        BSET 2,PORTC    ; set data line if data bit is a 1
DIS2:   BSET 0,PORTC    ; set display clock line
        NOP
        BCLR 0,PORTC    ; then drop it
        DECX
        BNE DIS1        ; check for all bits sent
        LDX WORK1       ; restore index
        BCLR 2,PORTC    ; clear data line
        RTS ;-----------------------
;       DISCLR CLEARS THE DISPLAY BUFFER ON THE 5453. IT WILL MOST LIKELY
;       not CLEAR THE DISPLAY DISCLR: STX WORK1
        BCLR 2,PORTC    ; clear display data line
        LDX #36
DISC1:  BSET 0,PORTC    ; raise dispay clock line
        NOP
        BCLR 0,PORTC    ; then lower it
        DECX
        BNE DISC1
        RTS ;-----------------------
FILDSP: LDX #DISBUF
FILDA:  STA ,X
        INCX
        CPX #(DISBUF+5)
        BNE FILDA
        RTS ;-----------------------
LEFT:   LSRA
        LSRA
        LSRA
        LSRA
RIGHT:  AND #0FH
        BNE RIGHTA
        BRCLR 7,FLAG1,RIGHTB
RIGHTA: BSET 7,FLAG1
        STX WORK1
        ADD WORK2       ; ADD DIGIT INDEX
        TAX
        LDA WORK2
        ADD #10         ; INCREMENT DIGIT INDEX TO NEXT SEGMENT MAP
        STA WORK2
        LDA SEGTBL,X
        LDX WORK1
        RTS
; RETURN A 0 (BLANK DIGIT)
RIGHTB: LDA WORK2
        ADD #10         ; INCREMENT DIGIT INDEX TO NEXT SEGMENT MAP
        STA WORK2
        CLRA
        RTS

;-----------------------
```

```
        PAGE
;------------------------
DUMP:   LDX #61H
DUMP1:  LDA O,X
        BSR DMPBYT
        DECX
        BNE DUMP1
        RTS

;------------------------
DMPBYT: STX WORK1       ; save index
        LDX #8
DMPB1:  BCLR 2,PORTC
        ASLA
        BCC DMPB2
        BSET 2,PORTC
DMPB2:  BSR TIMDLY
        BSET 0,PORTC
        BSR TIMDLY
        BCLR 0,PORTC
        BSR TIMDLY
        DECX
        BNE DMPB1
        LDX WORK1       ; retrieve index
        RTS ;------------------------
TIMDLY: STA WORK2
        CLR TIMDL1
        LDA #4          ; was 12
        STA TIMDL2
TD1:    DEC TIMDL1
        BNE TD1
        DEC TIMDL2
        BNE TD1
        LDA WORK2
        RTS
;------------------------
CLRDLY: STA WORK2
        CLR TIMDL1
        LDA #24         ; was 12
        STA TIMDL2
        BRA TD1
;------------------------
CHKI:   JSR READO
        CMP ,X
        BLO BADI
        CMP 1,X
        BLS OKI
BADI:   LDA #15H        ; SENSOR CURRENT FAULT
        JMP SETFLT
OKI:    RTS ;------------------------
        PAGE
;------------------------------------------------------------
; TC values are multiplied by 10,000 to preserve accurracy
TCTBL:  DW 14493, 14286, 14085, 13889
        DW 13514, 12987, 12658, 12195
        DW 11765, 10870, 10000,  9524
        DW  8696,  8000,  7407,  6897
        DW  6061,  5405,  4878,  4444
        DW  4000

;------------------------------------------------------------
RSTBL:  DW OFFFFH, OFFFFH, OFFFFH, OFFFFH
        DW 55889, 45545, 38385, 33133
        DW 29118, 25947, 23381, 21261
        DW 19480, 17963, 16655, 15516
        DW 14515, 13629, 12838, 12128
        DW 11488, 10907, 10378,  9894
```

```
        DW 9449, 9039, 8660, 8309
        DW 7982, 7678, 7393, 7127
        DW 6877, 6642, 6420, 6211
        DW 6014, 5827, 5649, 5481
        DW 5321, 5169, 5024, 4885
        DW 4753, 4626, 4505, 4389
        DW 4278, 4172, 4069, 3971
        DW 3876, 3785, 3697, 3613
        DW 3531, 3452, 3376, 3303
        DW 3231, 3162, 3096, 3031
        DW 2969, 2908, 2850, 2793
        DW 2737, 2683, 2631, 2580
        DW 2531, 2483, 2436, 2391
        DW 2346, 2303, 2261, 2220
        DW 2180, 2141, 2103, 2066
        DW 2030, 1994, 1959, 1926
        DW 1893, 1860, 1829, 1798
        DW 1768, 1738, 1709, 1681
        DW 1653, 1626, 1599, 1573
        DW 1547, 1522, 1498, 1473
        DW 1449, 1426, 1404, 1381
        DW 1359, 1337, 1316, 1295
        DW 1275, 1255, 1235, 1216
        DW 1197, 1178, 1160, 1142
        DW 1124, 1106, 1089, 1072
        DW 1056, 1039, 1023, 1007
        DW 992, 976, 961, 946
        DW 932, 917, 903, 889
        DW 875, 861, 848, 835
        DW 822, 809, 796, 784
        DW 771, 759, 747, 735
        DW 723, 712, 700, 689
        DW 678, 667, 656, 646
        DW 635, 625, 615, 605
        DW 595, 585, 575, 565
        DW 556, 546, 537, 528
        DW 519, 510, 501, 492
        DW 484, 475, 467, 458
        DW 450, 442, 434, 426
        DW 418, 410, 402, 395
        DW 387, 380, 372, 365
        DW 358, 350, 343, 336
        DW 329, 322, 316, 309
        DW 302, 296, 289, 283
        DW 276, 270, 264, 257
        DW 251, 245, 239, 233
        DW 227, 221, 216, 210
        DW 204, 199, 193, 187
        DW 182, 177, 171, 166
        DW 160, 155, 150, 145
        DW 140, 135, 130, 125
        DW 120, 115, 110, 105
        DW 101, 96, 91, 87
        DW 82, 77, 73, 68
        DW 64, 60, 55, 51
        DW 47, 42, 38, 34
        DW 30, 26, 21, 17
        DW 13, 9, 5, 1
;-------------------------------------------------------------------------
COCTBL: DW 0, 0, 0, 0
        DW 0, 0, 0, 10
        DW 10, 10, 10, 10
        DW 10, 10, 10, 10
        DW 10, 10, 10, 10
        DW 20, 20, 20, 20
        DW 20, 20, 20, 20
        DW 20, 20, 20, 30
        DW 30, 30, 30, 30
        DW 30, 30, 30, 30
        DW 30, 40, 40, 40
        DW 40, 40, 40, 40
        DW 40, 40, 50, 50
```

```
            DW 50, 50, 50, 50
            DW 50, 50, 60, 60
            DW 60, 60, 60, 60
            DW 60, 70, 70, 70
            DW 70, 70, 70, 70
            DW 80, 80, 80, 80
            DW 80, 80, 90, 90
            DW 90, 90, 90, 90
            DW 100, 100, 100, 100
            DW 100, 100, 110, 110
            DW 110, 110, 110, 120
            DW 120, 120, 120, 120
            DW 130, 130, 130, 130
            DW 140, 140, 140, 140
            DW 150, 150, 150, 150
            DW 160, 160, 160, 160
            DW 170, 170, 170, 170
            DW 180, 180, 180, 190
            DW 190, 190, 200, 200
            DW 200, 210, 210, 210
            DW 220, 220, 220, 230
            DW 230, 230, 240, 240
            DW 250, 250, 250, 260
            DW 260, 270, 270, 280
            DW 280, 290, 290, 300
            DW 300, 310, 310, 320
          . DW 320, 330, 330, 340
            DW 350, 350, 360, 360
            DW 370, 380, 380, 390
            DW 400, 410, 410, 420
            DW 430, 440, 450, 450
            DW 460, 470, 480, 490
            DW 500, 510, 520, 530
            DW 540, 550, 570, 580
            DW 590, 600, 620, 630
            DW 640, 660, 670, 690
            DW 700, 720, 740, 760
            DW 770, 790, 810, 830
            DW 850, 880, 900, 920
            DW 950, 980, 1000, 1030
            DW 1060, 1090, 1130, 1160
            DW 1200, 1240, 1280, 1320
            DW 1370, 1420, 1470, 1520
            DW 1580, 1640, 1710, 1780
            DW 1860, 1940, 2030, 2130
            DW 2230, 2350, 2470, 2610
            DW 2770, 2940, 3130, 3340
            DW 3590, 3860, 4180, 4560
            DW 4990, 5520, 6160, 6950
            DW 7970, 9300, 9999, 9999
            DW 9999, 9999, 9999, 9999

;---------------------------------------------------------------------------
; The TADTBL or Temperature A/D TaBLe, is used to determine the CF index
TADTBL: DB  59,  68,  74,  80,  87,  94, 101, 109
        DB 117, 127, 134, 142, 151, 159, 168, 176
        DB 184, 191, 198, 205, 211, 225, 255

;---------------------------------------------------------------------------
            END

2500 A.D. 6805 Macro Assembler  -  Version 4.00c
            ---------------------------------------------------

Input  Filename : AM450.asm
                    Output Filename : AM450.obj

1                                           PL 57
2       0000                                TITLE AQUAMETER MODEL 450 CO SCENTRY
```

```
7/10/86
    3   0000                              STTL Microware Systems
    4                                     RECSIZE 32
    5                                     OPTIONS H
    6   0000
    7                          ; Current hardware is 68705r3 MCU
    8
    9                          ; ******************************
   10                          ; ******************************
   11                          ; ***                        ***
   12                          ; ***    M O D E L   4 5 0   ***
   13                          ; ***    ---------   -----   ***
   14                          ; ***                        ***
   15                          ; ***    MICROWARE SYSTEMS   ***
   16                          ; ***        AQUAMETER       ***
   17                          ; ***    COPYRIGHT (C) 1986  ***
   18                          ; ***    ALL RIGHTS RESERVED ***
   19                          ; ***                        ***
   20                          ; ******************************
   21                          ; ******************************
   22
   23
   24                                    PAGE
   25                          ; SYSTEM EQUATES
   26
   27   0000                   PORTA    EQU     000H    ; port a data register
   28   0001                   PORTB    EQU     001H    ; port b data register
   29   0002                   PORTC    EQU     002H    ; port c data register
   30   0003                   PORTD    EQU     003H    ; port d data register
   31   0004                   PADDR    EQU     004H    ; port a data direction
register
   32   0005                   PBDDR    EQU     005H    ; port b data direction
register
   33   0006                   PCDDR    EQU     006H    ; port c data direction
register
   34   0008                   TDR      EQU     008H    ; timer data register
   35   0009                   TCR      EQU     009H    ; timer control register
   36   000A                   MSCREG   EQU     00AH    ; Miscellaneous Register 37   000E                   ADCON    EQU     00EH    ; A/D control register
   38   000F                   ADREG    EQU     00FH    ; A/D result register
   39   0060                   WORK1    EQU     60H     ; WORKING STORAGE
   40   005F                   WORK2    EQU     5FH     ; WORKING STORAGE
   41   003E                   WORK3    EQU     3EH     ; WORKING STORAGE
   42   003F                   WORK4    EQU     3FH     ; WORKING STORAGE
   43   004A                   MATH.0   EQU     4AH     ; MULTIPLY & DIVIDE REGS
   44   004B                   MATH.1   EQU     4BH     ; MULTIPLY & DIVIDE REGS
   45   004C                   MATH.2   EQU     4CH     ; MULTIPLY & DIVIDE REGS
   46   004D                   MATH.3   EQU     4DH     ; MULTIPLY & DIVIDE REGS
   47   004E                   MATH.4   EQU     4EH     ; MULTIPLY & DIVIDE REGS
   48   004F                   MATH.5   EQU     4FH     ; MULTIPLY & DIVIDE REGS
   49   005F                   MATH.6   EQU     WORK2   ; EXTENDED MULTIPLY REG
   50   005D                   FLAG0    EQU     5DH     ; FLAG REGISTER 0
   51   005C                   FLAG1    EQU     5CH     ; FLAG REGISTER 1
   52   0050                   TIME.0   EQU     50H     ; TIME LS COUNT
   53   0051                   TIME.1   EQU     51H     ; TIME MS COUNT
   54   005B                   DSPBNC   EQU     5BH     ; DISPLAY SWITCH DEBOUNC
E TIMER
   55   0035                   TIMER    EQU     35H     ; Debounce timer locatio
n
   56   0036                   SECNT.0  EQU     36H     ; Seconds counter
   57   0037                   SECNT.1  EQU     37H     ; Ditto.
   58   0033                   NXTIM.0  EQU     33H     ; Next .01 second down c
ounter value <ls>
   59   0034                   NXTIM.1  EQU     34H     ; Next .01 second down c
ounter value <ms>
   60   0052                   TMP.0    EQU     52H     ; TEMP DATA
   61   0053                   TMP.1    EQU     53H     ; TEMP DATA
   62   0054                   TMP.2    EQU     54H     ; TEMP DATA
   63   0031                   COC1.0   EQU     31H     ; CURRENT COC
   64   0032                   COC1.1   EQU     32H
   65   0030                   VSENS    EQU     30H     ; SENSOR VOLTAGE A/D
```

```
                                            PUT
 66        003D            TEMP    EQU    3DH    ; TEMPERATURE VOLTAGE A/D/ INPUT
 67        0040            COHB0.0 EQU    40H    ; OLD %CO IN Hb
 68        0041            COHB0.1 EQU    41H    ; MIDDLE BYTE
 69        0042            COHB0.2 EQU    42H    ; MS
 70        003A            COHB1.0 EQU    3AH    ; NEW %CO IN Hb
 71        003B            COHB1.1 EQU    3BH    ; MIDDLE BYTE
 72        003C            COHB1.2 EQU    3CH    ; MS
 73        0043            CONST.0 EQU    43H    ; CONST STORAGE
 74        0044            CONST.1 EQU    44H    ; CONST STORAGE
 75        0045            CTMP.0  EQU    45H    ; INTERIM RESULTS
 76        0046            CTMP.1  EQU    46H    ; INTERIM RESULTS
 77        0047            CTMP.2  EQU    47H    ; INTERIM RESULTS
 78        0011            SHLMP   EQU    11H    ; SH HH LAMP VALUE
 79        0009            MMLMP   EQU    09H    ; MM HH LAMP VALUE
 80        0005            LLLMP   EQU    05H    ; LL HH LAMP VALUE
 81        0000            NOLMP   EQU    00H    ; NO HH LAMP VALUE
 82        00E2            LMPMSK  EQU    0E2H   ; LAMP DRIVER MASK
 83        005E            LBUZZ   EQU    05EH   ; BUZZER ON TIMER
 84        0038            LOFF.0  EQU    038H   ; BUZZER OFF TIMER (LS)
 85        0039            LOFF.1  EQU    039H   ; BUZZER OFF TIMER (MS)
 86        005A            BTIMER  EQU    05AH   ; BUTTON 2.5 SECOND TIMER
 87        0059            TBUTT   EQU    059H   ; # OF BUTTON PRESSES DURING 2.5 SECONDS
 88        0058            SENSCHK EQU    58H    ; COC SENSOR MONITOR STORAGE
 89        00CD            MAXLED  EQU    205    ; MAX A/D INPUT WITH 1 LED ON
 90        0066            MINLED  EQU    102    ; MIN A/D INPUT WITH 1 LED ON
 91        0057            STATE   EQU    57H    ; TEST STATE VARIABLE
 92        0056            SAVE.0  EQU    56H    ; TEST DATA STORAGE
 93        0048            SAVE.1  EQU    48H    ; TEST DATA STORAGE
 94        0049            SAVE.2  EQU    49H    ; TEST DATA STORAGE
 95        0055            COCHB   EQU    55H    ; 1 BYTE % BLOOD LEVEL
 96        002E            CF.0    EQU    2EH    ; low temperature correction factor
 97        002F            CF.1    EQU    2FH    ; high byte temperature correction factor
 98        002D            COCIDX  EQU    2DH    ; latest PPM carbon monoxide index value
 99        0028            DISBUF  EQU    28H    ; 28-2C is display buffer
100        0025            BCD0    EQU    25H    ; LS bcd storage
101        0026            BCD1    EQU    26H
102        0027            BCD2    EQU    27H    ; MS bcd storage
103        0024            SAVACC  EQU    24H    ; Error display Accumulator save register
104        0023            SAVX    EQU    23H    ; Error display x reg save register
105        0022            ERRCOD  EQU    22H    ; Last noted error code
106        0028            TIMDL1  EQU    DISBUF
107        0029            TIMDL2  EQU    DISBUF+1
108
109                        ; Model 450 FLAG BIT ASSIGNMENTS
110                        ;----------------------------------------
111                        ; FLAG 0
112                        ;   7   :   6   :   5   :   4   :   3   :   2   :   1   :   0   ;
113                        ;----------------------------------------
114                        ; TEST : OLD : FAULT : BUZZER : HH1   : HHO  : HEALTH : timer  :
115                        ; MODE : INT : EXISTS: ENABLE : 00=L/L  01=M/M : HAZARD : elapsed:
116                        ;      : STATE:       :        : 10=S/H  11=X  : EXISTS :        :
117                        ;----------------------------------------
118                                    PAGE
```

```
119                              ; FLAG 1
120                              ;  7    :   6    :   5    :   4    :   3    :
  2   :   1   :   0   :
121                              ;----------------------------------------------
------------------------
122                              ; Lead  : Error  : UPDATE  :         :BUZZER :CU
RRENT : TEST MODE STATE :
123                              ; Zero  : Display: DISPLAY:         : REQ   :BU
ZZER  :00 = T0  01 = T1 :
124                              ; Blank : Request:        :         :       : S
TATE  :10 = T2  11 = T3 :
125                              ;----------------------------------------------
------------------------
  2   :   1   :   0   :
126
127                              ; PORTA (LAMPS)
                                 ;  7    :   6    :   5    :   4    :   3    :
  2   :   1   :   0   :
128
                                 ;----------------------------------------------
------------------------
129                              ; DIP    : LONG   : MED    : SHORT  : TEST   : F
AULT  : BUZZER : HEALTH :
130                              ; SWITCH : EXPOSR : EXPOSR : EXPOSR :        :
                                                             : HAZARD :
131                              ; 7      :        :        :        :        :
      :        :        :
132                              ;----------------------------------------------
------------------------
133
134
135                                      PAGE
136    0F38                              ORG 0F38H           ; Mask Options Register
Address
137    0F38  00                          DB 00H              ; Select Crystal Oscilla
tor
138
139
140    0FF8                              ORG 0FF8H
141    0FF8  0680                        DW TIMINT           ; TIMER INTERRUPT VECTOR
142    0FFA  00B9                        DW EXTINT           ; EXTERNAL INTERRUPT VEC
TOR
143    0FFC  00BA                        DW SWINT            ; SOFTWARE INTERRUPT VEC
TOR
144    0FFE  00C6                        DW RESET            ; INITIAL RESET VECTOR
145    1000
146    0080                              ORG 0080H
147                              ; Health hazard check values
148    0080  00 07 D0            LLVAL:  DB 000H, 007H, 0D0H ; %COHB/OC = .20
149    0083  00 27 10            MMVAL:  DB 000H, 027H, 010H ; %COHB/OC = 1.0
0
150
151    0086  80 BB               HICHKI: DB 128,187
152    0088  BE F5               LOCHKI: DB 190,245
153
154                              ;       PORT DATA AND DIRECTION INITIAL VALUES
155    008A                      INITVAL:
156    008A  00                          DB 000H             ; PORTA DATA
157    008B  00                          DB 000H             ; PORTB DATA
158    008C  00                          DB 000H             ; PORTC DATA
159    008D  00                          DB 000H             ; PORTD DATA
160    008E  7F                          DB 07FH             ; ADDR DATA
161    008F  7F                          DB 07FH             ; BDDR DATA
162    0090  35                          DB 035H             ; CDDR DATA
163
164                              ;--------------------------
165                              ;       SEVEN SEGMENT LOOK-UP TABLE
166    0091                      SEGTBL:
167    0091  77 41 3B 6B                 DB 077H, 041H, 03BH, 06BH    ; DIGIT
4
168    0095  4D 6E 7E 43                 DB 04DH, 06EH, 07EH, 043H
169    0099  7F 4F                       DB 07FH, 04FH
170
171    009B  6F 03 76 57                 DB 06FH, 003H, 076H, 057H    ; DIGIT
3
```

```
172    009F   1B 5D 7D 07              DB 01BH, 05DH, 07DH, 007H
173    00A3   7F 1F                    DB 07FH, 01FH
174
175    00A5   7B 0A 5D 4F              DB 07BH, 00AH, 05DH, 04FH      ; DIGIT 2
176    00A9   2E 67 77 4A              DB 02EH, 067H, 077H, 04AH
177    00AD   7F 6E                    DB 07FH, 06EH
178
179    00AF   7D 30 6E 7A              DB 07DH, 030H, 06EH, 07AH      ; DIGIT 1
180    00B3   33 5B 5F 70              DB 033H, 05BH, 05FH, 070H
181    00B7   7F 73                    DB 07FH, 073H
182
183                             ;------------------------
184    00B9   80              EXTINT: RTI             ; NO EXTERNAL INTERRUPT
185    00BA   80              SWINT:  RTI             ; Or Software Interrupt either.
186
187                             ;------------------------
188    00BB   A6 00           MEMCLR: LDA #0
189    00BD   AE 60                   LDX #60H
190    00BF                   MEMINIT:
191    00BF   F7                      STA ,X          ; clear ram for initial use.
192    00C0   5A                      DECX
193    00C1   A3 0F                   CPX #0FH
194    00C3   26 FA                   BNE MEMINIT
195    00C5   81                      RTS
196
197                             ;------------------------
198    00C6   9B              RESET:  SEI             ; Disable external interrupts
199    00C7   A6 40                   LDA #40H
200    00C9   B7 09                   STA TCR         ; Disable timer interrupts
201    00CB   AE 00                   LDX #0
202    00CD   D6 00 8A        INITIO: LDA INITVAL,X
203    00D0   F7                      STA ,X
204    00D1   5C                      INCX
205    00D2   A3 08                   CPX #8          ; done loading initial values?
206    00D4   26 F7                   BNE INITIO
207    00D6   1C 0A                   BSET 6,MSCREG   ; MASK OUT INT2 INTERRUPTS
208    00D8   AD E1                   BSR MEMCLR      ; CLEAN UP MEMORY
209                             ;------------------------------------------
210    00DA   9B              MAIN:   SEI
211    00DB   A6 70                   LDA #<6000
212    00DD   B7 36                   STA SECNT.0
213    00DF   B7 33                   STA NXTIM.0
214    00E1   A6 17                   LDA #>6000
215    00E3   B7 37                   STA SECNT.1
216    00E5   B7 34                   STA NXTIM.1
217
218    00E7   A6 07                   LDA #07H        ; SET UP TIMER
219    00E9   B7 09                   STA TCR
220    00EB   A6 46                   LDA #70
221    00ED   B7 08                   STA TDR
222
223    00EF   4F                      CLRA
224    00F0   CD 0A 6C                JSR FILDSP
225    00F3   CD 0A 31                JSR DISPLAY
226    00F6   CD 01 EB                JSR DSPHB
227
228    00F9   0D 02 04                BRCLR 6,PORTC,CHKMOD   ; TEST MODE
229    00FC   9A                      CLI             ; ENABLE INTERRUPTS
230    00FD   CC 07 5D                JMP PWRUP
231
232    0100   A6 C8           CHKMOD: LDA #<200
233    0102   B7 36                   STA SECNT.0
234    0104   B7 33                   STA NXTIM.0
```

```
235    0106   A6 00                      LDA  #>200
236    0108   B7 37                      STA  SECNT.1
237    010A   B7 34                      STA  NXTIM.1
238    010C   9A                         CLI
239
240    010D   CD 04 94        CHECK:     JSR  READ0
241    0110   B7 30                      STA  VSENS
242    0112   CD 04 98                   JSR  READ1
243    0115   B7 3D                      STA  TEMP
244    0117   CD 01 DD                   JSR  PROCES
245
246    011A   01 5D FD        PAUSE:     BRCLR 0,FLAG0,PAUSE
247    011D   11 5D                      BCLR  0,FLAG0
248    011F   CC 01 0D                   JMP   CHECK
249
250    0122   CC 08 27        TESTJ1:    JMP   TEST
251                           ;------------------------------------------------
252
253    0125   A6 B8           OC0:       LDA  #<3000             ; SET UP TIMER F
OR 90 SECONDS OF LOW CURRENT
254    0127   B7 33                      STA  NXTIM.0
255    0129   A6 0B                      LDA  #>3000             ; <ACTUALLY 3 CY
CLES OF 30 SECONDS>
256    012B   B7 34                      STA  NXTIM.1
257    012D   11 5D                      BCLR  0,FLAG0
258    012F   1A 02                      BSET  5,PORTC           ; TURN ON HIGH C
URRENT
259    0131   18 02                      BSET  4,PORTC
260
261    0133   1B 00                      BCLR  5,PORTA           ; CLEAR TEST LAM
P
262    0135   CD 03 E0                   JSR   INDCTR            ; PROCESS PREVIO
USLY AQUIRED DATA
263    0138   CD 01 E6                   JSR   LCDDSP
264    013B   00 5C 03                   BRCLR 6,FLAG1,OC01
265    013E   CD 02 61                   JSR   ERRDSP
266
267    0141   CD 05 62        OC01:      JSR   BUTTON
268    0144   25 DC                      BCS   TESTJ1
269    0146   CD 05 50                   JSR   DMPCHK
270    0149   0B 5C 03                   BRCLR 5,FLAG1,DSP1A
271    014C   CD 01 E6                   JSR   LCDDSP
272    014F   01 5D EF        DSP1A:     BRCLR 0,FLAG0,OC01      ; HIGH CURRENT F
OR 60 SECONDS
273    0152   AE 86                      LDX   #HICHKI
274    0154   CD 0A DC                   JSR   CHKI
275
276    0157   1B 02                      BCLR  5,PORTC
277    0159   11 5D                      BCLR  0,FLAG0           ; THEN LOW FOR 9
0
278
279    015B   CD 07 D7                   JSR   LMPCHK
280    015E   CD 07 C0                   JSR   LEDCHK
281    0161   0D 5C 03                   BRCLR 6,FLAG1,LOWC1
282    0164   CD 02 61                   JSR   ERRDSP
283
284    0167   CD 05 62        LOWC1:     JSR   BUTTON
285    016A   25 6B                      BCS   TESTJ
286    016C   CD 05 50                   JSR   DMPCHK
287    016F   0B 5C 03                   BRCLR 5,FLAG1,DSP1B
288    0172   CD 01 E6                   JSR   LCDDSP
289    0175   01 5D EF        DSP1B:     BRCLR 0,FLAG0,LOWC1     ; FIRST 30 SECON
D PERIOD
290    0178   11 5D                      BCLR  0,FLAG0
291
292    017A   CD 02 7C                   JSR   TSTVS             ; TEST SENSOR VOLTAGE
293    017D   CD 05 62        LOWC2:     JSR   BUTTON
294    0180   25 55                      BCS   TESTJ
295    0182   CD 05 50                   JSR   DMPCHK
296    0185   0B 5C 03                   BRCLR 5,FLAG1,DSP1C
297    0188   CD 01 E6                   JSR   LCDDSP
298    018B   01 5D EF        DSP1C:     BRCLR 0,FLAG0,LOWC2     ; SECOND 30 SECO
```

```
ND PERIOD
299    018E   11 5D                 BCLR 0,FLAG0
300    0190   CD 02 7C               JSR TSTVS       ; TEST SENSOR VOLTAGE
301
302    0193   A6 19                  LDA #25
303    0195   B7 33                  STA NXTIM.0
304    0197   3F 34                  CLR NXTIM.1
305    0199   CD 05 62        OC1:   JSR BUTTON
306    019C   25 39                  BCS TESTJ
307    019E   CD 05 50               JSR DMPCHK
308    01A1   0B 5C 03               BRCLR 5,FLAG1,DSP1D
309    01A4   CD 01 E6               JSR LCDDSP
310    01A7   01 5D EF        DSP1D: BRCLR 0,FLAG0,OC1    ; 3RD AND FINAL
30 SECOND PERIOD
311    01AA   AE 88                  LDX #LOCHKI
312    01AC   CD 0A DC               JSR CHKI
313                                                   ; WAIT 25 MILLIS
ECONDS
314    01AF   19 02                  BCLR 4,PORTC    ; WITH CURRENT O
FF
315    01B1   11 5D                  BCLR 0,FLAG0
316    01B3   A6 70                  LDA #<6000
317    01B5   B7 33                  STA NXTIM.0
318    01B7   A6 17                  LDA #>6000
319    01B9   B7 34                  STA NXTIM.1     ; SET UP TIMER F
OR 60 SECONDS
320    01BB   01 5D FD        OC1A:  BRCLR 0,FLAG0,OC1A   ; THEN SAMPLE
321    01BE   CD 04 94               JSR READ0
322    01C1   B7 30                  STA VSENS
323    01C3   CD 04 98               JSR READ1
324    01C6   B7 3D                  STA TEMP
325    01C8   11 5D                  BCLR 0,FLAG0
326    01CA   1A 02                  BSET 5,PORTC    ; TURN ON HIGH C
URRENT
327    01CC   18 02                  BSET 4,PORTC
328    01CE   CD 02 D3               JSR GETCOC      ; GET CURRENT COC
329    01D1   CD 03 80               JSR HBCOC       ; COMPUTE BLOOD LEVEL
330    01D4   CC 01 25               JMP OC0
331
332    01D7   CC 08 27        TESTJ: JMP TEST
333                                  PAGE
334                                  ;----- PROCESS DATA HERE -------
335    01DA   CC 02 61        ERRDJ: JMP ERRDSP      ; jmp fixup
336
337    01DD   CD 02 D3        PROCES: JSR GETCOC     ; GET CURRENT COC
338    01E0   CD 03 80               JSR HBCOC       ; COMPUTE BLOOD LEVEL AN
D SET OUTPUTS
339    01E3   CD 03 E0               JSR INDCTR
340    01E6   0C 5C F1        LCDDSP: BRSET 6,FLAG1,ERRDJ
341    01E9   2E 3E                  BIL DSPCOC
342    01EB   0C 5C EC        DSPHB: BRSET 6,FLAG1,ERRDJ
343    01EE   B6 3A                  LDA COHB1.0     ; Display current blood
% CoC
344    01F0   B7 4A                  STA MATH.0
345    01F2   B6 3B                  LDA COHB1.1
346    01F4   B7 4B                  STA MATH.1
347    01F6   B6 3C                  LDA COHB1.2
348    01F8   B7 4C                  STA MATH.2
349    01FA   A6 64                  LDA #100
350    01FC   B7 43                  STA CONST.0
351    01FE   3F 44                  CLR CONST.1
352    0200   3F 4D                  CLR MATH.3
353    0202   AE 43                  LDX #CONST.0
354    0204   CD 06 49               JSR DIVIDE      ; Set up value to xx.xx
355
356    0207   CD 05 08               JSR BINBCD
357    020A   1F 5C                  BCLR 7,FLAG1
358    020C   3F 5F                  CLR WORK2
359    020E   B6 26                  LDA BCD1
360    0210   CD 0A 75               JSR LEFT
361    0213   AA 80                  ORA #80H
```

```
362    0215   B7 28                      STA DISBUF
363    0217   B6 26                      LDA BCD1
364    0219   1E 5C                      BSET 7,FLAG1
365    021B   CD 0A 79                   JSR RIGHT
366    021E   AA 80                      ORA #80H
367    0220   B7 29                      STA DISBUF+1
368    0222   B6 25                      LDA BCD0
369    0224   CD 0A 75                   JSR LEFT
370    0227   20 27                      BRA DSPC1
371                              ;       STA DISBUF+2
372                              ;       LDA BCD0
373                              ;       BRA DSPCOM
374                              ;       JSR RIGHT
375                              ;       STA DISBUF+3
376                              ;       CLR DISBUF+4
377                              ;       JSR DISPLAY
378                              ;       RTS
379
380    0229   0C 5C 35           DSPCOC: BRSET 6,FLAG1,ERRDSP
381    022C   B6 31                      LDA COC1.0        ; Display current Co level (ambient)
382    022E   B7 4A                      STA MATH.0
383    0230   B6 32                      LDA COC1.1
384    0232   B7 4B                      STA MATH.1
385
386    0234   CD 05 08                   JSR BINBCD
387    0237   1F 5C                      BCLR 7,FLAG1
388    0239   3F 5F                      CLR WORK2
389    023B   B6 26                      LDA BCD1
390    023D   CD 0A 75                   JSR LEFT
391    0240   B7 28                      STA DISBUF
392    0242   B6 26                      LDA BCD1
393    0244   CD 0A 79                   JSR RIGHT
394    0247   B7 29                      STA DISBUF+1
395    0249   B6 25                      LDA BCD0
396    024B   CD 0A 75                   JSR LEFT
397    024E   AA 80                      ORA #80H
398    0250   B7 2A              DSPC1:  STA DISBUF+2
399    0252   B6 25                      LDA BCD0
400    0254   1E 5C              DSPCOM: BSET 7,FLAG1
401    0256   CD 0A 79                   JSR RIGHT
402    0259   B7 2B                      STA DISBUF+3
403    025B   3F 2C                      CLR DISBUF+4
404    025D   CD 0A 31                   JSR DISPLAY
405    0260   81                         RTS
406
407                              ;-------------------------------------------------
408    0261   1D 5C              ERRDSP: BCLR 6,FLAG1    ; ACKNOWLEDGE ERROR CODE
409    0263   A6 3E                      LDA #3EH
410    0265   B7 28                      STA DISBUF
411    0267   A6 30                      LDA #30H
412    0269   B7 29                      STA DISBUF+1
413    026B   A6 14                      LDA #20
414    026D   B7 5F                      STA WORK2
415    026F   B6 22                      LDA ERRCOD
416    0271   1F 5C                      BCLR 7,FLAG1
417    0273   CD 0A 75                   JSR LEFT
418    0276   B7 2A                      STA DISBUF+2
419    0278   B6 22                      LDA ERRCOD
420    027A   20 D8                      BRA DSPCOM
421                              ;       BSET 7,FLAG1
422                              ;       JSR RIGHT
423                              ;       STA DISBUF+3
424                              ;       CLR DISBUF+4
425                              ;       JSR DISPLAY
426                              ;       RTS
427
428                              ;-------------------------------------------------
429    027C   19 02              TSTVS:  BCLR 4,PORTC    ; TURN OFF CURRENT FOR 20 MILLISECONDS
```

```
430   027E   A6 02                   LDA #2
431   0280   B7 35                   STA TIMER
432   0282   B6 35         TSTVS1:   LDA TIMER
433   0284   26 FC                   BNE TSTVS1
434   0286   B6 30                   LDA VSENS
435   0288   B7 56                   STA SAVE.0
436   028A   CD 04 94                JSR READ0
437   028D   18 02                   BSET 4,PORTC              ; TURN CURRENT BACK ON
438   028F   B7 30                   STA VSENS
439   0291   CD 04 98                JSR READ1
440   0294   B7 3D                   STA TEMP
441   0296   CD 02 D3                JSR GETCOC
442   0299   A6 EF                   LDA #239
443   029B   B1 2D                   CMP COCIDX
444   029D   24 1F                   BHS VSOK
445   029F   A6 19                   LDA #25
446   02A1   CD 04 AC                JSR CHKHB
447   02A4   25 0C                   BCS OKHB1
448   02A6   A6 03                   LDA #3
449   02A8   B7 3C                   STA COHB1.2
450   02AA   A6 D0                   LDA #0D0H
451   02AC   B7 3B                   STA COHB1.1
452   02AE   A6 90                   LDA #090H
453   02B0   B7 3A                   STA COHB1.0
454   02B2   16 5C         OKHB1:    BSET 3,FLAG1
455   02B4   12 5D                   BSET 1,FLAG0
456   02B6   CD 04 55                JSR SHLEV
457   02B9   A6 40                   LDA #40H                  ; SET LED R2
458   02BB   B7 01                   STA PORTB
459   02BD   81                      RTS
460
461   02BE   B6 56         VSOK:     LDA SAVE.0                ; RESTORE OLD VSENS
462   02C0   B7 30                   STA VSENS
463   02C2   CD 02 D3                JSR GETCOC
464   02C5   81                      RTS
465
466                                  ;---------------------------------------------
467
468                                  ;---------------------------------------------
469   02C6   5C            HITEMP:   INCX
470                                  ; ( SHOULD ALSO SET FAULT LAMP HERE )
471   02C7   A6 03                   LDA #03H
472   02C9   20 03                   BRA BADTMP
473   02CB   5A            LOTEMP:   DECX
474                                  ; ( SHOULD ALSO SET FAULT LAMP HERE )
475   02CC   A6 04                   LDA #04H
476   02CE   CD 07 4F      BADTMP:   JSR SETFLT
477   02D1   20 13                   BRA OKTEMP
478
479   02D3   B6 3D         GETCOC:   LDA TEMP                  ; get temperature a/d value
480   02D5   5F                      CLRX
481   02D6   D1 0F 16      CHKTAD:   CMP TADTBL,X
482   02D9   23 03                   BLS TSTTAD
483   02DB   5C                      INCX
484   02DC   20 F8                   BRA CHKTAD
485   02DE   A3 00         TSTTAD:   CPX #0
486   02E0   27 E4                   BEQ HITEMP
487   02E2   A3 16                   CPX #22
488   02E4   24 E5                   BHS LOTEMP
489   02E6   5A            OKTEMP:   DECX
490   02E7   58                      LSLX
491   02E8   D6 0A EC                LDA TCTBL,X
492   02EB   B7 2F                   STA CF.1
493   02ED   D6 0A ED                LDA TCTBL+1,X
494   02F0   B7 2E                   STA CF.0
495   02F2   B6 30         GETRS:    LDA VSENS                 ; normalize RS value
496   02F4   48                      LSLA                      ; first do table lookup
```

```
497    02F5   24 OD                         BCC  LOWRS
498    02F7   97                            TAX
499    02F8   D6 OC 16                      LDA  RSTBL+256,X
500    02FB   B7 4B                         STA  MATH.1
501    02FD   D6 OC 17                      LDA  RSTBL+257,X
502    0300   B7 4A                         STA  MATH.0
503    0302   20 OB                         BRA  FIXRS
504    0304   97              LOWRS:        TAX
505    0305   D6 OB 16                      LDA  RSTBL,X
506    0308   B7 4B                         STA  MATH.1
507    030A   D6 OB 17                      LDA  RSTBL+1,X
508    030D   B7 4A                         STA  MATH.0
509    030F                   FIXRS:
510    030F   B6 2E                         LDA  CF.0
511    0311   B7 43                         STA  CONST.0
512    0313   B6 2F                         LDA  CF.1
513    0315   B7 44                         STA  CONST.1
514    0317   AE 43                         LDX  #CONST.0
515    0319   CD 05 F6                      JSR  MUL16         ; multiply 20 degree RS
value by temp CF
516    031C   A6 10                         LDA  #<10000
517    031E   B7 43                         STA  CONST.0
518    0320   A6 27                         LDA  #>10000
519    0322   B7 44                         STA  CONST.1
520    0324   AE 43                         LDX  #CONST.0
521    0326   CD 06 49                      JSR  DIVIDE        ; scale result back to n
ormal
522    0329
523    0329   A6 00                         LDA  #0
524    032B   B7 60                         STA  WORK1         ; get index corr
esponding to normalized RS
525
526    032D   B6 4C                         LDA  MATH.2
527    032F   26 2F                         BNE  GOTIDX        ; LARGE NUMBERS
ARE FIRST IN RS TABLE 7/9/86
528
529    0331   BE 60          GETIDX:        LDX  WORK1
530    0333   58                            LSLX
531    0334   25 1A                         BCS  GIDXHI
532    0336   B6 4B                         LDA  MATH.1
533    0338   D1 OB 16                      CMP  RSTBL,X
534    033B   25 09                         BLO  NXTIDX
535    033D   22 21                         BHI  GOTIDX
536    033F   B6 4A                         LDA  MATH.0
537    0341   D1 OB 17                      CMP  RSTBL+1,X
538    0344   24 1A                         BHS  GOTIDX
539    0346   3C 60          NXTIDX:        INC  WORK1
540    0348   26 E7                         BNE  GETIDX
541    034A   A6 FF          HIIDX:         LDA  #0FFH
542    034C   B7 60                         STA  WORK1
543    034E   20 10                         BRA  GOTIDX
544
545    0350   B6 4B          GIDXHI:        LDA  MATH.1
546    0352   D1 OC 16                      CMP  RSTBL+256,X
547    0355   25 EF                         BLO  NXTIDX
548    0357   22 07                         BHI  GOTIDX
549    0359   B6 4A                         LDA  MATH.0
550    035B   D1 OC 17                      CMP  RSTBL+257,X
551    035E   25 E6                         BLO  NXTIDX
552    0360
553    0360   B6 60          GOTIDX:        LDA  WORK1
554    0362   BE 60                         LDX  WORK1
555    0364   BF 2D                         STX  COCIDX
556    0366   58                            LSLX
557    0367   24 OC                         BCC  LOWCOC
558    0369   D6 OE 16                      LDA  COCTBL+256,X
559    036C   B7 32                         STA  COC1.1
560    036E   D6 OE 17                      LDA  COCTBL+257,X
561    0371   B7 31                         STA  COC1.0
562    0373   20 OA                         BRA  GOTCOC
563    0375   D6 OD 16       LOWCOC:        LDA  COCTBL,X
```

```
564   0378   B7 32              STA COC1.1
565   037A   D6 0D 17           LDA COCTBL+1,X
566   037D   B7 31              STA COC1.0
567   037F   81          GOTCOC: RTS
568
569                          ;----------------------------------------
570   0380-               HBCOC:
571                         ; Compute percentage CO in blood
572   0380   B6 31              LDA COC1.0
573   0382   B7 4A              STA MATH.0        ; load current CO sensor into math regs
574   0384   B6 32              LDA COC1.1
575   0386   B7 4B              STA MATH.1
576   0388   A6 2A              LDA #42
577   038A   B7 5F              STA WORK2
578   038C   CD 06 25           JSR MULWK22       ; and multiply by .0042
579   038F   B6 4A              LDA MATH.0
580   0391   AB 11              ADD #17           ; add .0017 to result
581   0393   B7 45              STA CTMP.0        ; and save interim results
582   0395   B6 4B              LDA MATH.1
583   0397   A9 00              ADC #0
584   0399   B7 46              STA CTMP.1
585   039B   B6 4C              LDA MATH.2        ; 6/18/86 used to be math.3 -->bug
586   039D   A9 00              ADC #0
587   039F   B7 47              STA CTMP.2
588                         ;-- multiply old COHb by .9745 --
589   03A1   A6 11              LDA #<9745
590   03A3   B7 43              STA CONST.0
591   03A5   A6 26              LDA #>9745
592   03A7   B7 44              STA CONST.1
593   03A9   B6 3A              LDA COHB1.0
594   03AB   B7 4A              STA MATH.0
595   03AD   B7 40              STA COHB0.0
596
597   03AF   B6 3B              LDA COHB1.1
598   03B1   B7 4B              STA MATH.1
599   03B3   B7 41              STA COHB0.1
600
601   03B5   B6 3C              LDA COHB1.2
602   03B7   B7 4C              STA MATH.2
603   03B9   B7 42              STA COHB0.2
604
605   03BB   AE 43              LDX #CONST.0
606   03BD   CD 05 F8           JSR MUL23         ; perform multiplication
607
608   03C0   A6 10              LDA #<10000
609   03C2   B7 43              STA CONST.0
610   03C4   A6 27              LDA #>10000
611   03C6   B7 44              STA CONST.1
612   03C8   AE 43              LDX #CONST.0
613   03CA   CD 06 4B           JSR DIV52         ; scale multiplication results back down
614
615   03CD   B6 4A              LDA MATH.0        ; save new COHb
616   03CF   BB 45              ADD CTMP.0
617   03D1   B7 3A              STA COHB1.0
618   03D3   B6 4B              LDA MATH.1
619   03D5   B9 46              ADC CTMP.1
620   03D7   B7 3B              STA COHB1.1
621   03D9   B6 4C              LDA MATH.2
622   03DB   B9 47              ADC CTMP.2
623   03DD   B7 3C              STA COHB1.2
624   03DF   81                 RTS
625
626                          ;----------------------------------------
627   03E0   0B 5D 0B    INDCTR: BRCLR 5,FLAG0,OKIND    ; NO INDICATORS DURING A FAULT
628   03E3   A6 00       KILIND: LDA #0
629   03E5   B7 01              STA PORTB
```

```
630  03E7  B6 00              LDA PORTA
631  03E9  A4 E2              AND #0E2H         ; CLEAR LAMPS BUT NOT BUZZER
632  03EB  B7 00              STA PORTA
633  03ED  81                 RTS               ; AND BUG OUT
634
635                           ; determine led status
636  03EE  B6 2D      OKIND:  LDA COCIDX
637  03F0  B7 60              STA WORK1
638  03F2  AE 00      LEDST:  LDX #0
639  03F4  A6 06      LEDST1: LDA #6
640  03F6  B7 3E              STA WORK3
641  03F8  CD 04 D3           JSR CHKLES
642  03FB  B6 3E              LDA WORK3
643  03FD  97                 TAX
644  03FE  D6 05 01           LDA LEDTBL,X
645  0401  B7 01              STA PORTB
646
647                           ; compute hh status
648  0403  98                 CLC               ; READ DIPSWITCH SETTING
649  0404  4F                 CLRA
650  0405  0F 02 01           BRCLR 7,PORTC,MAP1 ; Check ms bit
651  0408  99                 SEC
652  0409  49         MAP1:   ROLA
653  040A  0F 03 01           BRCLR 7,PORTD,MAP2 ; 2nd ms bit
654  040D  99                 SEC
655  040E  49         MAP2:   ROLA
656  040F  0F 01 01           BRCLR 7,PORTB,MAP3 ; 3rd ms bit
657  0412  99                 SEC
658  0413  49         MAP3:   ROLA
659  0414  0F 00 01           BRCLR 7,PORTA,MAP4 ; And ls bit of switches
660  0417  99                 SEC
661  0418  49         MAP4:   ROLA
662  0419  AB 07              ADD A,#7
663  041B  CD 04 AC           JSR CHKHB
664  041E  24 0D              BCC HHOFF
665  0420  16 5C      HHON:   BSET 3,FLAG1      ; ENABLE BUZZER (HEALTH HAZARD EXISTS)
666  0422  02 5D 0E           BRSET 1,FLAG0,LAMPS ; SEE IF HEALTH HAZARD ALREADY EXISTS
667  0425  15 5D              BCLR 2,FLAG0      ; NO PREVIOUS H/H. CLEAR H/H STATE
668  0427  17 5D              BCLR 3,FLAG0
669  0429  12 5D              BSET 1,FLAG0      ; Set Health Hazard flag
670  042B  20 06              BRA LAMPS
671  042D  17 5C      HHOFF:  BCLR 3,FLAG1      ; DISABLE BUZZER
672  042F  13 5D              BCLR 1,FLAG0      ; AND CLEAR H/H FLAG
673  0431  20 3E              BRA NOLMPJ
674                           ; Determine lamp status
675  0433  B6 3A      LAMPS:  LDA COHB1.0
676  0435  B0 40              SUB COHB0.0
677  0437  B7 45              STA CTMP.0
678  0439  B6 3B              LDA COHB1.1
679  043B  B2 41              SBC COHB0.1
680  043D  B7 46              STA CTMP.1
681  043F  B6 3C              LDA COHB1.2
682  0441  B2 42              SBC COHB0.2
683  0443  B7 47              STA CTMP.2
684  0445  25 1F              BCS LLEV          ; IF CURRENT - LAST HB LEVEL IS (-) THEN LOW LEVEL
685  0447  AE 80              LDX #LLVAL
686  0449  CD 04 E1           JSR CHKHH
687  044C  25 18              BCS LLEV
688  044E  AE 83              LDX #MMVAL
689  0450  CD 04 E1           JSR CHKHH
690  0453  25 08              BCS MMLEV
691  0455  16 5D      SHLEV:  BSET 3,FLAG0
692  0457  15 5D              BCLR 2,FLAG0
693  0459  A6 11              LDA #SHLMP
```

```
694    045B    20 11              BRA SETLMP
695    045D    06 5D F5    MMLEV: BRSET 3,FLAG0,SHLEV
696                            ;  BCLR 3,FLAG0
697    0460    14 5D              BSET 2,FLAG0
698    0462    A6 09              LDA #MMLMP
699    0464    20 08              BRA SETLMP
700    0466    06 5D EC    LLEV:  BRSET 3,FLAG0,SHLEV
701    0469    04 5D F1           BRSET 2,FLAG0,MMLEV
702                            ;  BCLR 3,FLAG0
703                            ;  BCLR 2,FLAG0
704    046C    A6 05              LDA #LLLMP
705    046E    02 5D 02    SETLMP: BRSET 1,FLAG0,DOLMP
706    0471    A6 00       NOLMPJ: LDA #NOLMP
707    0473    B7 60       DOLMP: STA WORK1
708    0475    B6 00              LDA PORTA
709    0477    A4 E2              AND #LMPMSK
710    0479    BA 60              ORA WORK1
711    047B    B7 00              STA PORTA       ; SET LAMP STATUS (BUZZER IS AUTOMATIC)
712
713                         ; Determine if current coc is above 100 ppm
714    047D    07 5C 11           BRCLR 3,FLAG1,NOBUZZ
715    0480    B6 32              LDA COC1.1
716    0482    A1 00              CMP #>50        ;100
717    0484    22 08              BHI ENBUZZ
718    0486    25 09              BLO NOBUZZ
719    0488    B6 31              LDA COC1.0
720    048A    A1 32              CMP #<50        ;100
721    048C    25 03              BLO NOBUZZ
722    048E    18 5D       ENBUZZ: BSET 4,FLAG0   ; ENABLE BUZZER OUTPUT
723    0490    81                 RTS             ; AND RETURN
724    0491    19 5D       NOBUZZ: BCLR 4,FLAG0   ; DISABLE BUZZER OUTPUT
725    0493    81                 RTS             ; AND RETURN
726                                PAGE
727                         ;----------------------------------------
728                         ; Analog to Digital Conversion Routines
729                         ;----------------------------------------
730    0494    A6 00       READ0: LDA #0          ; READ AD0
731    0496    20 0A              BRA READAD
732    0498    A6 01       READ1: LDA #1          ; READ AD1
733    049A    20 06              BRA READAD
734    049C    A6 02       READ2: LDA #2          ; READ AD2
735    049E    20 02              BRA READAD
736    04A0    A6 03       READ3: LDA #3          ; READ AD3
737
738    04A2    A4 03       READAD: AND #03H       ; Read A/D channel selected by ACC
739    04A4    B7 0E              STA ADCON       ; Write selection to A/D control register,
740    04A6    0F 0E FD    WAITAD: BRCLR 7,ADCON,WAITAD ; And await completion.
741    04A9    B6 0F              LDA ADREG       ; retreive results
742    04AB    81                 RTS             ; and return.
743
744                         ;----------------------------------------
745    04AC    B7 5F       CHKHB: STA WORK2
746    04AE    A6 10              LDA #10H
747    04B0    B7 4A              STA MATH.0
748    04B2    A6 27              LDA #27H
749    04B4    B7 4B              STA MATH.1
750    04B6    CD 06 25           JSR MULWK22     ; multiply 1 percent by set point
751    04B9    B6 4C              LDA MATH.2
752    04BB    B1 3C              CMP COHB1.2     ; COMPARE INDEXED VALUE AGAINST CURRENT BLOOD LEVEL
753    04BD    22 12              BHI HH01FF      ; AND IF INDEXED VALUE IS GREATER, NO HEALTH HAZARD
754    04BF    25 0E              BLO HH1ON
755    04C1    B6 4B              LDA MATH.1
756    04C3    B1 3B              CMP COHB1.1
757    04C5    22 0A              BHI HH01FF
```

```
758    04C7    25 06                   BLO  HH1ON
759    04C9    B6 4A                   LDA  MATH.0
760    04CB    B1 3A                   CMP  COHB1.0
761    04CD    22 02                   BHI  HH01FF
762    04CF    99              HH1ON:  SEC
763    04D0    81                      RTS
764    04D1    98              HH01FF: CLC
765    04D2    81                      RTS
766
767                            ;-------------------------------
768    04D3    D6 04 FA        CHKLES: LDA  CMPTBL,X
769    04D6    B1 60                   CMP  WORK1
770    04D8    25 01                   BLO  LOOK1
771    04DA    81              GLOOK:  RTS
772    04DB    5C              LOOK1:  INCX
773    04DC    3A 3E                   DEC  WORK3
774    04DE    26 F3                   BNE  CHKLES
775    04E0    81                      RTS
776
777    04E1    B6 47           CHKHH:  LDA  CTMP.2
778    04E3    F1                      CMP  ,X
779    04E4    25 12                   BLO  CHKH1
780    04E6    22 0E                   BHI  CHKH2
781    04E8    B6 46                   LDA  CTMP.1
782    04EA    E1 01                   CMP  1,X
783    04EC    25 0A                   BLO  CHKH1
784    04EE    22 06                   BHI  CHKH2
785    04F0    B6 45                   LDA  CTMP.0
786    04F2    E1 02                   CMP  2,X
787    04F4    25 02                   BLO  CHKH1
788    04F6    98              CHKH2:  CLC
789    04F7    81                      RTS
790    04F8    99              CHKH1:  SEC
791    04F9    81                      RTS
792
793
794    04FA    31              CMPTBL: DB   49
795    04FB    52                      DB   82
796    04FC    7D                      DB   125
797    04FD    A7                      DB   167
798    04FE    C9                      DB   201
799    04FF    E0                      DB   224
800    0500    FF                      DB   255
801
802    0501    40 20 10 08 04  LEDTBL: DB   40H, 20H, 10H, 08H, 04H, 02H, 01H
       0506    02 01
803
804
805                            ;ELTBL: DB   001H, 011H, 070H         ;  7 %
806                            ;       DB   001H, 038H, 080H         ;  8 %
807                            ;       DB   001H, 05FH, 090H         ;  9 %
808                            ;       DB   001H, 086H, 0A0H         ; 10 %
809                            ;       DB   001H, 0ADH, 0B0H         ; 11 %
810                            ;       DB   001H, 0D4H, 0C0H         ; 12 %
811                            ;       DB   001H, 0FBH, 0D0H         ; 13 %
812                            ;       DB   002H, 022H, 0E0H         ; 14 %
813                            ;       DB   002H, 049H, 0F0H         ; 15 %
814                            ;       DB   002H, 071H, 000H         ; 16 %
815                            ;       DB   002H, 098H, 010H         ; 17 %
816                            ;       DB   002H, 0BFH, 020H         ; 18 %
817                            ;       DB   002H, 0E6H, 030H         ; 19 %
818                            ;       DB   003H, 00DH, 040H         ; 20 %
819                            ;       DB   003H, 034H, 050H         ; 21 %
820                            ;       DB   003H, 05BH, 060H         ; 22 %
821                            ;
822                            ;HB25:  DB   003H, 0DH, 090H           ; %COHB = 25.00
823                                    PAGE
824                            ;-------------------------------
825    0508    AE 10           BINBCD: LDX  #16             ; number of binary bits
to be converted
826    050A    A6 00                   LDA  #0
```

```
 827   050C    B7 25              STA BCD0
 828   050E    B7 26              STA BCD1     ; PRESET BCD REGISTERS
O ZERO
 829   0510    B7 27              STA BCD2
 830   0512    98          BINB1: CLC
 831   0513    39 4A              ROL MATH.0
 832   0515    39 4B              ROL MATH.1   ; rotate binary ms digit
 into carry
 833   0517    B6 25              LDA BCD0     ; add bcd digits to them
 selves ( bcd x 2)
 834   0519    B9 25              ADC BCD0     ; with carry from binary
 digits
 835   051B    CD 05 36           JSR DAA      ; decimal adjust result
 836   051E    B7 25              STA BCD0     ; and store.
 837   0520    B6 26              LDA BCD1     ; repeat for ms bcd digi
t
 838   0522    B9 26              ADC BCD1
 839   0524    CD 05 36           JSR DAA
 840   0527    B7 26              STA BCD1
 841   0529    24 07              BCC BINB2
 842   052B    A6 99              LDA #99H     ; on overflow set bcd to
 9999
 843   052D    B7 25              STA BCD0
 844   052F    B7 26              STA BCD1
 845   0531    81                 RTS
 846                        ;     LDA #05H     ; error 5 no longer exis
ts
 847                        ;     JSR SETFLT
 848   0532    5A          BINB2: DECX
 849   0533    26 DD              BNE BINB1    ; REPEAT UNTIL ALL 24 BI
TS ARE DONE
 850   0535    81                 RTS
 851
 852                        ;------------------------------------------
 853                        ; DAA - DECIMAL ADJUST ACCUMULATOR
 854                        ;------------------------------------------
 855                        ; AT ENTRY
 856                        ; A  --   RESULT OF PREVIOUS ADD OR ADC
 857                        ; CC --   RESULT OF PREVIOUS ADD OR ADC
 858                        ; AT EXIT
 859                        ; A  --   CORRECTED BCD NUMBERS
 860                        ; CC --   CARRY BIT READY FOR MULTIPLE BYTE PRECIS
ION ARITHMETIC
 861
 862   0536    25 04       DAA:   BCS DAAHAI   ; IF CARRY THEN ADJUST H
IGH DIGIT
 863   0538    A1 99              CMP #99H     ; DOUBLE OVERFLOW? (>99?
)
 864   053A    23 08              BLS DAALOW   ; NO, CHECK LOW DIGIT
 865   053C    40          DAAHAI: NEGA        ; AVOID CLOBBERING H-BIT
 BY
 866   053D    A0 60              SUB #60H     ; A + $60 = -(-A - $60)
 867   053F    40                 NEGA
 868                        ; THIS LAST ADJUSTMENT MEANS RETURN WITH CARRY S
ET
 869   0540    AD 02              BSR DAALOW
 870   0542    99                 SEC
 871   0543    81                 RTS
 872                        ; CHECK LOW DIGIT FOR OVERFLOW
 873   0544    28 03       DAALOW: BHCC DAANOO ; NO OVERFLOW DETECTED
 874   0546    AB 06              ADD #6       ; ADJUST FOR KNOWN OVERF
LOW
 875   0548    81                 RTS
 876   0549    AB 06       DAANOO: ADD #6      ; LOW DIGIT A-F?
 877   054B    29 02              BHCS DAARTS  ; BRANCH ADJUSTED IF COR
RECT ASSUMPTION
 878   054D    A0 06              SUB #6
 879   054F    81          DAARTS: RTS         ; TAH DAH!
 880
 881                        ;------------------------------------------
```

```
882  0550  02 02 0E        DMPCHK: BRSET 1,PORTC,NDMP
883  0553  19 02                   BCLR 4,PORTC        ; KILL i DURING DATA DUMP
884  0555  CD 0A D2                JSR CLRDLY
885  0558  03 02 03                BRCLR 1,PORTC,RJ
886  055B  CD 00 BB                JSR MEMCLR
887  055E  CD 0A 9B        RJ:     JSR DUMP
888  0561  81              NDMP:   RTS
889
890                        ;------------------------------------------------
891  0562  3F 59           BUTTON: CLR TBUTT           ; CLEAR BUTTON PRESS REC ORDER
892  0564  0D 03 04                BRCLR 6,PORTD,BDWN
893  0567  3F 5A           NOBUTT: CLR BTIMER
894  0569  98                      CLC
895  056A  81                      RTS
896  056B  A6 FA           BDWN:   LDA #250
897  056D  B7 5A                   STA BTIMER
898  056F  13 00                   BCLR 1,PORTA        ; KILL ANY BUZZ IN PROGRESS
899  0571  A6 02           BDWNA:  LDA #2
900  0573  B7 35                   STA TIMER           ; USE A 20 MILLISECOND SWITCH DEBOUNCE
901  0575  0C 03 24        BDWN1:  BRSET 6,PORTD,BDWN4
902  0578  B6 35                   LDA TIMER
903  057A  26 F9                   BNE BDWN1
904  057C  12 00                   BSET 1,PORTA        ; BEEP TO ACKNOWLEDGE
905  057E  A6 05                   LDA #5
906  0580  B7 35                   STA TIMER
907  0582  B6 35           BDWN2:  LDA TIMER
908  0584  26 FC                   BNE BDWN2
909  0586  13 00                   BCLR 1,PORTA
910  0588  B6 5A           BDWN3:  LDA BTIMER
911  058A  27 19                   BEQ TIMOUT
912  058C  0D 03 F9                BRCLR 6,PORTD,BDWN3 ; AWAIT SWITCH RELEASE
913  058F  A6 02                   LDA #2
914  0591  B7 35                   STA TIMER
915  0593  0D 03 F2        BDWN3A: BRCLR 6,PORTD,BDWN3 ; ENSURE SWITCH RELEASED FOR 20 MILLISECONDS
916  0596  B6 35                   LDA TIMER
917  0598  26 F9                   BNE BDWN3A
918  059A  3C 59                   INC TBUTT
919  059C  B6 5A           BDWN4:  LDA BTIMER
920  059E  27 05                   BEQ TIMOUT
921  05A0  0C 03 F9                BRSET 6,PORTD,BDWN4
922  05A3  20 CC                   BRA BDWNA
923  05A5  1B 02           TIMOUT: BCLR 5,PORTC
924  05A7  19 02                   BCLR 4,PORTC
925  05A9  B6 59                   LDA TBUTT
926  05AB  27 42                   BEQ BFAULT
927  05AD  1E 5D                   BSET 7,FLAG0
928  05AF  A1 04                   CMP #4
929  05B1  25 04                   BLO FIXB1
930  05B3  A6 04                   LDA #4
931  05B5  20 08                   BRA FIXB2
932  05B7  A1 02           FIXB1:  CMP #2
933  05B9  25 04                   BLO FIXB2
934  05BB  A6 02                   LDA #2
935  05BD  20 00                   BRA FIXB2
936  05BF  B7 59           FIXB2:  STA TBUTT
937  05C1  B7 60                   STA WORK1
938  05C3  A6 FA                   LDA #250
939  05C5  B7 5A                   STA BTIMER
940  05C7  A6 05           TBUZZ:  LDA #5
941  05C9  B7 35                   STA TIMER
942  05CB  12 00                   BSET 1,PORTA
943  05CD  B6 35           TBUZZ1: LDA TIMER
944  05CF  26 FC                   BNE TBUZZ1
945  05D1  13 00                   BCLR 1,PORTA
```

```
946    05D3    A6 05                       LDA  #5
947    05D5    B7 35                       STA  TIMER
948    05D7    B6 35          TBUZZ2:      LDA  TIMER
949    05D9    26 FC                       BNE  TBUZZ2
950    05DB    3A 60                       DEC  WORK1
951    05DD    26 E8                       BNE  TBUZZ
952    05DF    0B 5D 03       BOUT:        BRCLR 5,FLAG0,BOUT1
953    05E2    CD 02 61                    JSR  ERRDSP              ; REDISPLAY ERROR MESSAGE
954    05E5    3F 39          BOUT1:       CLR  LOFF.1
955    05E7    A6 01                       LDA  #1
956    05E9    B7 38                       STA  LOFF.0
957    05EB    3F 5A                       CLR  BTIMER
958    05ED    99                          SEC
959    05EE    81                          RTS
960    05EF                   BFAULT:
961    05EF    A6 06                       LDA  #06H
962    05F1    CD 07 4F                    JSR  SETFLT
963    05F4    20 E9                       BRA  BOUT
964                                        PAGE
965                           ; MUL16 IS A 2 BYTE BY 2 BYTE MULTIPLY
966                           ; MUL23 IS A 2 BY THREE BYTE MULTIPLY
967                           ; ON ENTRY, MULTIPLIER IS IN MATH.0-MATH.1 (MATH.0-MATH.2 FOR MUL23), X POINTS
968                           ; TO MULTIPLICAND
969                           ; ON EXIT, 5 BYTE RESULT IS IN MATH.0-MATH.4, LS TO MS
970
971    05F6    3F 4C          MUL16:       CLR  MATH.2
972    05F8    3F 4D          MUL23:       CLR  MATH.3
973    05FA    A6 21          MUL24:       LDA  #33
974    05FC    B7 60                       STA  WORK1
975    05FE    3F 4E                       CLR  MATH.4
976    0600    3F 4F                       CLR  MATH.5
977    0602    98                          CLC
978    0603    20 11                       BRA  ROT1
979    0605    24 0B          NXT:         BCC  ROTAT
980    0607    B6 4E                       LDA  MATH.4
981    0609    FB                          ADD  ,X
982    060A    B7 4E                       STA  MATH.4
983    060C    B6 4F                       LDA  MATH.5
984    060E    E9 01                       ADC  1,X
985    0610    B7 4F                       STA  MATH.5
986
987    0612    36 4F          ROTAT:       ROR  MATH.5
988    0614    36 4E                       ROR  MATH.4
989    0616    36 4D          ROT1:        ROR  MATH.3
990    0618    36 4C                       ROR  MATH.2
991    061A    36 4B                       ROR  MATH.1
992    061C    36 4A                       ROR  MATH.0
993    061E    3A 60                       DEC  WORK1
994    0620    26 E3                       BNE  NXT
995    0622    81                          RTS
996
997                           ;--------------------------------
998                           ; MULWK2 MULTIPLIES MATH.0-MATH.3 BY WORK2 ( A 4 BY 1 BYTE MULTIPLY )
999    0623                   MULWK21:
1000   0623    3F 4B                       CLR  MATH.1      ; 1 X 1
1001   0625                   MULWK22:
1002   0625    3F 4C                       CLR  MATH.2      ; 2 X 1
1003   0627                   MULWK23:
1004   0627    3F 4D                       CLR  MATH.3      ; 1 X 1
1005   0629    A6 21          MULWK2:      LDA  #33
1006   062B    B7 60                       STA  WORK1
1007   062D    3F 4E                       CLR  MATH.4
1008   062F    98                          CLC
1009   0630    20 0A                       BRA  MLWK2C
1010   0632    24 06          MLWK2A:      BCC  MLWK2B
1011   0634    B6 5F                       LDA  WORK2
1012   0636    BB 4E                       ADD  MATH.4
```

```
1013   0638   B7 4E              STA  MATH.4
1014   063A   36 4E    MLWK2B:   ROR  MATH.4
1015   063C   36 4D    MLWK2C:   ROR  MATH.3
1016   063E   36 4C              ROR  MATH.2
1017   0640   36 4B              ROR  MATH.1
1018   0642   36 4A              ROR  MATH.0
1019   0644   3A 60              DEC  WORK1
1020   0646   26 EA              BNE  MLWK2A
1021   0648   81                 RTS
1022
1023                    ;----------------------------
1024                    ; DIVIDE IS A 4 BYTE BY 2 BYTE DIVIDE ROUTINE
1025                    ; DIV52 IS A 5 BY 2 BYTE DIVIDE
1026                    ; ON ENTRY, MATH.0-MATH.4 CONTAINS DIVIDEND, X POINTS TO 2 BYTE DIVISOR
1027                    ; ON EXIT, QUOTIENT IS IN MATH.0-MATH.4, REMAINDER IN MATH.4-MATH.5
1028
1029   0649   3F 4E    DIVIDE:   CLR  MATH.4
1030   064B   A6 29    DIV52:    LDA  #41
1031   064D   B7 60              STA  WORK1
1032   064F   3F 4F              CLR  MATH.5
1033   0651   3F 5F              CLR  MATH.6
1034   0653   3A 60    DIVA:     DEC  WORK1
1035   0655   26 01              BNE  DIVB
1036   0657   81                 RTS
1037   0658   38 4A    DIVB:     LSL  MATH.0
1038   065A   39 4B              ROL  MATH.1
1039   065C   39 4C              ROL  MATH.2
1040   065E   39 4D              ROL  MATH.3
1041   0660   39 4E              ROL  MATH.4
1042   0662   39 4F              ROL  MATH.5
1043   0664   39 5F              ROL  MATH.6
1044   0666   25 09              BCS  DIVC
1045   0668   B6 4F              LDA  MATH.5
1046   066A   F0                 SUB  ,X
1047   066B   B6 5F              LDA  MATH.6
1048   066D   E2 01              SBC  1,X
1049   066F   25 E2              BCS  DIVA
1050   0671   B6 4F    DIVC:     LDA  MATH.5
1051   0673   F0                 SUB  ,X
1052   0674   B7 4F              STA  MATH.5
1053   0676   B6 5F              LDA  MATH.6
1054   0678   E2 01              SBC  1,X
1055   067A   B7 5F              STA  MATH.6
1056   067C   3C 4A              INC  MATH.0
1057   067E   20 D3              BRA  DIVA
1058
1059                              PAGE
1060                    ;----------------------------
1061   0680   A6 46    TIMINT:   LDA  #70
1062   0682   B7 08              STA  TDR
1063   0684   1F 09              BCLR 7,TCR
1064
1065                    ;-------- ADDED TO MAKE DISPLAY UPDATES MORE RESPONSIVE ----------
1066   0686   2E 0D              BIL  CHKLO          ; check status of display switch
1067   0688   0C 5D 15           BRSET 6,FLAG0,NOCHNG  ; if old = current, no change
1068   068B   3A 5B              DEC  DSPBNC         ; check debounce timer
1069   068D   26 15              BNE  SWTEXT         ; if not zero, wait and see
1070   068F   1C 5D              BSET 6,FLAG0        ; New display
1071   0691   1A 5C              BSET 5,FLAG1
1072   0693   20 0B              BRA  NOCHNG
1073   0695   0D 5D 08 CHKLO:    BRCLR 6,FLAG0,NOCHNG  ; Do same thing for low input
1074   0698   3A 5B              DEC  DSPBNC
1075   069A   26 08              BNE  SWTEXT
1076   069C   1D 5D              BCLR 6,FLAG0
```

```
1077  069E  1A 5C                BSET 5,FLAG1
1078  06A0  A6 04        NOCHNG: LDA #4
1079  06A2  B7 5B                STA DSPBNC
1080  06A4               SWTEXT:
1081
1082                     ;----------------------------------------

1083  06A4  B6 35                LDA TIMER
1084  06A6  27 02                BEQ TIME
1085  06A8  3A 35                DEC TIMER
1086  06AA  B6 50        TIME:   LDA TIME.0
1087  06AC  27 02                BEQ TIMEA
1088  06AE  3A 50                DEC TIME.0
1089  06B0               TIMEA:
1090  06B0  05 5C 3D     BUZZZ:  BRCLR 2,FLAG1,BUZZ3      ; Buzzer is currently off
1091  06B3  B6 5E        BUZZ1:  LDA LBUZZ
1092  06B5  27 06                BEQ BUZZ2                ; BUZZ TIMER ELAPSED?
1093  06B7  3A 5E                DEC LBUZZ
1094  06B9  14 5C                BSET 2,FLAG1
1095  06BB  20 43                BRA UPDATE
1096
1097  06BD  0B 5D 07     BUZZ2:  BRCLR 5,FLAG0,HHBUZZ
1098                     ;++++++++ TEST ONLY +++++++++
1099  06C0  07 02 04             BRCLR 3,PORTC,HHBUZZ     ; DISABLE FAULT BUZZER BY SWITCH
1100                     ;++++++++ TEST ONLY +++++++++
1101  06C3  AE 00                LDX #0                   ; FAULT BUZZER
1102  06C5  20 1A                BRA BUZZ2A
1103  06C7  09 5D 15     HHBUZZ: BRCLR 4,FLAG0,KILBUZ
1104  06CA  03 5D 12             BRCLR 1,FLAG0,KILBUZ
1105  06CD  05 5D 04             BRCLR 2,FLAG0,SHCHK
1106  06D0  AE 03                LDX #3                   ; MM BUZZER
1107  06D2  20 0D                BRA BUZZ2A
1108  06D4  06 5D 04     SHCHK:  BRSET 3,FLAG0,SHBUZZ
1109  06D7  AE 06                LDX #6                   ; LL BUZZER
1110  06D9  20 06                BRA BUZZ2A
1111  06DB  AE 09        SHBUZZ: LDX #9                   ; SH BUZZER
1112  06DD  20 02                BRA BUZZ2A
1113  06DF  AE 0C        KILBUZ: LDX #12                  ; NO BUZZER
1114  06E1  D6 07 2E     BUZZ2A: LDA BUZTBL,X
1115  06E4  B7 5E                STA LBUZZ
1116  06E6  D6 07 2F             LDA BUZTBL+1,X
1117  06E9  B7 39                STA LOFF.1
1118  06EB  D6 07 30             LDA BUZTBL+2,X
1119  06EE  B7 38                STA LOFF.0
1120  06F0  B6 38        BUZZ3:  LDA LOFF.0
1121  06F2  A0 01                SUB #1
1122  06F4  B7 38                STA LOFF.0
1123  06F6  B6 39                LDA LOFF.1
1124  06F8  A2 00                SBC #0
1125  06FA  B7 39                STA LOFF.1
1126  06FC  25 B5                BCS BUZZ1
1127  06FE  15 5C                BCLR 2,FLAG1
1128
1129  0700  0E 5D 11     UPDATE: BRSET 7,FLAG0,UPDAT2     ; NO BUZZER IN TEST MODE
1130  0703  B6 5A                LDA BTIMER
1131  0705  27 04                BEQ UPDAT
1132  0707  3A 5A                DEC BTIMER
1133  0709  20 09                BRA UPDAT2
1134  070B  04 5C 04     UPDAT:  BRSET 2,FLAG1,UPDAT1
1135  070E  13 00                BCLR 1,PORTA
1136  0710  20 02                BRA UPDAT2
1137  0712  12 00        UPDAT1: BSET 1,PORTA
1138  0714  B6 36        UPDAT2: LDA SECNT.0              ; CHECK UPDATE TIMER
1139  0716  A0 01                SUB #1
1140  0718  B7 36                STA SECNT.0
1141  071A  B6 37                LDA SECNT.1
1142  071C  A2 00                SBC #0
1143  071E  B7 37                STA SECNT.1
```

```
1144   0720   25 01              BCS  NEWTIM
1145   0722   80                 RTI
1146   0723              NEWTIM:
1147   0723   10 5D              BSET 0,FLAG0      ; UPDATE DISPLAY
1148   0725   B6 33              LDA  NXTIM.0
1149   0727   B7 36              STA  SECNT.0
1150   0729   B6 34              LDA  NXTIM.1
1151   072B   B7 37              STA  SECNT.1
1152   072D   80       BAIL:     RTI               ; AND RETURN FOR
M INTERRUPT
1153
1154                             ;----------------------
1155   072E   64 00 64  BUZTBL:  DB  064H, 000H, 064H  ; FAULT BUZZER V
ALUES
1156   0731   64 01 90           DB  064H, 001H, 090H  ; MM BUZZER VALU
ES
1157   0734   64 03 84           DB  064H, 003H, 084H  ; LL BUZZER VALU
ES
1158   0737   64 00 00           DB  064H, 000H, 000H  ; SH BUZZER VALU
ES
1159   073A   00 00 64           DB  000H, 000H, 064H  ; NO BUZZER VALU
ES
1160
1161                             PAGE
1162   073D   A6 32    TTOG:     LDA  #50           ; TOGGLE TEST LAMP
1163   073F   B7 35              STA  TIMER
1164   0741   0B 00 03           BRCLR 5,PORTA,TTOG1
1165   0744   1B 00              BCLR 5,PORTA
1166   0746   81                 RTS
1167   0747   1A 00    TTOG1:    BSET 5,PORTA
1168   0749   81                 RTS
1169
1170                             ;----------------------
1171   074A   AD 03    TFAULT:   BSR  SETFLT
1172   074C   CC 07 9C           JMP  TWAT
1173
1174                             ;----------------------
1175   074F   1C 00    SETFLT:   BSET 6,PORTA       ; SET FAULT LAMP
1176   0751   1A 5D              BSET 5,FLAG0       ; AND FAULT FLAG
1177   0753   B7 22              STA  ERRCOD
1178   0755   1C 5C              BSET 6,FLAG1       ; SET FAULT DISPLAY INDI
CATOR
1179   0757   1A 5C              BSET 5,FLAG1       ; REQUEST DISPLAY UPDATE
1180   0759   CD 03 E3           JSR  KILIND        ; KILL INDICATORS
1181   075C   81                 RTS
1182
1183                             ;----------------------
1184   075D   9B       PWRUP:    SEI      ; KILL TIMER
1185   075E   1E 5D              BSET 7,FLAG0
1186   0760   1B 5D              BCLR 5,FLAG0       ; KILL FAULT BIT
1187   0762   19 02              BCLR 4,PORTC       ; KILL SENSOR CURRENT
1188   0764   A6 00              LDA  #0
1189   0766   B7 00              STA  PORTA         ; AND LAMPS
1190   0768   B7 01              STA  PORTB         ; AND BUZZERS
1191   076A   A6 F4              LDA  #<500
1192   076C   B7 36              STA  SECNT.0
1193   076E   A6 01              LDA  #>500
1194   0770   B7 37              STA  SECNT.1
1195   0772   A6 70              LDA  #<6000
1196   0774   B7 33              STA  NXTIM.0
1197   0776   A6 17              LDA  #>6000
1198   0778   B7 34              STA  NXTIM.1
1199   077A   9A                 CLI
1200
1201   077B   CD 04 9C           JSR  READ2
1202   077E   A1 FE              CMP  #0FEH
1203   0780   A6 07              LDA  #07H
1204   0782   25 C6              BLO  TFAULT
1205   0784   CD 04 A0           JSR  READ3
1206   0787   A1 01              CMP  #1
1207   0789   A6 08              LDA  #08H
1208   078B   22 B0              BHI  TFAULT
1209   078D   CD 04 98           JSR  READ1
```

```
1210  0790  A1 3C              CMP  #60
1211  0792  A6 09              LDA  #09H
1212  0794  25 B4              BLO  TFAULT
1213  0796  A1 E1              CMP  #225
1214  0798  A6 10              LDA  #10H
1215  079A  22 AE              BHI  TFAULT
1216  079C  B6 35       TWAT:  LDA  TIMER
1217  079E  26 03              BNE  TWAT1
1218  07A0  CD 07 3D           JSR  TTOG
1219  07A3  01 5D F6    TWAT1: BRCLR 0,FLAG0,TWAT
1220  07A6  11 5D              BCLR 0,FLAG0
1221
1222  07A8
1223  07A8  1F 5D       PWROUT: BCLR 7,FLAG0
1224  07AA  1A 00              BSET 5,PORTA        ; SET TEST LAMP
1225  07AC  CD 09 3F           JSR  ICYCLE
1226  07AF  1B 00              BCLR 5,PORTA        ; CLEAR TEST LAMP
1227  07B1  CD 02 D3           JSR  GETCOC
1228  07B4  CD 03 80           JSR  HBCOC
1229  07B7  CC 01 25           JMP  OCO
1230
1231                          ;--------------------
1232                                  PAGE
1233                          ;--------------------
1234  07BA              EOS:
1235  07BA  01 5D FD    EOS1:  BRCLR 0,FLAG0,EOS
1236  07BD  11 5D              BCLR 0,FLAG0
1237  07BF  81                 RTS
1238
1239                          ;--------------------
1240  07C0  CD 04 9C    LEDCHK: JSR READ2
1241  07C3  A1 CD              CMP  #MAXLED
1242  07C5  22 05              BHI  BLED
1243  07C7  A1 66              CMP  #MINLED
1244  07C9  25 01              BLO  BLED
1245  07CB  81          GLED:  RTS
1246  07CC  B6 01       BLED:  LDA  PORTB
1247  07CE  A4 7F              AND  #7FH
1248  07D0  27 F9              BEQ  GLED
1249  07D2  A6 11              LDA  #11H
1250  07D4  CC 07 4F           JMP  SETFLT       ; BAD LED
1251
1252                          ;--------------------
1253  07D7  A6 07       LMPCHK: LDA #7
1254  07D9  B7 60              STA  WORK1
1255  07DB  5F                 CLRX
1256  07DC  3F 3E              CLR  WORK3
1257  07DE  3F 3F              CLR  WORK4
1258  07E0  B6 00              LDA  PORTA
1259  07E2  46          LMPC1: RORA
1260  07E3  24 12              BCC  LMPC2
1261  07E5  B7 5F              STA  WORK2        ; SAVE ACC
1262  07E7  D6 08 13           LDA  ILMP,X
1263  07EA  BB 3E              ADD  WORK3        ; ADD IN APPROPRIATE MIN CURRENT
1264  07EC  B7 3E              STA  WORK3
1265  07EE  D6 08 14           LDA  ILMP+1,X
1266  07F1  BB 3F              ADD  WORK4        ; ADD IN APPROPRIATE MAX CURRENT
1267  07F3  B7 3F              STA  WORK4
1268  07F5  B6 5F              LDA  WORK2        ; RESTORE ACC
1269  07F7  5C          LMPC2: INCX
1270  07F8  5C                 INCX
1271  07F9  3A 60              DEC  WORK1
1272  07FB  26 E5              BNE  LMPC1
1273  07FD  CD 04 A0           JSR  READ3        ; READ IN ACTUAL LAMP CURRENT
1274  0800  B1 3E              CMP  WORK3        ; COMPARE AGAINST MIN
1275  0802  25 05              BLO  BLMP1        ; IF LOW, NO GOOD
1276  0804  B1 3F              CMP  WORK4        ; COMPARE AGAINST MAX
1277  0806  22 06              BHI  BLMP2        ; IF HIGH, NO GOOD
```

```
1278    0808    81                          RTS
1279
1280    0809    A6 12           BLMP1:      LDA  #12H
1281    080B    CC 07 4F                    JMP  SETFLT
1282    080E    A6 13           BLMP2:      LDA  #13H
1283    0810    CC 07 4F                    JMP  SETFLT
1284
1285                                        ;lamp i   min  max   lamp
1286    0813    06 10           ILMP:       DB   6,   16  ; health hazard
1287    0815    01 04                       DB   1,   4   ; buzzer
1288    0817    03 08                       DB   3,   8   ; fault
1289    0819    03 08                       DB   3,   8   ; test
1290    081B    03 08                       DB   3,   8   ; short exposure
1291    081D    03 08                       DB   3,   8   ; medium exposure
1292    081F    03 08                       DB   3,   8   ; long exposure
1293
1294                                        ;----------------------
1295    0821    CD 07 4F        TFON:       JSR  SETFLT
1296    0824    CC 08 64                    JMP  TWAIT
1297
1298                                        ;----------------------
1299    0827    9B              TEST:       SEI       ; KILL TIMER
1300    0828    1E 5D                       BSET 7,FLAG0
1301    082A    1B 5D                       BCLR 5,FLAG0        ; KILL FAULT BIT
1302    082C    19 02                       BCLR 4,PORTC        ; KILL SENSOR CURRENT
1303    082E    A6 00                       LDA  #0
1304    0830    B7 00                       STA  PORTA          ; AND LAMPS
1305    0832    B7 01                       STA  PORTB          ; AND BUZZERS
1306    0834    A6 64                       LDA  #<100
1307    0836    B7 36                       STA  SECNT.0
1308    0838    B7 33                       STA  NXTIM.0
1309    083A    A6 00                       LDA  #>100
1310    083C    B7 37                       STA  SECNT.1
1311    083E    B7 34                       STA  NXTIM.1
1312    0840    9A                          CLI
1313
1314    0841    CD 04 9C                    JSR  READ2
1315    0844    A1 FE                       CMP  #0FEH
1316    0846    A6 07                       LDA  #07H
1317    0848    25 D7                       BLO  TFON
1318    084A    CD 04 A0                    JSR  READ3
1319    084D    A1 01                       CMP  #1
1320    084F    A6 08                       LDA  #08H
1321    0851    22 CE                       BHI  TFON
1322    0853    CD 04 98                    JSR  READ1
1323    0856    B7 20                       STA  20H            ; SAVE TCV
1324    0858    A1 3C                       CMP  #60
1325    085A    A6 09                       LDA  #09H
1326    085C    25 C3                       BLO  TFON
1327    085E    A1 E1                       CMP  #225
1328    0860    A6 10                       LDA  #10H
1329    0862    22 BD                       BHI  TFON
1330    0864    3F 57           TWAIT:      CLR  STATE
1331    0866    CD 07 BA                    JSR  EOS
1332    0869    BE 57           STAT:       LDX  STATE
1333    086B    D6 09 D6                    LDA  STATBL,X
1334    086E    B7 00                       STA  PORTA
1335    0870    D6 09 D7                    LDA  STATBL+1,X
1336    0873    B7 01                       STA  PORTB
1337    0875    CD 07 BA                    JSR  EOS
1338    0878    CD 07 C0                    JSR  LEDCHK
1339    087B    CD 07 D7                    JSR  LMPCHK
1340    087E    CD 09 F8                    JSR  PROCHK         ; SAVE A/D DATA FOR PROD
. TESTING
1341    0881    3C 57                       INC  STATE
1342    0883    3C 57                       INC  STATE
1343    0885    B6 57                       LDA  STATE
1344    0887    A1 20                       CMP  #32
1345    0889    25 DE                       BLO  STAT
1346
1347    088B    3F 00                       CLR  PORTA
1348    088D    3F 01                       CLR  PORTB
```

```
1349    088F    0B 5D 02            BRCLR 5,FLAG0,OKDISP
1350    0892    1C 00               BSET 6,PORTA        ; SET ERROR LAMP
1351    0894    A6 70       OKDISP: LDA #<6000
1352    0896    B7 33               STA NXTIM.0
1353    0898    A6 17               LDA #>6000
1354    089A    B7 34               STA NXTIM.1
1355    089C    CD 07 BA            JSR EOS
1356
1357    089F    B6 59               LDA TBUTT
1358    08A1    A1 01               CMP #1
1359    08A3    22 07               BHI TEST2
1360    08A5    1F 5D       TSTOVR: BCLR 7,FLAG0        ; CLEAR TEST FLAG
1361    08A7    3F 59               CLR TBUTT
1362    08A9    CC 01 25            JMP 0C0
1363    08AC    A1 03       TEST2:  CMP #3
1364    08AE    22 08               BHI TEST4
1365    08B0    CD 09 B1            JSR CLEAR           ; CLEAR MEMORY
1366    08B3    3F 59               CLR TBUTT
1367    08B5    CC 07 A8            JMP PWROUT
1368                        ;       BRA TSTOVR
1369
1370    08B8    1A 00       TEST4:  BSET 5,PORTA        ; SET TEST MODE FLAGS
1371    08BA    1F 5D               BCLR 7,FLAG0
1372    08BC    CD 09 B1            JSR CLEAR
1373    08BF    CD 09 3F            JSR ICYCLE
1374    08C2    11 5D               BCLR 0,FLAG0
1375    08C4    1A 02               BSET 5,PORTC                ; TURN ON HIGH CURRENT
1376    08C6    18 02               BSET 4,PORTC
1377
1378    08C8    CD 02 D3            JSR GETCOC
1379
1380    08CB    B6 31               LDA COC1.0
1381    08CD    B7 4A               STA MATH.0
1382    08CF    B6 32               LDA COC1.1
1383    08D1    B7 4B               STA MATH.1
1384    08D3    A6 0A               LDA #10
1385    08D5    B7 5F               STA WORK2
1386    08D7    CD 06 25            JSR MULWK22         ; MULTIPLY COC BY 10
1387
1388    08DA    B6 4A               LDA MATH.0
1389    08DC    B7 31               STA COC1.0
1390    08DE    B6 4B               LDA MATH.1
1391    08E0    B7 32               STA COC1.1
1392
1393                        ;++++++++++++++++++++++++
1394    08E2    B6 4C               LDA MATH.2
1395    08E4    26 1D               BNE IDXOVR          ; get index corresponding to new CoC value
1396
1397    08E6    A6 00               LDA #0
1398    08E8    B7 60               STA WORK1
1399    08EA    BE 60       FNDIDX: LDX WORK1
1400    08EC    58                  LSLX
1401    08ED    25 20               BCS FIDXHI
1402    08EF    B6 4B               LDA MATH.1
1403    08F1    D1 0D 16            CMP COCTBL,X
1404    08F4    22 09               BHI IDXNXT
1405    08F6    25 27               BLO GIDX10
1406    08F8    B6 4A               LDA MATH.0
1407    08FA    D1 0D 17            CMP COCTBL+1,X
1408    08FD    23 20               BLS GIDX10
1409    08FF    3C 60       IDXNXT: INC WORK1
1410    0901    26 E7               BNE FNDIDX
1411    0903    A6 FF       IDXOVR: LDA #0FFH
1412    0905    B7 60               STA WORK1
1413    0907    A6 FF               LDA #0FFH
1414    0909    B7 31               STA COC1.0
1415    090B    B7 32               STA COC1.1
1416    090D    20 10               BRA GIDX10
1417
```

```
1418   090F   B6 4B        FIDXHI: LDA MATH.1
1419   0911   D1 0E 16             CMP COCTBL+256,X
1420   0914   22 E9                BHI IDXNXT
1421   0916   25 07                BLO GIDX10
1422   0918   B6 4A                LDA MATH.0
1423   091A   D1 0E 17             CMP COCTBL+257,X
1424   091D   22 E0                BHI IDXNXT
1425   091F
1426   091F   B6 60        GIDX10: LDA WORK1
1427   0921   B7 2D                STA COCIDX
1428                        ;++++++++++++++++++++++
1429
1430   0923   CD 03 80             JSR HBCOC          ; AND PROCESS ACCORDINGLY
1431   0926   CD 03 E0             JSR INDCTR
1432   0929   CD 01 E6             JSR LCDDSP
1433   092C   CD 09 3F             JSR ICYCLE
1434   092F   CD 09 B1             JSR CLEAR
1435   0932   1F 5D                BCLR 7,FLAG0
1436   0934   1B 00                BCLR 5,PORTA       ; CLEAR TEST LAMP
1437   0936   CD 02 D3             JSR GETCOC
1438   0939   CD 03 80             JSR HBCOC
1439   093C   CC 08 A5             JMP TSTOVR
1440
1441                        ;----------------------
1442   093F                ICYCLE:
1443   093F   A6 B8        TACO:   LDA #<3000         ; SET UP TIMER FOR 90 SECONDS OF LOW CURRENT
1444   0941   B7 33                STA NXTIM.0
1445   0943   A6 0B                LDA #>3000         ; <ACTUALLY 3 CYCLES OF 30 SECONDS>
1446   0945   B7 34                STA NXTIM.1
1447   0947   11 5D                BCLR 0,FLAG0
1448   0949   1A 02                BSET 5,PORTC       ; TURN ON HIGH CURRENT
1449   094B   18 02                BSET 4,PORTC
1450   094D   CD 05 50     TACO1:  JSR DMPCHK
1451   0950   0B 5C 03             BRCLR 5,FLAG1,DSP1E
1452   0953   CD 01 E6             JSR LCDDSP
1453   0956                DSP1E:
1454   0956   01 5D F4     TWAIT2: BRCLR 0,FLAG0,TACO1 ; HIGH CURRENT FOR 60 SECONDS
1455   0959   CD 04 94             JSR READ0
1456   095C   B7 10                STA 10H            ; SAVE HI i FOR PROD TEST
1457   095E   AE 86                LDX #HICHKI
1458   0960   CD 0A DC             JSR CHKI
1459   0963   1B 02                BCLR 5,PORTC
1460   0965   11 5D                BCLR 0,FLAG0       ; THEN LOW FOR 90
1461   0967   CD 09 A2             JSR LOW21
1462
1463   096A   CD 04 94             JSR READ0
1464   096D   B7 11                STA 11H            ; SAVE LOW i FOR PROD TEST
1465   096F   AE 88                LDX #LOCHKI
1466   0971   CD 0A DC             JSR CHKI
1467
1468   0974   CD 02 7C             JSR TSTVS          ; TEST SENSOR VOLTAGE
1469
1470   0977   CD 09 A2             JSR LOW21
1471                        ;LOW23:
1472                        ;       JSR DMPCHK
1473                        ;       BRCLR 5,FLAG1,DSP1G
1474                        ;       JSR LCDDSP
1475                        ;DSP1G:
1476                        ;LOW24: BRCLR 0,FLAG0,LOW23  ; SECOND 30 SECOND PERIOD
1477                        ;       BCLR 0,FLAG0
1478   097A
1479   097A   CD 02 7C             JSR TSTVS          ; TEST SENSOR VOLTAGE
```

```
1480   097D   A6 19              LOW25:  LDA #25
1481   097F   B7 33                      STA NXTIM.0
1482   0981   3F 34                      CLR NXTIM.1
1483   0983   CD 09 A2                   JSR LOW21
1484                             ;TAC1:
1485                             ;          JSR DMPCHK
1486                             ;          BRCLR 5,FLAG1,DSP1H
1487                             ;          JSR LCDDSP
1488   0986                      DSP1H:
1489                             ;TWAIT3:    BRCLR 0,FLAG0,TAC1      ; 3RD AN
D FINAL 30 SECOND PERIOD
1490                                                                ; WAIT 25 MILLIS
ECONDS
1491   0986   19 02                      BCLR 4,PORTC               ; WITH CURRENT O
FF
1492                             ;         BCLR 0,FLAG0
1493   0988   A6 70                      LDA #<6000
1494   098A   B7 33                      STA NXTIM.0
1495   098C   A6 17                      LDA #>6000
1496   098E   B7 34                      STA NXTIM.1                ; SET OF TIMER F
OR 60 SECONDS
1497   0990   01 5D FD           TAC1A:  BRCLR 0,FLAG0,TAC1A        ; THEN SAMPLE
1498   0993   11 5D                      BCLR 0,FLAG0
1499                             ; READ A/D VALUES
1500   0995   CD 04 94                   JSR READ0
1501   0998   B7 30                      STA VSENS
1502   099A   B7 21                      STA 21H                    ; SAVE Vs
1503   099C   CD 04 98                   JSR READ1
1504   099F   B7 3D                      STA TEMP
1505
1506   09A1   81                         RTS
1507                             ;-----------------------
1508   09A2                      LOW21:
1509   09A2   CD 05 50                   JSR DMPCHK
1510   09A5   0B 5C 03                   BRCLR 5,FLAG1,DSP1F
1511   09A8   CD 01 E6                   JSR LCDDSP
1512   09AB                      DSP1F:
1513   09AB   01 5D F4           LOW22:  BRCLR 0,FLAG0,LOW21        ; FIRST 30 SECON
D PERIOD
1514   09AE   11 5D                      BCLR 0,FLAG0
1515   09B0   81                         RTS
1516
1517                             ;-----------------------
1518   09B1   3F 55              CLEAR:  CLR COCHB
1519   09B3   3F 40                      CLR COHB0.0
1520   09B5   3F 41                      CLR COHB0.1
1521   09B7   3F 42                      CLR COHB0.2
1522   09B9   3F 3A                      CLR COHB1.0
1523   09BB   3F 3B                      CLR COHB1.1
1524   09BD   3F 3C                      CLR COHB1.2
1525
1526   09BF   9B                         SEI
1527   09C0   B6 5D                      LDA FLAG0
1528   09C2   A4 E1                      AND #0E1H
1529   09C4   B7 5D                      STA FLAG0
1530
1531   09C6   A6 64                      LDA #64H
1532   09C8   3F 5E                      CLR LBUZZ
1533   09CA   3F 39                      CLR LOFF.1
1534   09CC   B7 38                      STA LOFF.0
1535   09CE   9A                         CLI
1536
1537   09CF   3F 31                      CLR COC1.0
1538   09D1   3F 32                      CLR COC1.1
1539   09D3   3F 2D                      CLR COCIDX
1540
1541                             ;         CLR CF.0
1542                             ;         CLR CF.1
1543
1544   09D5   81                         RTS
1545
1546                             ;-----------------------
1547                             ;         PORTA    PORTB
```

```
1548    09D6                    STATBL:
1549    09D6    20 00                   DB  20H,    00H
1550    09D8    02 00                   DB  02H,    00H
1551    09DA    20 01                   DB  20H,    01H
1552    09DC    00 01                   DB  00H,    01H
1553    09DE    21 02                   DB  21H,    02H
1554    09E0    01 02                   DB  01H,    02H
1555    09E2    24 04                   DB  24H,    04H
1556    09E4    04 04                   DB  04H,    04H
1557    09E6    28 08                   DB  28H,    08H
1558    09E8    08 08                   DB  08H,    08H
1559    09EA    30 10                   DB  30H,    10H
1560    09EC    10 10                   DB  10H,    10H
1561    09EE    20 20                   DB  20H,    20H
1562    09F0    00 20                   DB  00H,    20H
1563    09F2    60 40                   DB  60H,    40H
1564    09F4    40 40                   DB  40H,    40H
1565    09F6    00 00                   DB  00H,    00H
1566                                    PAGE
1567                            ;------------------
1568    09F8    BE 57           PROCHK: LDX STATE            ; PRODUCTION TEST MODE STATUS CHK
1569    09FA    54                      LSRX
1570    09FB    D6 0A 0F                LDA TLATBL,X
1571    09FE    97                      TAX
1572    09FF    CD 04 A0                JSR READ3
1573    0A02    F7                      STA 0,X
1574    0A03                    CHKLEDS:
1575    0A03    BE 57                   LDX STATE
1576    0A05    54                      LSRX
1577    0A06    D6 0A 20                LDA LDATBL,X
1578    0A09    97                      TAX
1579    0A0A    CD 04 9C                JSR READ2
1580    0A0D    F7                      STA 0,X
1581    0A0E    81              PROVR:  RTS
1582
1583                            ;------------------
1584                            ;TLTBL: DB 0,1,0,0,0,1,0,1
1585                            ;       DB 0,1,0,1,1,0,0,1
1586                            ;       DB 0
1587                            ;LDTBL: DB 0,0,0,1,0,1,0,1
1588                            ;       DB 0,1,0,1,1,0,0,1
1589                            ;       DB 0
1590
1591    0A0F    28 19 28 28 28  TLATBL: DB 28H, 19H, 28H, 28H, 28H, 1AH, 28H, 1BH
        0A14    1A 28 1B
1592    0A17    28 1C 28 1D 1E          DB 28H, 1CH, 28H, 1DH, 1EH, 28H, 28H, 1FH
        0A1C    28 28 1F
1593    0A1F    28                      DB 28H
1594
1595    0A20    28 28 28 12 28  LDATBL: DB 28H, 28H, 28H, 12H, 28H, 13H, 28H, 14H
        0A25    13 28 14
1596    0A28    28 15 28 16 17          DB 28H, 15H, 28H, 16H, 17H, 28H, 28H, 18H
        0A2D    28 28 18
1597    0A30    28                      DB 28H
1598                                    PAGE
1599                            ;------------------
1600    0A31                    DISPLAY:
1601    0A31    AD 2A                   BSR DISCLR           ; clear display
1602    0A33    A6 80                   LDA #80H
1603    0A35    AE 01                   LDX #1
1604    0A37    AD 10                   BSR DIS1             ; SEND START BIT
1605    0A39    AE 00                   LDX #0               ; prepare index to send 5 digits
1606    0A3B    E6 28           DISCHR: LDA DISBUF,X
1607    0A3D    AD 06                   BSR DISPLY
1608    0A3F    5C                      INCX
1609    0A40    A3 05                   CPX #5
```

```
1610    0A42    26 F7              BNE DISCHR
1611    0A44    81                 RTS
1612
1613                        ;------------------------
1614                        ; DISPLY OUTPUTS THE ACCUMULATOR CONTENTS TO THE DISPLAY DRIVER
1615
1616    0A45    BF 60       DISPLY: STX WORK1        ; save index
1617    0A47    AE 08               LDX #8
1618    0A49    15 02       DIS1:   BCLR 2,PORTC     ; clear data line
1619    0A4B    48                  ASLA
1620    0A4C    24 02               BCC DIS2
1621    0A4E    14 02               BSET 2,PORTC     ; set data line if data bit is a 1
1622    0A50    10 02       DIS2:   BSET 0,PORTC     ; set display clock line
1623    0A52    9D                  NOP
1624    0A53    11 02               BCLR 0,PORTC     ; then drop it
1625    0A55    5A                  DECX
1626    0A56    26 F1               BNE DIS1         ; check for all bits sent
1627    0A58    BE 60               LDX WORK1        ; restore index
1628    0A5A    15 02               BCLR 2,PORTC     ; clear data line
1629    0A5C    81                  RTS
1630
1631                        ;------------------------
1632                        ;       DISCLR CLEARS THE DISPLAY BUFFER ON THE 5453. IT WILL MOST LIKELY
1633                        ;       not CLEAR THE DISPLAY
1634
1635    0A5D    BF 60       DISCLR: STX WORK1
1636    0A5F    15 02               BCLR 2,PORTC     ; clear display data line
1637    0A61    AE 24               LDX #36
1638    0A63    10 02       DISC1:  BSET 0,PORTC     ; raise dispay clock line
1639    0A65    9D                  NOP
1640    0A66    11 02               BCLR 0,PORTC     ; then lower it
1641    0A68    5A                  DECX
1642    0A69    26 F8               BNE DISC1
1643    0A6B    81                  RTS
1644
1645                        ;------------------------
1646    0A6C    AE 29       FILDSP: LDX #DISBUF
1647    0A6E    F7          FILDA:  STA ,X
1648    0A6F    5C                  INCX
1649    0A70    A3 2D               CPX #(DISBUF+5)
1650    0A72    26 FA               BNE FILDA
1651    0A74    81                  RTS
1652
1653                        ;------------------------
1654    0A75    44          LEFT:   LSRA
1655    0A76    44                  LSRA
1656    0A77    44                  LSRA
1657    0A78    44                  LSRA
1658    0A79    A4 0F       RIGHT:  AND #0FH
1659    0A7B    26 03               BNE RIGHTA
1660    0A7D    0F 5C 13            BRCLR 7,FLAG1,RIGHTB
1661    0A80    1E 5C       RIGHTA: BSET 7,FLAG1
1662    0A82    BF 60               STX WORK1
1663    0A84    BB 5F               ADD WORK2        ; ADD DIGIT INDEX
1664    0A86    97                  TAX
1665    0A87    B6 5F               LDA WORK2
1666    0A89    AB 0A               ADD #10          ; INCREMENT DIGIT INDEX TO NEXT SEGMENT MAP
1667    0A8B    B7 5F               STA WORK2
1668    0A8D    D6 00 91            LDA SEGTBL,X
1669    0A90    BE 60               LDX WORK1
1670    0A92    81                  RTS
1671                        ; RETURN A 0 (BLANK DIGIT)
1672    0A93    B6 5F       RIGHTB: LDA WORK2
1673    0A95    AB 0A               ADD #10          ; INCREMENT DIGIT INDEX
```

TO NEXT SEGMENT MAP
```
1674    0A97    B7 5F              STA WORK2
1675    0A99    4F                 CLRA
1676    0A9A    81                 RTS
1677
1678                        ;------------------------
1679                                PAGE
1680                        ;------------------------
1681    0A9B    AE 61       DUMP:   LDX #61H
1682    0A9D    F6          DUMP1:  LDA 0,X
1683    0A9E    AD 04               BSR DMPBYT
1684    0AA0    5A                  DECX
1685    0AA1    26 FA               BNE DUMP1
1686    0AA3    81                  RTS
1687
1688                        ;------------------------
1689    0AA4    BF 60       DMPBYT: STX WORK1          ; save index
1690    0AA6    AE 08               LDX #8
1691    0AA8    15 02       DMPB1:  BCLR 2,PORTC
1692    0AAA    48                  ASLA
1693    0AAB    24 02               BCC DMPB2
1694    0AAD    14 02               BSET 2,PORTC
1695    0AAF    AD 0E       DMPB2:  BSR TIMDLY
1696    0AB1    10 02               BSET 0,PORTC
1697    0AB3    AD 0A               BSR TIMDLY
1698    0AB5    11 02               BCLR 0,PORTC
1699    0AB7    AD 06               BSR TIMDLY
1700    0AB9    5A                  DECX
1701    0ABA    26 EC               BNE DMPB1
1702    0ABC    BE 60               LDX WORK1          ; retrieve index
1703    0ABE    81                  RTS
1704
1705                        ;------------------------
1706    0ABF    B7 5F       TIMDLY: STA WORK2
1707    0AC1    3F 28               CLR TIMDL1
1708    0AC3    A6 04               LDA #4             ; was 12
1709    0AC5    B7 29               STA TIMDL2
1710    0AC7    3A 28       TD1:    DEC TIMDL1
1711    0AC9    26 FC               BNE TD1
1712    0ACB    3A 29               DEC TIMDL2
1713    0ACD    26 F8               BNE TD1
1714    0ACF    B6 5F               LDA WORK2
1715    0AD1    81                  RTS
1716
1717                        ;------------------------
1718    0AD2    B7 5F       CLRDLY: STA WORK2
1719    0AD4    3F 28               CLR TIMDL1
1720    0AD6    A6 18               LDA #24            ; was 12
1721    0AD8    B7 29               STA TIMDL2
1722    0ADA    20 EB               BRA TD1
1723                        ;------------------------
1724    0ADC    CD 04 94    CHKI:   JSR READ0
1725    0ADF    F1                  CMP ,X
1726    0AE0    25 04               BLO BADI
1727    0AE2    E1 01               CMP 1,X
1728    0AE4    23 05               BLS OKI
1729    0AE6    A6 15       BADI:   LDA #15H           ; SENSOR CURRENT FAULT
1730    0AE8    CC 07 4F            JMP SETFLT
1731    0AEB    81          OKI:    RTS
1732
1733                        ;------------------------
1734                                PAGE
1735                        ;------------------------

1736                        ; TC values are multip accurracy
1737    0AEC    389D 37CE 3705  TCTBL: DW 14493, 142E
        0AF2    3641
1738    0AF4    34CA 32BB 3172         DW 13514, 1298
        0AFA    2FA3
1739    0AFC    2DF5 2A76 2710         DW 11765, 1087(
        0B02    2534
```

```
1740   0B04   21F8 1F40 1CEF         DW  8696, 8000,
       0B0A   1AF1
1741   0B0C   17AD 151D 130E         DW  6061, 5405,
       0B12   115C
1742   0B14   0FA0                   DW  4000
1743   0B16
1744                         ;------------------------
---------------------------
1745   0B16   FFFF FFFF FFFF  RSTBL: DW  0FFFFH, 0FFFI
       0B1C   FFFF
1746   0B1E   DA51 B1E9 95F1         DW  55889, 45545,
       0B24   816D
1747   0B26   71BE 655B 5B55         DW  29118, 25947,
       0B2C   530D
1748   0B2E   4C18 462B 410F         DW  19480, 17963,
       0B34   3C9C
1749   0B36   38B3 353D 3226         DW  14515, 13629,
       0B3C   2F60
1750   0B3E   2CE0 2A9B 288A         DW  11488, 10907,
       0B44   26A6
1751   0B46   24E9 234F 21D4         DW  9449, 9039, 8t
       0B4C   2075
1752   0B4E   1F2E 1DFE 1CE1         DW  7982, 7678, 73
       0B54   1BD7
1753   0B56   1ADD 19F2 1914         DW  6877, 6642, 64
       0B5C   1843
1754   0B5E   177E 16C3 1611         DW  6014, 5827, 56
       0B64   1569
1755   0B66   14C9 1431 13A0         DW  5321, 5169, 50:
       0B6C   1315
1756   0B6E   1291 1212 1199         DW  4753, 4626, 45(
       0B74   1125
1757   0B76   10B6 104C 0FE5         DW  4278, 4172, 40t
       0B7C   0F83
1758   0B7E   0F24 0EC9 0E71         DW  3876, 3785, 369
       0B84   0E1D
1759   0B86   0DCB 0D7C 0D30         DW  3531, 3452, 337
       0B8C   0CE7
1760   0B8E   0C9F 0C5A 0C18         DW  3231, 3162, 309
       0B94   0BD7
1761   0B96   0B99 0B5C 0B22         DW  2969, 2908, 285(
       0B9C   0AE9
1762   0B9E   0AB1 0A7B 0A47         DW  2737, 2683, 2631, 2580
       0BA4   0A14
1763   0BA6   09E3 09B3 0984         DW  2531, 2483, 2436, 2391
       0BAC   0957
1764   0BAE   092A 08FF 08D5         DW  2346, 2303, 2261, 2220
       0BB4   08AC
1765   0BB6   0884 085D 0837         DW  2180, 2141, 2103, 2066
       0BBC   0812
1766   0BBE   07EE 07CA 07A7         DW  2030, 1994, 1959, 1926
       0BC4   0786
1767   0BC6   0765 0744 0725         DW  1893, 1860, 1829, 1798
       0BCC   0706
1768   0BCE   06E8 06CA 06AD         DW  1768, 1738, 1709, 1681
       0BD4   0691
1769   0BD6   0675 065A 063F         DW  1653, 1626, 1599, 1573
       0BDC   0625
1770   0BDE   060B 05F2 05DA         DW  1547, 1522, 1498, 1473
       0BE4   05C1
1771   0BE6   05A9 0592 057C         DW  1449, 1426, 1404, 1381
       0BEC   0565
1772   0BEE   054F 0539 0524         DW  1359, 1337, 1316, 1295
       0BF4   050F
1773   0BF6   04FB 04E7 04D3         DW  1275, 1255, 1235, 1216
       0BFC   04C0
1774   0BFE   04AD 049A 0488         DW  1197, 1178, 1160, 1142
       0C04   0476
1775   0C06   0464 0452 0441         DW  1124, 1106, 108°, 1072
       0C0C   0430
1776   0C0E   0420 040F 03FF         DW  1056, 1039, 1023, 1007
       0C14   03EF
```

```
1777    0C16    03E0 03D0 03C1              DW  992, 976, 961, 946
        0C1C    03B2
1778    0C1E    03A4 0395 0387              DW  932, 917, 903, 889
        0C24    0379
1779    0C26    036B 035D 0350              DW  875, 861, 848, 835
        0C2C    0343
1780    0C2E    0336 0329 031C              DW  822, 809, 796, 784
        0C34    0310
1781    0C36    0303 02F7 02EB              DW  771, 759, 747, 735
        0C3C    02DF
1782    0C3E    02D3 02C8 02BC              DW  723, 712, 700, 689
        0C44    02B1
1783    0C46    02A6 029B 0290              DW  678, 667, 656, 646
        0C4C    0286
1784    0C4E    027B 0271 0267              DW  635, 625, 615, 605
        0C54    025D
1785    0C56    0253 0249 023F              DW  595, 585, 575, 565
        0C5C    0235
1786    0C5E    022C 0222 0219              DW  556, 546, 537, 528
        0C64    0210
1787    0C66    0207 01FE 01F5              DW  519, 510, 501, 492
        0C6C    01EC
1788    0C6E    01E4 01DB 01D3              DW  484, 475, 467, 459
        0C74    01CA
1789    0C76    01C2 01BA 01B2              DW  450, 442, 434, 426
        0C7C    01AA
1790    0C7E    01A2 019A 0192              DW  418, 410, 402, 395
        0C84    018B
1791    0C86    0183 017C 0174              DW  387, 380, 372, 365
        0C8C    016D
1792    0C8E    0166 015E 0157              DW  358, 350, 343, 336
        0C94    0150
1793    0C96    0149 0142 013C              DW  329, 322, 316, 309
        0C9C    0135
1794    0C9E    012E 0128 0121              DW  302, 296, 289, 283
        0CA4    011B
1795    0CA6    0114 010E 0108              DW  276, 270, 264, 257
        0CAC    0101
1796    0CAE    00FB 00F5 00EF              DW  251, 245, 239, 233
        0CB4    00E9
1797    0CB6    00E3 00DD 00D8              DW  227, 221, 216, 210
        0CBC    00D2
1798    0CBE    00CC 00C7 00C1              DW  204, 199, 193, 187
        0CC4    00BB
1799    0CC6    00B6 00B1 00AB              DW  182, 177, 171, 166
        0CCC    00A6
1800    0CCE    00A0 009B 0096              DW  160, 155, 150, 145
        0CD4    0091
1801    0CD6    008C 0087 0082              DW  140, 135, 130, 125
        0CDC    007D
1802    0CDE    0078 0073 006E              DW  120, 115, 110, 105
        0CE4    0069
1803    0CE6    0065 0060 005B              DW  101, 96, 91, 87
        0CEC    0057
1804    0CEE    0052 004D 0049              DW  82, 77, 73, 68
        0CF4    0044
1805    0CF6    0040 003C 0037              DW  64, 60, 55, 51
        0CFC    0033
1806    0CFE    002F 002A 0026              DW  47, 42, 38, 34
        0D04    0022
1807    0D06    001E 001A 0015              DW  30, 26, 21, 17
        0D0C    0011
1808    0D0E    000D 0009 0005              DW  13, 9, 5, 1
        0D14    0001
1809
1810                                        ;---------------------
        ----------------------------
1811    0D16    0000 0000 0000      COCTBL: DW  0, 0, 0, 0
        0D1C    0000
1812    0D1E    0000 0000 0000              DW  0, 0, 0, 10
        0D24    000A
```

```
1813   0D26   000A 000A 000A         DW   10,  10,  10,  10
       0D2C   000A
1814   0D2E   000A 000A 000A         DW   10,  10,  10,  10
       0D34   000A
1815   0D36   000A 000A 000A         DW   10,  10,  10,  10
       0D3C   000A
1816   0D3E   0014 0014 0014         DW   20,  20,  20,  20
       0D44   0014
1817   0D46   0014 0014 0014         DW   20,  20,  20,  20
       0D4C   0014
1818   0D4E   0014 0014 0014         DW   20,  20,  20,  30
       0D54   001E
1819   0D56   001E 001E 001E         DW   30,  30,  30,  30
       0D5C   001E
1820   0D5E   001E 001E 001E         DW   30,  30,  30,  30
       0D64   001E
1821   0D66   001E 0028 0028         DW   30,  40,  40,  40
       0D6C   0028
1822   0D6E   0028 0028 0028         DW   40,  40,  40,  40
       0D74   0028
1823   0D76   0028 0028 0032         DW   40,  40,  50,  50
       0D7C   0032
1824   0D7E   0032 0032 0032         DW   50,  50,  50,  50
       0D84   0032
1825   0D86   0032 0032 003C         DW   50,  50,  60,  60
       0D8C   003C
1826   0D8E   003C 003C 003C         DW   60,  60,  60,  60
       0D94   003C
1827   0D96   003C 0046 0046         DW   60,  70,  70,  70
       0D9C   0046
1828   0D9E   0046 0046 0046         DW   70,  70,  70,  70
       0DA4   0046
1829   0DA6   0050 0050 0050         DW   80,  80,  80,  80
       0DAC   0050
1830   0DAE   0050 0050 005A         DW   80,  80,  90,  90
       0DB4   005A
1831   0DB6   005A 005A 005A         DW   90,  90,  90,  90
       0DBC   005A
1832   0DBE   0064 0064 0064         DW   100, 100, 100, 100
       0DC4   0064
1833   0DC6   0064 0064 006E         DW   100, 100, 110, 110
       0DCC   006E
1834   0DCE   006E 006E 006E         DW   110, 110, 110, 120
       0DD4   0078
1835   0DD6   0078 0078 0078         DW   120, 120, 120, 120
       0DDC   0078
1836   0DDE   0082 0082 0082         DW   130, 130, 130, 130
       0DE4   0082
1837   0DE6   008C 008C 008C         DW   140, 140, 140, 140
       0DEC   008C
1838   0DEE   0096 0096 0096         DW   150, 150, 150, 150
       0DF4   0096
1839   0DF6   00A0 00A0 00A0         DW   160, 160, 160, 160
       0DFC   00A0
1840   0DFE   00AA 00AA 00AA         DW   170, 170, 170, 170
       0E04   00AA
1841   0E06   00B4 00B4 00B4         DW   180, 180, 180, 190
       0E0C   00BE
1842   0E0E   00BE 00BE 00C8         DW   190, 190, 200, 200
       0E14   00C8
1843   0E16   00C8 00D2 00D2         DW   200, 210, 210, 210
       0E1C   00D2
1844   0E1E   00DC 00DC 00DC         DW   220, 220, 220, 230
       0E24   00E6
1845   0E26   00E6 00E6 00F0         DW   230, 230, 240, 240
       0E2C   00F0
1846   0E2E   00FA 00FA 00FA         DW   250, 250, 250, 260
       0E34   0104
1847   0E36   0104 010E 010E         DW   260, 270, 270, 280
       0E3C   0118
1848   0E3E   0118 0122 0122         DW   280, 290, 290, 300
       0E44   012C
```

```
1849   0E46   012C 0136 0136              DW  300, 310, 310, 320
       0E4C   0140
1850   0E4E   0140 014A 014A              DW  320, 330, 330, 340
       0E54   0154
1851   0E56   015E 015E 0168              DW  350, 350, 360, 360
       0E5C   0168
1852   0E5E   0172 017C 017C              DW  370, 380, 380, 390
       0E64   0186
1853   0E66   0190 019A 019A              DW  400, 410, 410, 420
       0E6C   01A4
1854   0E6E   01AE 01B8 01C2              DW  430, 440, 450, 450
       0E74   01C2
1855   0E76   01CC 01D6 01E0              DW  460, 470, 480, 490
       0E7C   01EA
1856   0E7E   01F4 01FE 0208              DW  500, 510, 520, 530
       0E84   0212
1857   0E86   021C 0226 023A              DW  540, 550, 570, 580
       0E8C   0244
1858   0E8E   024E 0258 026C              DW  590, 600, 620, 630
       0E94   0276
1859   0E96   0280 0294 029E              DW  640, 660, 670, 690
       0E9C   02B2
1860   0E9E   02BC 02D0 02E4              DW  700, 720, 740, 760
       0EA4   02F8
1861   0EA6   0302 0316 032A              DW  770, 790, 810, 830
       0EAC   033E
1862   0EAE   0352 0370 0384              DW  850, 880, 900, 920
       0EB4   0398
1863   0EB6   03B6 03D4 03E8              DW  950, 980, 1000, 1030
       0EBC   0406
1864   0EBE   0424 0442 046A              DW  1060, 1090, 1130, 1160
       0EC4   0488
1865   0EC6   04B0 04D8 0500              DW  1200, 1240, 1280, 1320
       0ECC   0528
1866   0ECE   055A 058C 05BE              DW  1370, 1420, 1470, 1520
       0ED4   05F0
1867   0ED6   062C 0668 06AE              DW  1580, 1640, 1710, 1780
       0EDC   06F4
1868   0EDE   0744 0794 07EE              DW  1860, 1940, 2030, 2130
       0EE4   0852
1869   0EE6   08B6 092E 09A6              DW  2230, 2350, 2470, 2610
       0EEC   0A32
1870   0EEE   0AD2 0B7C 0C3A              DW  2770, 2940, 3130, 3340
       0EF4   0D0C
1871   0EF6   0E06 0F14 1054              DW  3590, 3860, 4180, 4560
       0EFC   11D0
1872   0EFE   137E 1590 1810              DW  4990, 5520, 6160, 6910
       0F04   1B26
1873   0F06   1F22 2454 270F              DW  7970, 9300, 9999, 9999
       0F0C   270F
1874   0F0E   270F 270F 270F              DW  9999, 9999, 9999, 9999
       0F14   270F
1875
1876                                      ;-----------------------------------------
1877                                      ; The TADTBL or Temperature A/D TaBLe, is used to determine the CF index
1878   0F16   3B 44 4A 50 57              TADTBL:  DB  59, 68, 74, 80, 87, 94, 101, 109
       0F1B   5E 65 6D
1879   0F1E   75 7F 86 8E 97              DB  117, 127, 134, 142, 151, 159, 168, 176
       0F23   9F A8 B0
1880   0F26   B8 BF C6 CD D3              DB  184, 191, 198, 205, 211, 225, 255
       0F2B   E1 FF
1881
1882                                      ;-----------------------------------------
1883   0F2D                               END
1883   0F2D                               END
```

| Defined | Symbol Name | | | | Value | References | | | |
|---|---|---|---|---|---|---|---|---|---|
| 37 | ADCON | | | | = 000E | 739 | 740 | | |
| 38 | ADREG | | | | =. 000F | 741 | | | |
| 1729 | BADI | | | | 0AE6 | 1726 | | | |
| 476 | BADTMP | | | | 02CE | 472 | | | |
| 1152 | BAIL | | | | 072D | | | | |
| 100 | BCD0 | | | | = 0025 | 368 | 395 | 399 | 8 |
| 27 | 833 | 834 | 836 | 843 | | | | | |
| 101 | BCD1 | | | | = 0026 | 359 | 363 | 389 | 3 |
| 92 | 828 | 837 | 838 | 840 | 844 | | | | |
| 102 | BCD2 | | | | = 0027 | 829 | | | |
| 896 | BDWN | | | | 056B | 892 | | | |
| 901 | BDWN1 | | | | 0575 | 903 | | | |
| 907 | BDWN2 | | | | 0582 | 908 | | | |
| 910 | BDWN3 | | | | 0588 | 912 | 915 | | |
| 915 | BDWN3A | | | | 0593 | 917 | | | |
| 919 | BDWN4 | | | | 059C | 901 | 921 | | |
| 899 | BDWNA | | | | 0571 | 922 | | | |
| 960 | BFAULT | | | | 05EF | 926 | | | |
| 830 | BINB1 | | | | 0512 | 849 | | | |
| 848 | BINB2 | | | | 0532 | 841 | | | |
| 825 | BINBCD | | | | 0508 | 356 | 386 | | |
| 1246 | BLED | | | | 07CC | 1242 | 1244 | | |
| 1280 | BLMP1 | | | | 0809 | 1275 | | | |
| 1282 | BLMP2 | | | | 080E | 1277 | | | |
| 952 | BOUT | | | | 05DF | 963 | | | |
| 954 | BOUT1 | | | | 05E5 | 952 | | | |
| 86 | BTIMER | | | | = 005A | 893 | 897 | 910 | 9 |
| 19 | 939 | 957 | 1130 | 1132 | | | | | |
| 891 | BUTTON | | | | 0562 | 267 | 284 | 293 | 3 |
| 05 | | | | | | | | | |
| 1155 | BUZTBL | | | | 072E | 1114 | 1116 | 1118 | |
| 1091 | BUZZ1 | | | | 06B3 | 1126 | | | |
| 1097 | BUZZ2 | | | | 06BD | 1092 | | | |
| 1114 | BUZZ2A | | | | 06E1 | 1102 | 1107 | 1110 | 11 |
| 12 | | | | | | | | | |
| 1120 | BUZZ3 | | | | 06F0 | 1090 | | | |
| 1090 | BUZZZ | | | | 06B0 | | | | |
| 96 | CF.0 | | | | = 002E | 494 | 510 | | |
| 97 | CF.1 | | | | = 002F | 492 | 512 | | |
| 240 | CHECK | | | | 010D | 248 | | | |
| 790 | CHKH1 | | | | 04F8 | 779 | 783 | 787 | |
| 788 | CHKH2 | | | | 04F6 | 780 | 784 | | |
| 745 | CHKHB | | | | 04AC | 446 | 663 | | |
| 777 | CHKHH | | | | 04E1 | 686 | 689 | | |
| 1724 | CHKI | | | | 0ADC | 274 | 312 | 1458 | 14 |
| 66 | | | | | | | | | |
| 1574 | CHKLEDS | | | | 0A03 | | | | |
| 768 | CHKLES | | | | 04D3 | 641 | 774 | | |
| 1073 | CHKLO | | | | 0695 | 1066 | | | |
| 232 | CHKMOD | | | | 0100 | 228 | | | |
| 481 | CHKTAD | | | | 02D6 | 484 | | | |
| 1518 | CLEAR | | | | 09B1 | 1365 | 1372 | 1434 | |
| 1718 | CLRDLY | | | | 0AD2 | 884 | | | |
| 794 | CMPTBL | | | | 04FA | 768 | | | |
| 63 | COC1.0 | | | | = 0031 | 381 | 561 | 566 | 5 |
| 72 | 719 | 1380 | 1389 | 1414 | 1537 | | | | |
| 64 | COC1.1 | | | | = 0032 | 383 | 559 | 564 | 5 |
| 74 | 715 | 1382 | 1391 | 1415 | 1538 | | | | |
| 95 | COCHB | | | | = 0055 | 1518 | | | |
| 98 | COCIDX | | | | = 002D | 443 | 555 | 636 | 14 |
| 27 | 1539 | | | | | | | | |
| 1811 | COCTBL | | | | 0D16 | 558 | 560 | 563 | 5 |
| 65 | 1403 | 1407 | 1419 | 1423 | | | | | |
| Pre | CODE | | | | 0080 | 136 | 140 | 146 | |
| 67 | COHB0.0 | | | | = 0040 | 595 | 676 | 1519 | |
| 68 | COHB0.1 | | | | = 0041 | 599 | 679 | 1520 | |
| 69 | COHB0.2 | | | | = 0042 | 603 | 682 | 1521 | |
| 70 | COHB1.0 | | | | = 003A | 343 | 453 | 593 | 6 |
| 17 | 675 | 760 | 1522 | | | | | | |
| 71 | COHB1.1 | | | | = 003B | 345 | 451 | 597 | 6 |

| | | | | | | | | | |
|---|---|---|---|---|---|---|---|---|---|
| 20 | 678 | 756 | 1523 | | | | | | |
| | 72 | COHB1.2 | | | | = | 003C | 347 | 449 | 601 | 6 |
| 23 | 681 | 752 | 1524 | | | | | | |
| | 73 | CONST.0 | | | | = | 0043 | 350 | 353 | 511 | 5 |
| 14 | 517 | 520 | 590 | 605 | 609 | 612 | | | |
| | 74 | CONST.1 | | | | = | 0044 | 351 | 513 | 519 | 5 |
| 92 | 611 | | | | | | | | |
| | 75 | CTMP.0 | | | | = | 0045 | 581 | 616 | 677 | 7 |
| 85 | | | | | | | | | |
| | 76 | CTMP.1 | | | | = | 0046 | 584 | 619 | 680 | 7 |
| 81 | | | | | | | | | |
| | 77 | CTMP.2 | | | | = | 0047 | 587 | 622 | 683 | 7 |
| 77 | | | | | | | | | |
| | 862 | DAA | | | | | 0536 | 835 | 839 | | |
| | 865 | DAAHAI | | | | | 053C | 862 | | | |
| | 873 | DAALOW | | | | | 0544 | 864 | 869 | | |
| | 876 | DAANOO | | | | | 0549 | 873 | | | |
| | 879 | DAARTS | | | | | 054F | 877 | | | |
| | Pre | DATA | | | | | 0000 | | | | |
| | 1618 | DIS1 | | | | | 0A49 | 1604 | 1626 | | |
| | 1622 | DIS2 | | | | | 0A50 | 1620 | | | |
| | 99 | DISBUF | | | | = | 0028 | 106 | 107 | 362 | 3 |
| 67 | 391 | 394 | 398 | 402 | 403 | 410 | 412 | | |
| | | | | | | | | 418 | 1606 | 1646 | 16 |
| 49 | | | | | | | | | |
| | 1638 | DISC1 | | | | | 0A63 | 1642 | | | |
| | 1606 | DISCHR | | | | | 0A3B | 1610 | | | |
| | 1635 | DISCLR | | | | | 0A5D | 1601 | | | |
| | 1600 | DISPLAY | | | | | 0A31 | 225 | 404 | | |
| | 1616 | DISPLY | | | | | 0A45 | 1607 | | | |
| | 1030 | DIV52 | | | | | 064B | 613 | | | |
| | 1034 | DIVA | | | | | 0653 | 1049 | 1057 | | |
| | 1037 | DIVB | | | | | 0658 | 1035 | | | |
| | 1050 | DIVC | | | | | 0671 | 1044 | | | |
| | 1029 | DIVIDE | | | | | 0649 | 354 | 321 | | |
| | 1691 | DMPB1 | | | | | 0AA8 | 1701 | | | |
| | 1695 | DMPB2 | | | | | 0AAF | 1693 | | | |
| | 1689 | DMPBYT | | | | | 0AA4 | 1683 | | | |
| | 882 | DMPCHK | | | | | 0550 | 269 | 286 | 295 | 3 |
| 07 | 1450 | 1509 | | | | | | | |
| | 707 | DOLMP | | | | | 0473 | 705 | | | |
| | 272 | DSP1A | | | | | 014F | 270 | | | |
| | 289 | DSP1B | | | | | 0175 | 287 | | | |
| | 298 | DSP1C | | | | | 018B | 296 | | | |
| | 310 | DSP1D | | | | | 01A7 | 308 | | | |
| | 1453 | DSP1E | | | | | 0956 | 1451 | | | |
| | 1512 | DSP1F | | | | | 09AB | 1510 | | | |
| | 1488 | DSP1H | | | | | 0986 | | | | |
| | 54 | DSPBNC | | | | = | 005B | 1068 | 1074 | 1079 | |
| | 398 | DSPC1 | | | | | 0250 | 370 | | | |
| | 380 | DSPCOC | | | | | 0229 | 341 | | | |
| | 400 | DSPCOM | | | | | 0254 | 420 | | | |
| | 342 | DSPHB | | | | | 01EB | 226 | | | |
| | 1681 | DUMP | | | | | 0A9B | 887 | | | |
| | 1682 | DUMP1 | | | | | 0A9D | 1685 | | | |
| | 722 | ENBUZZ | | | | | 048E | 717 | | | |
| | 1234 | EOS | | | | | 07BA | 1235 | 1331 | 1337 | 13 |
| 55 | | | | | | | | | |
| | 1235 | EOS1 | | | | | 07BA | | | | |
| | 105 | ERRCOD | | | | = | 0022 | 415 | 419 | 1177 | |
| | 335 | ERRDJ | | | | | 01DA | 340 | 342 | | |
| | 408 | ERRDSP | | | | | 0261 | 265 | 282 | 335 | 3 |
| 80 | 953 | | | | | | | | |
| | 184 | EXTINT | | | | | 00B9 | 142 | | | |
| | 1418 | FIDXHI | | | | | 090F | 1401 | | | |
| | 1647 | FILDA | | | | | 0A6E | 1650 | | | |
| | 1646 | FILDSP | | | | | 0A6C | 224 | | | |
| | 932 | FIXB1 | | | | | 05B7 | 929 | | | |
| | 936 | FIXB2 | | | | | 05BF | 931 | 933 | 935 | |
| | 509 | FIXRS | | | | | 030F | 503 | | | |
| | 50 | FLAG0 | | | | = | 005D | 246 | 247 | 257 | 2 |
| 72 | 277 | 289 | 290 | 298 | 299 | 310 | 315 | | |
| | | | | | | | | 320 | 325 | 455 | 6 |

| | | | | | | | | | | | |
|---|---|---|---|---|---|---|---|---|---|---|---|
| 27 | 666 | 667 | 668 | 669 | 672 | 691 | 692 | | | | |
| | | | | | | | 695 | 697 | 700 | 7 | |
| 01 | 705 | 722 | 724 | 927 | 952 | 1067 | 1070 | | | | |
| | | | | | | | 1073 | 1076 | 1097 | 11 | |
| 03 | 1104 | 1105 | 1108 | 1129 | 1147 | 1176 | 1185 | | | | |
| | | | | | | | 1186 | 1219 | 1220 | 12 | |
| 23 | 1235 | 1236 | 1300 | 1301 | 1349 | 1360 | 1371 | | | | |
| | | | | | | | 1374 | 1435 | 1447 | 14 | |
| 54 | 1460 | 1497 | 1498 | 1513 | 1514 | 1527 | 1529 | | | | |
| | 51 | FLAG1 | | | | = | 005C | 264 | 270 | 281 | 2 |
| 87 | 296 | 308 | 340 | 342 | 357 | 364 | 380 | | | | |
| | | | | | | | 387 | 400 | 408 | 4 | |
| 16 | 454 | 665 | 671 | 714 | 1071 | 1077 | 1090 | | | | |
| | | | | | | | 1094 | 1127 | 1134 | 11 | |
| 78 | 1179 | 1451 | 1510 | 1660 | 1661 | | | | | | |
| | 1399 | FNDIDX | | | | | 08EA | 1410 | | | |
| | 479 | GETCOC | | | | | 02D3 | 328 | 337 | 441 | 4 |
| 63 | 1227 | 1378 | 1437 | | | | | | | | |
| | 529 | GETIDX | | | | | 0331 | 540 | | | |
| | 495 | GETRS | | | | | 02F2 | | | | |
| | 1426 | GIDX10 | | | | | 091F | 1405 | 1408 | 1416 | 14 |
| 21 | | | | | | | | | | | |
| | 545 | GIDXHI | | | | | 0350 | 531 | | | |
| | 1245 | GLED | | | | | 07CB | 1248 | | | |
| | 771 | GLOOK | | | | | 04DA | | | | |
| | 567 | GOTCOC | | | | | 037F | 562 | | | |
| | 553 | GOTIDX | | | | | 0360 | 527 | 535 | 538 | 5 |
| 43 | 548 | | | | | | | | | | |
| | 570 | HBCOC | | | | | 0380 | 329 | 338 | 1228 | 14 |
| 30 | 1438 | | | | | | | | | | |
| | 762 | HH1ON | | | | | 04CF | 754 | 758 | | |
| | 1103 | HHBUZZ | | | | | 06C7 | 1097 | 1099 | | |
| | 764 | HHO1FF | | | | | 04D1 | 753 | 757 | 761 | |
| | 671 | HHOFF | | | | | 042D | 664 | | | |
| | 665 | HHON | | | | | 0420 | | | | |
| | 151 | HICHKI | | | | | 0086 | 273 | 1457 | | |
| | 541 | HIIDX | | | | | 034A | | | | |
| | 469 | HITEMP | | | | | 02C6 | 486 | | | |
| | 1442 | ICYCLE | | | | | 093F | 1225 | 1373 | 1433 | |
| | 1409 | IDXNXT | | | | | 08FF | 1404 | 1420 | 1424 | |
| | 1411 | IDXOVR | | | | | 0903 | 1395 | | | |
| | 1286 | ILMP | | | | | 0813 | 1262 | 1265 | | |
| | 627 | INDCTR | | | | | 03E0 | 262 | 339 | 1431 | |
| | 202 | INITIO | | | | | 00CD | 206 | | | |
| | 155 | INITVAL | | | | | 008A | 202 | | | |
| | 1113 | KILBUZ | | | | | 06DF | 1103 | 1104 | | |
| | 628 | KILIND | | | | | 03E3 | 1180 | | | |
| | 675 | LAMPS | | | | | 0433 | 666 | 670 | | |
| | 83 | LBUZZ | | | | | = | 005E | 1091 | 1093 | 1115 | 15 |
| 32 | | | | | | | | | | | |
| | 340 | LCDDSP | | | | | 01E6 | 263 | 271 | 288 | 2 |
| 97 | 309 | 1432 | 1452 | 1511 | | | | | | | |
| | 1595 | LDATBL | | | | | 0A20 | 1577 | | | |
| | 1240 | LEDCHK | | | | | 07C0 | 280 | 1338 | | |
| | 638 | LEDST | | | | | 03F2 | | | | |
| | 639 | LEDST1 | | | | | 03F4 | | | | |
| | 802 | LEDTBL | | | | | 0501 | 644 | | | |
| | 1654 | LEFT | | | | | 0A75 | 360 | 369 | 390 | 3 |
| 96 | 417 | | | | | | | | | | |
| | 700 | LLEV | | | | | 0466 | 684 | 687 | | |
| | 80 | LLLMP | | | | | = | 0005 | 704 | | | |
| | 148 | LLVAL | | | | | 0080 | 685 | | | |
| | 1259 | LMPC1 | | | | | 07E2 | 1272 | | | |
| | 1269 | LMPC2 | | | | | 07F7 | 1260 | | | |
| | 1253 | LMPCHK | | | | | 07D7 | 279 | 1339 | | |
| | 82 | LMPMSK | | | | | = | 00E2 | 709 | | | |
| | 152 | LOCHKI | | | | | 0088 | 311 | 1465 | | |
| | 84 | LOFF.0 | | | | | = | 0038 | 956 | 1119 | 1120 | 11 |
| 22 | 1534 | | | | | | | | | | |
| | 85 | LOFF.1 | | | | | = | 0039 | 954 | 1117 | 1123 | 11 |
| 25 | 1533 | | | | | | | | | | |
| | 772 | LOOK1 | | | | | 04DB | 770 | | | |
| | 473 | LOTEMP | | | | | 02CB | 488 | | | |

| | | | | | | | | | |
|---|---|---|---|---|---|---|---|---|---|
| 1508 | LOW21 | | | | | 09A2 | 1461 | 1470 | 1483 | 1513 |
| 1513 | LOW22 | | | | | 09AB | | | | |
| 1480 | LOW25 | | | | | 097D | | | | |
| 284 | LOWC1 | | | | | 0167 | 281 | 289 | | |
| 293 | LOWC2 | | | | | 017D | 298 | | | |
| 563 | LOWCOC | | | | | 0375 | 557 | | | |
| 504 | LOWRS | | | | | 0304 | 497 | | | |
| 210 | MAIN | | | | | 00DA | | | | |
| 652 | MAP1 | | | | | 0409 | 650 | | | |
| 655 | MAP2 | | | | | 040E | 653 | | | |
| 658 | MAP3 | | | | | 0413 | 656 | | | |
| 661 | MAP4 | | | | | 0418 | 659 | | | |
| 43 | MATH.0 | | | | = | 004A | 344 | 382 | 502 | 508 |
| 536 | 549 | 573 | 579 | 594 | 615 | 747 | 759 | 831 | 992 | 1018 |
| 1037 | 1056 | 1381 | 1388 | 1406 | 1422 | | | | | |
| 44 | MATH.1 | | | | = | 004B | 346 | 384 | 500 | 506 |
| 532 | 545 | 575 | 582 | 598 | 618 | 749 | 755 | 832 | 991 | 1000 |
| 1017 | 1038 | 1383 | 1390 | 1402 | 1418 | | | | | |
| 45 | MATH.2 | | | | = | 004C | 348 | 526 | 585 | 602 |
| 621 | 751 | 971 | 990 | 1002 | 1016 | 1039 | 1394 | | | |
| 46 | MATH.3 | | | | = | 004D | 352 | 972 | 989 | 1004 |
| 1015 | 1040 | | | | | | | | | |
| 47 | MATH.4 | | | | = | 004E | 975 | 980 | 982 | 988 |
| 1007 | 1012 | 1013 | 1014 | 1029 | 1041 | | | | | |
| 48 | MATH.5 | | | | = | 004F | 976 | 983 | 985 | 987 |
| 1032 | 1042 | 1045 | 1050 | 1052 | | | | | | |
| 49 | MATH.6 | | | | = | 005F | 1033 | 1043 | 1047 | 1053 |
| 1055 | | | | | | | | | | |
| 89 | MAXLED | | | | = | 00CD | 1241 | | | |
| 188 | MEMCLR | | | | | 00BB | 208 | 886 | | |
| 190 | MEMINIT | | | | | 00BF | 194 | | | |
| 90 | MINLED | | | | = | 0066 | 1243 | | | |
| 1010 | MLWK2A | | | | | 0632 | 1020 | | | |
| 1014 | MLWK2B | | | | | 063A | 1010 | | | |
| 1015 | MLWK2C | | | | | 063C | 1009 | | | |
| 695 | MMLEV | | | | | 045D | 690 | 701 | | |
| 79 | MMLMP | | | | = | 0009 | 698 | | | |
| 149 | MMVAL | | | | | 0083 | 688 | | | |
| 36 | MSCREG | | | | = | 000A | 207 | | | |
| 971 | MUL16 | | | | | 05F6 | 515 | | | |
| 972 | MUL23 | | | | | 05F8 | 606 | | | |
| 973 | MUL24 | | | | | 05FA | | | | |
| 1005 | MULWK2 | | | | | 0629 | | | | |
| 999 | MULWK21 | | | | | 0623 | | | | |
| 1001 | MULWK22 | | | | | 0625 | 578 | 750 | 1386 | |
| 1003 | MULWK23 | | | | | 0627 | | | | |
| 888 | NDMP | | | | | 0561 | 882 | | | |
| 1146 | NEWTIM | | | | | 0723 | 1144 | | | |
| 893 | NOBUTT | | | | | 0567 | | | | |
| 724 | NOBUZZ | | | | | 0491 | 714 | 718 | 721 | |
| 1078 | NOCHNG | | | | | 06A0 | 1067 | 1072 | 1073 | |
| 81 | NOLMP | | | | = | 0000 | 706 | | | |
| 706 | NOLMPJ | | | | | 0471 | 673 | | | |
| 979 | NXT | | | | | 0605 | 994 | | | |
| 539 | NXTIDX | | | | | 0346 | 534 | 547 | 551 | |
| 58 | NXTIM.0 | | | | = | 0033 | 213 | 234 | 254 | 303 |
| 317 | 1148 | 1196 | 1308 | 1352 | 1444 | 1481 | 1494 | | | |
| 59 | NXTIM.1 | | | | = | 0034 | 216 | 237 | 256 | 304 |
| 319 | 1150 | 1198 | 1311 | 1354 | 1446 | 1482 | 1496 | | | |
| 253 | OC0 | | | | | 0125 | 330 | 1229 | 1362 | |
| 267 | OC01 | | | | | 0141 | 264 | 272 | | |
| 305 | OC1 | | | | | 0199 | 310 | | | |
| 320 | OC1A | | | | | 01B8 | 320 | | | |
| 1351 | OKDISP | | | | | 0894 | 1349 | | | |
| 454 | OKHB1 | | | | | 02B2 | 447 | | | |

```
1731    OKI                          OAEB    1728
 636    OKIND                        03EE     627
 489    OKTEMP                       02E6     477
  31    PADDR                  =     0004
 Pre    PAGE0                        0000
 246    PAUSE                        011A     246
  32    PBDDR                  =     0005
  33    PCDDR                  =     0006
  27    PORTA                  =     0000     261     630     632    6
  59     708    711    898    904    909     942     945
  65    1167   1175   1189   1224   1226    1258    1304    1135    1137    1164    11
                                                            1334    1347    1350    13
  70    1436
  28    PORTB                  =     0001                    458     629     645    6
  56    1190   1246   1305   1336   1348
  29    PORTC                  =     0002                    228     258     259    2
  76     314    326    327    429    437     650     882
                                                             883     885     923    9
  24    1099   1187   1302   1375   1376    1448    1449
                                                            1459    1491    1618    16
  21    1622   1624   1628   1636   1638    1640    1691
                                                            1694    1696    1698
  30    PORTD                  =     0003                    653     892     901    9
  12     915    921
 337    PROCES                       01DD     244
1568    PROCHK                       09F8    1340
1581    PROVR                        0A0E
1223    PWROUT                       07A8    1367
1184    PWRUP                        075D     230
 730    READ0                        0494     240     321     436    14
  55    1463   1500   1724
 732    READ1                        0498     242     323     439    12
  09    1322   1503
 734    READ2                        049C    1201    1240    1314    15
  79
 736    READ3                        04A0    1205    1273    1318    15
  72
 738    READAD                       04A2     731     733     735
 198    RESET                        00C6     144
1658    RIGHT                        0A79     365     393     401
1661    RIGHTA                       0A80    1659
1672    RIGHTB                       0A93    1660
 887    RJ                           055E     885
 989    ROT1                         0616     978
 987    ROTAT                        0612     979
1745    RSTBL                        0B16     499     501     505     5
  07     533    537    546    550
 103    SAVACC                 =     0024
  92    SAVE.0                 =     0056     435     461
  93    SAVE.1                 =     0048
  94    SAVE.2                 =     0049
 104    SAVX                   =     0023
  56    SECNT.0                =     0036     212     233    1138    11
  40    1149   1192   1307
  57    SECNT.1                =     0037     215     236    1141    11
  43    1151   1194   1310
 166    SEGTBL                       0091    1668
  88    SENSCHK                =     0058
1175    SETFLT                       074F     476     962    1171    12
  50    1281   1283   1295   1730
 705    SETLMP                       046E     694     699
1111    SHBUZZ                       06DB    1108
1108    SHCHK                        06D4    1105
 691    SHLEV                        0455     456     695     700
  78    SHLMP                  =     0011     693
1332    STAT                         0869    1345
1548    STATBL                       09D6    1333    1335
  91    STATE                  =     0057    1330    1332    1341    13
  42    1343   1568   1575
 185    SWINT                        00BA     143
1080    SWTEXT                       06A4    1069    1075
1443    TACO                         093F
```

| | | | | | | | |
|---|---|---|---|---|---|---|---|
| 1450 | TAC01 | | | 094D | 1454 | | |
| 1497 | TAC1A | | | 0990 | 1497 | | |
| 1878 | TADTBL | | | 0F16 | 481 | | |
| 87 | TBUTT | | = | 0059 | 891 | 918 | 925 | 9
36 1357 1361 1366
| 940 | TBUZZ | | | 05C7 | 951 | | |
| 943 | TBUZZ1 | | | 05CD | 944 | | |
| 948 | TBUZZ2 | | | 05D7 | 949 | | |
| 35 | TCR | | = | 0009 | 200 | 219 | 1063 |
| 1737 | TCTBL | | | 0AEC | 491 | 493 | |
| 1710 | TD1 | | | 0AC7 | 1711 | 1713 | 1722 |
| 34 | TDR | | = | 0008 | 221 | 1062 | |
| 66 | TEMP | | = | 003D | 243 | 324 | 440 | 4
79 1504
| 1299 | TEST | | | 0827 | 250 | 332 | |
| 1363 | TEST2 | | | 08AC | 1359 | | |
| 1370 | TEST4 | | | 08B8 | 1364 | | |
| 332 | TESTJ | | | 01D7 | 285 | 294 | 306 |
| 250 | TESTJ1 | | | 0122 | 268 | | |
| 1171 | TFAULT | | | 074A | 1204 | 1208 | 1212 | 12
15
| 1295 | TFON | | | 0821 | 1317 | 1321 | 1326 | 13
29
| 106 | TIMDL1 | | = | 0028 | 1707 | 1710 | 1719 |
| 107 | TIMDL2 | | = | 0029 | 1709 | 1712 | 1721 |
| 1706 | TIMDLY | | | 0ABF | 1695 | 1697 | 1699 |
| 1086 | TIME | | | 06AA | 1084 | | |
| 52 | TIME.0 | | = | 0050 | 1086 | 1088 | |
| 53 | TIME.1 | | = | 0051 | | | |
| 1089 | TIMEA | | | 06B0 | 1087 | | |
| 55 | TIMER | | = | 0035 | 431 | 432 | 900 | 9
02 906 907 914 916 941 943 947
943 1083 1085 11
63 1216
| 1061 | TIMINT | | | 0680 | 141 | | |
| 923 | TIMOUT | | | 05A5 | 911 | 920 | |
| 1591 | TLATBL | | | 0A0F | 1570 | | |
| 60 | TMP.0 | | = | 0052 | | | |
| 61 | TMP.1 | | = | 0053 | | | |
| 62 | TMP.2 | | = | 0054 | | | |
| 1360 | TSTOVR | | | 08A5 | 1439 | | |
| 485 | TSTTAD | | | 02DE | 482 | | |
| 429 | TSTVS | | | 027C | 292 | 300 | 1468 | 14
79
| 432 | TSTVS1 | | | 0282 | 433 | | |
| 1162 | TTOG | | | 073D | 1218 | | |
| 1167 | TTOG1 | | | 0747 | 1164 | | |
| 1330 | TWAIT | | | 0864 | 1296 | | |
| 1454 | TWAIT2 | | | 0956 | | | |
| 1216 | TWAT | | | 079C | 1172 | 1219 | |
| 1219 | TWAT1 | | | 07A3 | 1217 | | |
| 1134 | UPDAT | | | 070B | 1131 | | |
| 1137 | UPDAT1 | | | 0712 | 1134 | | |
| 1138 | UPDAT2 | | | 0714 | 1129 | 1133 | 1136 |
| 1129 | UPDATE | | | 0700 | 1095 | | |
| 65 | VSENS | | = | 0030 | 241 | 322 | 434 | 4
38 462 495 1501
| 461 | VSOK | | | 02BE | 444 | | |
| 740 | WAITAD | | | 04A6 | 740 | | |
| 39 | WORK1 | | = | 0060 | 524 | 529 | 539 | 5
42 553 554 637 707 710 769 937
950 974 993 10
06 1019 1031 1034 1254 1271 1398 1399
1409 1412 1426 16
16 1627 1635 1662 1669 1689 1702
| 40 | WORK2 | | = | 005F | 49 | 358 | 388 | 4
14 577 745 1011 1261 1268 1385 1663
1665 1667 1672 16
74 1706 1714 1718
| 41 | WORK3 | | = | 003E | 640 | 642 | 773 | 12
56 1263 1264 1274
| 42 | WORK4 | | = | 003F | 1257 | 1266 | 1267 | 12
76

Lines Assembled : 1883          Assembly Errors : 0

What is claimed and desired to be secured by Letters Patent of the United States is:

1. A monitoring instrument for use on a vehicle comprising:
   means for determining a concentration of carbon monoxide present at a location of the instrument on said vehicle;
   means for indicating said concentration;
   means for periodically calculating a level of carbon monoxhemoglobin %COHb in the blood of a person on said vehicle proximate to said instrument resulting from breathing said carbon monoxide, said level of carbon monoxhemoglobin %COHb being calculated using the equation:

$$\%COHb_p = \%COHb_o(K1) + K2 + COC(k3),$$

where $\%COHb_p$ is the present calculated level of %COHb, $\%COHb_o$ is the %COHb level as calculated at the time of the last periodic calculation, COC is the present measured CO concentration in PPM, and k1, K2 and K3 are predetermined constants; and
   means to actuate a device if the calculated level of carbon monoxhemoglobin %COHb in the blood exceeds a predetermined health hazard level.

2. The instrument of claim 1, wherein said device comprises means to disable a source of carbon monoxide on said vehicle in the event that a health hazard level of carbon monoxhemoglobin %COHb is calculated.

3. The instrument of claim 1, wherein said device includes a visual indicator.

4. The instrument of claim 1, wherein said device includes an audible indicator.

5. The instrument of claim 1, in which the means for periodically calculating the level of carbon monoxhemoglobin %COHb also calculates the rate of rise in the level of carbon monoxhemoglobin in the blood in terms of the rise in %COHb per operation cycle OC, said rate of rise in the level being calculated using the equation:

$$\%COHb_p - \%COHb_o = \%COHb/OC$$

where %COHb/OC is the rise in %COHb per one operation cycle of the instrument.

6. The instrument of claim 1 wherein said means for calculating the level of carbon monoxhemoglobin in the blood is a programmed microprocessor provided with RAM wherein said %COHb is stored, said means for determining the concentration of carbon monoxide present at the location of the instrument includes a carbon monoxide sensor, and said instrument further includes means to couple an output of the sensor to the microprocessor.

7. A method for generating a signal corresponding to a level of carbon monoxhemoglobin in the blood of a person on a vehicle by taking a signal which corresponds to a concentration of carbon monoxide present on said vehicle and enhancing that signal into another signal which corresponds to a level of carbon monoxhemoglobin in the blood of a person on said vehicle, comprising the steps of:
   determining the concentration of carbon monoxide present on said vehicle to produce a first signal which corresponds to said concentration;
   indicating said concentration;
   periodically taking said first signal and computing from it a second signal which corresponds to the level of carbon monoxhemoglobin in the blood of a person on said vehicle, said second signal being computed using the equation:

$$\%COHb_p = \%COGb_o(k1) + k2 + COC(K3)$$

where $\%COHb_p$ is the present computed level of %COHb, $\%COHb_o$ is the %COHb computed at the time of the last periodic computation, COC is the present measured CO concentration in PPM, and K1, K2 and K3 are predetermined constants; and
   actuating a device if said second signal exceeds a predetermined level.

8. The method of claim 7 wherein each periodic computation of said second signal is part of a periodic operation cycle and wherein the method further includes the step of periodically computing a rate of rise in the level of carbon monoxhemoglobin in the blood in terms of the rise of %COHb per periodic operation cycle OC, said rate of rise in the level of carbon monoxhemoglobin being calculated using the equation:

$$\%COHb_p - \%COHb_o = \%COHb/OC$$

where %COHb/OC is the rise in %COHb per one periodic operation cycle.

9. The method of claim 7 wherein said device performs the further step of:
   disabling a source of carbon monoxide on said vehicle in the event that the level of carbon monoxhemoglobin %COHb exceeds a predetermined level.

10. The method of claim 7 wherein said device includes a visual indicator.

11. The method of claim 7 wherein said device includes an audible indicator.

12. A monitoring instrument for use on a vehicle comprising:
    means for determining varying concentrations of carbon monoxide present at a location of said instrument on said vehicle;
    means for indicating said concentrations;
    microprocessor means for using said determined concentrations of carbon monoxide to calculate a level of carbon monoxhemoglobin in the blood of a person on the vehicle proximate to said instrument and to calculate a rate of rise of said level of carbon monoxhemoglobin; and
    means to actuate a device if the calculated level of carbon monoxhemoglobin exceeds a predetermined level.

13. The instrument of claim 12 wherein said device disables a source of carbon monoxide on the vehicle.

14. The instrument of claim 12 wherein said device includes a visual indicator.

15. The instrument of claim 12 wherein said device includes an audible indicator.

16. The instrument of claim 12 wherein said means for determining concentrations of carbon monoxhemoglobin includes a carbon monoxide sensor and the instrument further includes means to provide a temperature compensating voltage for said sensor.

* * * * *

UNITED STATES PATENT AND TRADEMARK OFFICE
CERTIFICATE OF CORRECTION

PATENT NO. : 4,860,223

DATED : August 22, 1989

INVENTOR(S) : Henry G. Grilk

It is certified that error appears in the above-identified patent and that said Letters Patent is hereby corrected as shown below:

ON TITLE PAGE:
Page 1, under References Cited, add the following:

U.S. Army Human Engineering Laboratory Technical Memorandum 11-77, A PROPOSAL FOR EVALUATING HUMAN EXPOSURE TO CARBON MONOXIDE CONTAMINATION IN MILITARY VEHICLES, March 1977.

Signed and Sealed this

Thirteenth Day of August, 1991

Attest:

HARRY F. MANBECK, JR.

*Attesting Officer*     *Commissioner of Patents and Trademarks*